United States Patent
Ogg et al.

(10) Patent No.: US 10,191,071 B2
(45) Date of Patent: Jan. 29, 2019

(54) CARTRIDGES AND INSTRUMENTS FOR SAMPLE ANALYSIS

(71) Applicant: IntegenX Inc., Pleasanton, CA (US)

(72) Inventors: James Ogg, Sunnyvale, CA (US); David Eberhart, Santa Clara, CA (US); William D. Nielsen, San Jose, CA (US); Helen Franklin, San Jose, CA (US); Stevan B. Jovanovich, Livermore, CA (US)

(73) Assignee: IntegenX, Inc., Pleasanton, CA (US)

( * ) Notice: Subject to any disclaimer, the term of this patent is extended or adjusted under 35 U.S.C. 154(b) by 143 days.

(21) Appl. No.: 15/037,039

(22) PCT Filed: Nov. 17, 2014

(86) PCT No.: PCT/US2014/066008
§ 371 (c)(1),
(2) Date: May 16, 2016

(87) PCT Pub. No.: WO2015/073999
PCT Pub. Date: May 21, 2015

(65) Prior Publication Data
US 2016/0305972 A1 Oct. 20, 2016

Related U.S. Application Data

(60) Provisional application No. 61/905,804, filed on Nov. 18, 2013, provisional application No. 61/981,678, filed on Apr. 18, 2014.

(51) Int. Cl.
*G01N 35/00* (2006.01)
*B01L 3/00* (2006.01)
(Continued)

(52) U.S. Cl.
CPC ........ *G01N 35/00663* (2013.01); *B01L 3/502* (2013.01); *B01L 3/50273* (2013.01);
(Continued)

(58) Field of Classification Search
CPC ...................................... G01N 35/00
See application file for complete search history.

(56) References Cited

U.S. PATENT DOCUMENTS

| 3,075,740 A | 1/1963 | McIntosh |
| 3,352,643 A | 11/1967 | Ando et al. |

(Continued)

FOREIGN PATENT DOCUMENTS

| CN | 1109597 A | 10/1995 |
| CN | 1146017 A | 3/1997 |

(Continued)

OTHER PUBLICATIONS

Lai et al., Design and dynamic characterization of "single-stroke" peristaltic PDMS micropumps, Lab Chip. Jan. 21, 2011; 11(2): 336-342, Published online Oct. 19, 2010.*

(Continued)

*Primary Examiner* — Aaron A Priest
(74) *Attorney, Agent, or Firm* — Weaver Austin Villeneuve & Sampson LLP

(57) ABSTRACT

Provided herein are instruments and cartridges for processing samples. The cartridges include fluidic circuits in which fluid movement can be regulated by diaphragm valves. In certain cartridges, deformable material providing a diaphragm contacts an interface in the instrument that actuates the diaphragm directly, without intervening actuation layer. Certain cartridges have a plurality of fluidic circuits and fluid distribution channels or pneumatic distribution channels configured to deliver fluids or pneumatic pressure to any of the fluidic circuits, selectively. Certain cartridges (Continued)

Normally Open Valve With Flexible Ram have compartments containing on-board reagents. Compartments can be closed by a film attached to a body the cartridge through a heat seal.

15 Claims, 28 Drawing Sheets

(51) Int. Cl.
  *B01L 7/00* (2006.01)
  *C12Q 1/6818* (2018.01)
  *C12Q 1/686* (2018.01)
  *C12Q 1/6888* (2018.01)

(52) U.S. Cl.
  CPC ... *B01L 3/502715* (2013.01); *B01L 3/502738* (2013.01); *B01L 3/502746* (2013.01); *B01L 7/52* (2013.01); *C12Q 1/686* (2013.01); *C12Q 1/6818* (2013.01); *C12Q 1/6888* (2013.01); *B01L 2200/026* (2013.01); *B01L 2200/027* (2013.01); *B01L 2200/04* (2013.01); *B01L 2200/0689* (2013.01); *B01L 2200/10* (2013.01); *B01L 2200/16* (2013.01); *B01L 2300/044* (2013.01); *B01L 2300/0627* (2013.01); *B01L 2300/0645* (2013.01); *B01L 2300/0672* (2013.01); *B01L 2300/087* (2013.01); *B01L 2300/0816* (2013.01); *B01L 2300/0864* (2013.01); *B01L 2300/0867* (2013.01); *B01L 2300/0887* (2013.01); *B01L 2300/12* (2013.01); *B01L 2300/123* (2013.01); *B01L 2300/18* (2013.01); *B01L 2300/1827* (2013.01); *B01L 2400/0421* (2013.01); *B01L 2400/0478* (2013.01); *B01L 2400/0487* (2013.01); *B01L 2400/0622* (2013.01); *B01L 2400/0638* (2013.01); *B01L 2400/0644* (2013.01); *B01L 2400/0655* (2013.01); *G01N 2035/00673* (2013.01)

(56) References Cited

U.S. PATENT DOCUMENTS

| | | |
|---|---|---|
| 3,433,257 A | 3/1969 | Donald |
| 3,568,692 A | 3/1971 | Metzger et al. |
| 3,662,517 A | 5/1972 | Tascher et al. |
| 4,011,357 A | 3/1977 | Haase |
| 4,113,665 A | 9/1978 | Law et al. |
| 4,390,307 A | 6/1983 | Rice |
| 4,847,120 A | 7/1989 | Gent |
| 4,963,498 A | 10/1990 | Hillman et al. |
| 5,085,757 A | 2/1992 | Karger et al. |
| 5,275,645 A | 1/1994 | Ternoir et al. |
| 5,338,427 A | 8/1994 | Shartle et al. |
| 5,364,759 A | 11/1994 | Caskey et al. |
| 5,376,252 A | 12/1994 | Ekstroem et al. |
| 5,387,505 A | 2/1995 | Wu |
| 5,453,163 A | 9/1995 | Yan |
| 5,482,836 A | 1/1996 | Cantor et al. |
| 5,523,231 A | 6/1996 | Reeve |
| 5,571,410 A | 11/1996 | Swedberg et al. |
| 5,587,128 A | 12/1996 | Wilding et al. |
| 5,589,136 A | 12/1996 | Northrup et al. |
| 5,635,358 A | 6/1997 | Wilding et al. |
| 5,639,428 A | 6/1997 | Cottingham |
| 5,675,155 A | 10/1997 | Pentoney, Jr. et al. |
| 5,681,946 A | 10/1997 | Reeve |
| 5,705,628 A | 1/1998 | Hawkins |
| 5,705,813 A | 1/1998 | Apffel et al. |
| 5,726,026 A | 3/1998 | Wilding et al. |
| 5,741,462 A | 4/1998 | Nova et al. |
| 5,750,015 A | 5/1998 | Soane et al. |
| 5,770,029 A | 6/1998 | Nelson et al. |
| 5,775,371 A | 7/1998 | Pan et al. |
| 5,776,748 A | 7/1998 | Singhvi et al. |
| 5,830,662 A | 11/1998 | Soares et al. |
| 5,842,787 A | 12/1998 | Kopf-Sill et al. |
| 5,856,174 A | 1/1999 | Lipshutz et al. |
| 5,863,502 A | 1/1999 | Southgate et al. |
| 5,872,010 A | 2/1999 | Karger et al. |
| 5,885,470 A | 3/1999 | Parce et al. |
| 5,898,071 A | 4/1999 | Hawkins |
| 5,908,552 A | 6/1999 | Dittmann et al. |
| 5,922,591 A | 7/1999 | Anderson et al. |
| 5,942,443 A | 8/1999 | Parce et al. |
| 5,948,684 A | 9/1999 | Weigl et al. |
| 5,951,262 A | 9/1999 | Hartman |
| 5,971,158 A | 10/1999 | Yager et al. |
| 5,994,064 A | 11/1999 | Staub et al. |
| 6,001,229 A | 12/1999 | Ramsey |
| 6,007,690 A | 12/1999 | Nelson et al. |
| 6,007,775 A | 12/1999 | Yager |
| 6,010,607 A | 1/2000 | Ramsey |
| 6,048,100 A | 4/2000 | Thrall et al. |
| 6,056,860 A | 5/2000 | Amigo et al. |
| 6,073,482 A | 6/2000 | Moles |
| 6,074,827 A | 6/2000 | Nelson et al. |
| 6,103,199 A | 8/2000 | Bjornson et al. |
| 6,110,343 A | 8/2000 | Ramsey et al. |
| 6,120,184 A | 9/2000 | Laurence et al. |
| 6,136,212 A | 10/2000 | Mastrangelo et al. |
| 6,153,389 A | 11/2000 | Haarer et al. |
| 6,168,948 B1 | 1/2001 | Anderson et al. |
| 6,176,962 B1 | 1/2001 | Soane et al. |
| 6,190,616 B1 | 2/2001 | Jovanovich et al. |
| 6,197,595 B1 | 3/2001 | Anderson et al. |
| 6,207,031 B1 | 3/2001 | Adourian et al. |
| 6,235,471 B1 | 5/2001 | Knapp et al. |
| 6,238,538 B1 | 5/2001 | Parce et al. |
| 6,251,343 B1 | 6/2001 | Dubrow et al. |
| 6,280,589 B1 | 8/2001 | Manz et al. |
| 6,319,476 B1 | 11/2001 | Victor, Jr. et al. |
| 6,321,791 B1 | 11/2001 | Chow |
| 6,322,683 B1 | 11/2001 | Wolk et al. |
| 6,326,068 B1 | 12/2001 | Kong et al. |
| 6,342,142 B1 | 1/2002 | Ramsey |
| 6,348,318 B1 | 2/2002 | Valkirs |
| 6,379,929 B1 | 4/2002 | Burns et al. |
| 6,387,234 B1 | 5/2002 | Yeung et al. |
| 6,387,707 B1 | 5/2002 | Seul et al. |
| 6,391,622 B1 | 5/2002 | Knapp et al. |
| 6,403,338 B1 | 6/2002 | Knapp et al. |
| 6,408,878 B2 | 6/2002 | Unger et al. |
| 6,423,536 B1 | 7/2002 | Jovanovich et al. |
| 6,429,025 B1 | 8/2002 | Parce et al. |
| 6,432,191 B2 | 8/2002 | Schutt |
| 6,432,290 B1 | 8/2002 | Harrison et al. |
| 6,454,924 B2 | 9/2002 | Jedrzejewski et al. |
| 6,461,492 B1 | 10/2002 | Hayashizaki et al. |
| 6,489,112 B1 | 12/2002 | Hadd et al. |
| 6,521,188 B1 | 2/2003 | Webster |
| 6,524,456 B1 | 2/2003 | Ramsey et al. |
| 6,527,003 B1 | 3/2003 | Webster |
| 6,531,041 B1 | 3/2003 | Cong et al. |
| 6,531,282 B1 | 3/2003 | Dau et al. |
| 6,532,997 B1 | 3/2003 | Bedingham et al. |
| 6,533,914 B1 | 3/2003 | Liu |
| 6,534,262 B1 | 3/2003 | McKernan et al. |
| 6,537,757 B1 | 3/2003 | Langmore et al. |
| 6,544,734 B1 | 4/2003 | Briscoe et al. |
| 6,551,839 B2 | 4/2003 | Jovanovich et al. |
| 6,581,441 B1 | 6/2003 | Paul |
| 6,581,899 B2 | 6/2003 | Williams |
| 6,605,454 B2 | 8/2003 | Barenburg et al. |
| 6,613,525 B2 | 9/2003 | Nelson et al. |
| 6,614,228 B2 | 9/2003 | Hofmann et al. |
| 6,618,679 B2 | 9/2003 | Loehrlein et al. |
| 6,620,584 B1 | 9/2003 | Chee et al. |
| 6,623,613 B1 | 9/2003 | Mathies et al. |
| 6,627,446 B1 | 9/2003 | Roach et al. |
| 6,629,820 B2 | 10/2003 | Kornelsen |
| 6,632,619 B1 | 10/2003 | Harrison et al. |

(56) References Cited

U.S. PATENT DOCUMENTS

| | | |
|---|---|---|
| 6,632,655 B1 | 10/2003 | Mehta et al. |
| 6,660,148 B2 | 12/2003 | Shoji et al. |
| 6,663,833 B1 | 12/2003 | Stave et al. |
| 6,685,442 B2 | 2/2004 | Chinn et al. |
| 6,685,678 B2 | 2/2004 | Evans et al. |
| 6,685,809 B1 | 2/2004 | Jacobson et al. |
| 6,740,219 B2 | 5/2004 | Kazumichi et al. |
| 6,752,922 B2 | 6/2004 | Huang et al. |
| 6,764,648 B1 | 7/2004 | Roach et al. |
| 6,782,746 B1 | 8/2004 | Hasselbrink, Jr. et al. |
| 6,786,708 B2 | 9/2004 | Brown et al. |
| 6,787,111 B2 | 9/2004 | Roach et al. |
| 6,793,753 B2 | 9/2004 | Unger et al. |
| 6,802,342 B2 | 10/2004 | Fernandes et al. |
| 6,803,019 B1 | 10/2004 | Bjornson et al. |
| 6,807,490 B1 | 10/2004 | Perlin |
| 6,824,663 B1 | 11/2004 | Boone |
| 6,829,753 B2 | 12/2004 | Lee et al. |
| 6,833,246 B2 | 12/2004 | Balasubramanian |
| 6,852,287 B2 | 2/2005 | Ganesan |
| 6,870,185 B2 | 3/2005 | Roach et al. |
| 6,883,774 B2 | 4/2005 | Nielsen et al. |
| 6,885,982 B2 | 4/2005 | Harris et al. |
| 6,899,137 B2 | 5/2005 | Unger et al. |
| 6,923,907 B2 | 8/2005 | Hobbs et al. |
| 6,929,030 B2 | 8/2005 | Unger et al. |
| 6,951,632 B2 | 10/2005 | Unger et al. |
| 6,953,058 B2 | 10/2005 | Fernandes et al. |
| 6,960,437 B2 | 11/2005 | Enzelberger et al. |
| 6,994,986 B2 | 2/2006 | Swartz et al. |
| 7,005,052 B2 | 2/2006 | Shimizu et al. |
| 7,005,292 B2 | 2/2006 | Wilding et al. |
| 7,005,493 B2 | 2/2006 | Huang et al. |
| 7,015,030 B1 | 3/2006 | Fouillet et al. |
| 7,046,357 B2 | 5/2006 | Weinberger et al. |
| 7,049,558 B2 | 5/2006 | Baer et al. |
| 7,081,191 B2 | 7/2006 | Shoji et al. |
| 7,087,380 B2 | 8/2006 | Griffiths et al. |
| 7,097,809 B2 | 8/2006 | Van Dam et al. |
| 7,105,300 B2 | 9/2006 | Parce et al. |
| 7,118,910 B2 | 10/2006 | Unger et al. |
| 7,142,987 B2 | 11/2006 | Eggers |
| 7,157,228 B2 | 1/2007 | Hashmi et al. |
| 7,169,557 B2 | 1/2007 | Rosenblum et al. |
| 7,170,050 B2 | 1/2007 | Turner et al. |
| 7,198,759 B2 | 4/2007 | Bryning et al. |
| 7,211,388 B2 | 5/2007 | Cash et al. |
| 7,217,367 B2 | 5/2007 | Huang et al. |
| 7,232,656 B2 | 6/2007 | Balasubramanian et al. |
| 7,244,559 B2 | 7/2007 | Rothberg et al. |
| 7,244,567 B2 | 7/2007 | Chen et al. |
| 7,244,961 B2 | 7/2007 | Jovanovich et al. |
| 7,258,744 B2 | 8/2007 | Sakurada et al. |
| 7,258,774 B2 | 8/2007 | Chou et al. |
| 7,279,146 B2 | 10/2007 | Nassef et al. |
| 7,282,361 B2 | 10/2007 | Hodge |
| 7,312,085 B2 | 12/2007 | Chou et al. |
| 7,312,611 B1 | 12/2007 | Harrison et al. |
| 7,323,305 B2 | 1/2008 | Leamon et al. |
| 7,329,388 B2 | 2/2008 | Guzman |
| 7,361,471 B2 | 4/2008 | Gerdes et al. |
| 7,419,578 B2 | 9/2008 | Sakai et al. |
| 7,438,856 B2 | 10/2008 | Jedrzejewski et al. |
| 7,445,926 B2 | 11/2008 | Mathies et al. |
| 7,473,342 B2 | 1/2009 | Ugai et al. |
| 7,473,397 B2 | 1/2009 | Griffin et al. |
| 7,486,865 B2 | 2/2009 | Foquet et al. |
| 7,488,603 B2 | 2/2009 | Gjerde et al. |
| 7,501,237 B2 | 3/2009 | Solus et al. |
| 7,526,741 B2 | 4/2009 | Lee et al. |
| 7,531,076 B2 | 5/2009 | Hayashizaki et al. |
| 7,537,886 B1 | 5/2009 | Nazarenko et al. |
| 7,575,865 B2 | 8/2009 | Leamon et al. |
| 7,584,240 B2 | 9/2009 | Eggers |
| 7,589,184 B2 | 9/2009 | Hogan et al. |
| 7,595,200 B2 | 9/2009 | Bedingham et al. |
| 7,645,580 B2 | 1/2010 | Barber et al. |
| 7,691,614 B2 | 4/2010 | Senapathy |
| 7,704,735 B2 | 4/2010 | Facer et al. |
| 7,718,442 B2 | 5/2010 | Davis et al. |
| 7,744,737 B1 | 6/2010 | James et al. |
| 7,745,207 B2 | 6/2010 | Jovanovich et al. |
| 7,749,365 B2 | 7/2010 | Nguyen et al. |
| 7,749,737 B2 | 7/2010 | McBride et al. |
| 7,763,453 B2 | 7/2010 | Clemmens et al. |
| 7,766,033 B2 | 8/2010 | Mathies et al. |
| 7,785,458 B2 | 8/2010 | Shimizu et al. |
| 7,790,368 B1 | 9/2010 | Fukuzono |
| 7,799,553 B2 | 9/2010 | Mathies et al. |
| 7,803,281 B2 | 9/2010 | Davies et al. |
| 7,817,273 B2 | 10/2010 | Bahatt et al. |
| 7,832,429 B2 | 11/2010 | Young et al. |
| 7,863,357 B2 | 1/2011 | Madabhushi et al. |
| 7,867,713 B2 | 1/2011 | Nasarabadi |
| 7,885,770 B2 | 2/2011 | Gill et al. |
| 7,892,856 B2 | 2/2011 | Grate et al. |
| 7,942,160 B2 | 5/2011 | Jeon et al. |
| 7,943,305 B2 | 5/2011 | Korlach et al. |
| 7,959,875 B2 | 6/2011 | Zhou et al. |
| 7,976,789 B2 | 7/2011 | Kenis et al. |
| 7,976,795 B2 | 7/2011 | Zhou et al. |
| 7,998,708 B2 | 8/2011 | Handique et al. |
| 8,007,746 B2 | 8/2011 | Unger et al. |
| 8,018,593 B2 | 9/2011 | Tan et al. |
| 8,053,192 B2 | 11/2011 | Bignell et al. |
| RE43,122 E | 1/2012 | Harrison et al. |
| 8,142,635 B2 | 3/2012 | Shimizu et al. |
| 8,221,990 B2 | 7/2012 | Mori et al. |
| 8,222,023 B2 | 7/2012 | Battrell et al. |
| 8,268,263 B2 | 9/2012 | Campbell et al. |
| 8,283,165 B2 | 10/2012 | Hogan et al. |
| 8,313,941 B2 | 11/2012 | Takayama et al. |
| 8,337,777 B2 | 12/2012 | Nurse et al. |
| 8,388,908 B2 | 3/2013 | Blaga et al. |
| 8,398,642 B2 | 3/2013 | Weekes |
| 8,420,318 B2 | 4/2013 | Mathies et al. |
| 8,431,384 B2 | 4/2013 | Hogan et al. |
| 8,501,305 B2 | 8/2013 | Barlow |
| 8,512,538 B2 | 8/2013 | Majlof et al. |
| 8,551,714 B2 | 10/2013 | Jovanovich et al. |
| 8,557,518 B2 | 10/2013 | Jovanovich et al. |
| 8,562,918 B2 | 10/2013 | Jovanovich et al. |
| 8,584,703 B2 | 11/2013 | Kobrin et al. |
| 8,672,532 B2 | 3/2014 | Jovanovich et al. |
| 8,748,165 B2 | 6/2014 | Vangbo et al. |
| 8,763,642 B2 | 7/2014 | Vangbo |
| 8,841,116 B2 | 9/2014 | Mathies et al. |
| 8,894,946 B2 | 11/2014 | Nielsen et al. |
| 9,012,236 B2 | 4/2015 | Jovanovich et al. |
| 9,121,058 B2 | 9/2015 | Jovanovich et al. |
| 9,291,284 B2 | 3/2016 | Penterman et al. |
| 9,341,284 B2 | 5/2016 | Vangbo |
| 9,592,501 B2 | 3/2017 | Jarvius et al. |
| 9,663,819 B2 | 5/2017 | Jovanovich et al. |
| 2001/0012612 A1 | 8/2001 | Petersen et al. |
| 2001/0041357 A1 | 11/2001 | Fouillet et al. |
| 2002/0003895 A1 | 1/2002 | Some |
| 2002/0022261 A1 | 2/2002 | Anderson et al. |
| 2002/0022587 A1 | 2/2002 | Ferguson et al. |
| 2002/0025529 A1 | 2/2002 | Quake et al. |
| 2002/0025576 A1 | 2/2002 | Northrup et al. |
| 2002/0042125 A1 | 4/2002 | Petersen et al. |
| 2002/0047003 A1 | 4/2002 | Bedingham et al. |
| 2002/0048536 A1 | 4/2002 | Bergh et al. |
| 2002/0051992 A1 | 5/2002 | Bridgham et al. |
| 2002/0055167 A1 | 5/2002 | Pourahmadi et al. |
| 2002/0058332 A1 | 5/2002 | Quake et al. |
| 2002/0068357 A1 | 6/2002 | Mathies et al. |
| 2002/0098097 A1 | 7/2002 | Singh |
| 2002/0110900 A1 | 8/2002 | Jovanovich et al. |
| 2002/0115201 A1 | 8/2002 | Barenburg et al. |
| 2002/0119480 A1 | 8/2002 | Weir et al. |
| 2002/0119482 A1 | 8/2002 | Nelson et al. |
| 2002/0137039 A1 | 9/2002 | Gessner |

(56) References Cited

U.S. PATENT DOCUMENTS

| | | |
|---|---|---|
| 2002/0139084 A1 | 10/2002 | Tobolka |
| 2002/0151089 A1 | 10/2002 | Chapman et al. |
| 2002/0157951 A1 | 10/2002 | Foret et al. |
| 2002/0160361 A1 | 10/2002 | Loehrlein et al. |
| 2002/0187560 A1 | 12/2002 | Pezzuto et al. |
| 2003/0008308 A1 | 1/2003 | Enzelberger et al. |
| 2003/0019753 A1 | 1/2003 | Ogle et al. |
| 2003/0021734 A1 | 1/2003 | Vann et al. |
| 2003/0029724 A1 | 2/2003 | Derand et al. |
| 2003/0070677 A1 | 4/2003 | Handique et al. |
| 2003/0087425 A1 | 5/2003 | Eggers |
| 2003/0087446 A1 | 5/2003 | Eggers |
| 2003/0087455 A1 | 5/2003 | Eggers et al. |
| 2003/0088657 A1 | 5/2003 | Eggers |
| 2003/0095897 A1 | 5/2003 | Grate et al. |
| 2003/0104466 A1 | 6/2003 | Knapp et al. |
| 2003/0129755 A1 | 7/2003 | Sadler et al. |
| 2003/0162304 A1 | 8/2003 | Dority et al. |
| 2003/0175706 A1 | 9/2003 | Zhang |
| 2003/0197139 A1 | 10/2003 | Williams |
| 2003/0198573 A1 | 10/2003 | Forood et al. |
| 2003/0215369 A1 | 11/2003 | Eggers et al. |
| 2003/0217923 A1 | 11/2003 | Harrison et al. |
| 2004/0003997 A1 | 1/2004 | Anazawa et al. |
| 2004/0013536 A1 | 1/2004 | Hower et al. |
| 2004/0014091 A1 | 1/2004 | Duck et al. |
| 2004/0018611 A1 | 1/2004 | Ward et al. |
| 2004/0021068 A1 | 2/2004 | Staats |
| 2004/0022676 A1 | 2/2004 | Hamilton et al. |
| 2004/0037739 A1 | 2/2004 | McNeely et al. |
| 2004/0038385 A1 | 2/2004 | Langlois et al. |
| 2004/0053290 A1 | 3/2004 | Terbrueggen et al. |
| 2004/0063217 A1 | 4/2004 | Webster et al. |
| 2004/0072278 A1 | 4/2004 | Chou et al. |
| 2004/0086427 A1 | 5/2004 | Childers et al. |
| 2004/0086870 A1 | 5/2004 | Tyvoll et al. |
| 2004/0101966 A1 | 5/2004 | Davis et al. |
| 2004/0115838 A1* | 6/2004 | Quake .................. B01D 57/02 436/538 |
| 2004/0132170 A1 | 7/2004 | Storek et al. |
| 2004/0146452 A1 | 7/2004 | Fujieda et al. |
| 2004/0151629 A1 | 8/2004 | Pease et al. |
| 2004/0185484 A1 | 9/2004 | Costa et al. |
| 2004/0197845 A1 | 10/2004 | Hassibi et al. |
| 2004/0200724 A1 | 10/2004 | Fujii et al. |
| 2004/0209354 A1 | 10/2004 | Mathies et al. |
| 2004/0217004 A1 | 11/2004 | Hayashizaki et al. |
| 2004/0219533 A1 | 11/2004 | Davis et al. |
| 2004/0224380 A1 | 11/2004 | Chou et al. |
| 2005/0026181 A1 | 2/2005 | Davis et al. |
| 2005/0026300 A1 | 2/2005 | Samper et al. |
| 2005/0042656 A1 | 2/2005 | Davis et al. |
| 2005/0047967 A1 | 3/2005 | Chuang et al. |
| 2005/0053952 A1 | 3/2005 | Hong et al. |
| 2005/0142663 A1 | 6/2005 | Parthasarathy et al. |
| 2005/0161326 A1 | 7/2005 | Morita et al. |
| 2005/0161669 A1 | 7/2005 | Jovanovich et al. |
| 2005/0181394 A1 | 8/2005 | Steemers et al. |
| 2005/0201901 A1 | 9/2005 | Grossman et al. |
| 2005/0221373 A1 | 10/2005 | Enzelberger et al. |
| 2005/0224134 A1 | 10/2005 | Yin et al. |
| 2005/0224352 A1 | 10/2005 | Harrison et al. |
| 2005/0241941 A1 | 11/2005 | Parce et al. |
| 2005/0250199 A1 | 11/2005 | Anderson et al. |
| 2005/0255000 A1 | 11/2005 | Yamamoto et al. |
| 2005/0255003 A1 | 11/2005 | Summersgill et al. |
| 2005/0255007 A1 | 11/2005 | Yamada et al. |
| 2005/0266582 A1 | 12/2005 | Modlin et al. |
| 2005/0287572 A1 | 12/2005 | Mathies et al. |
| 2006/0014177 A1 | 1/2006 | Hogan et al. |
| 2006/0027456 A1 | 2/2006 | Harrison et al. |
| 2006/0040300 A1 | 2/2006 | Dapprich et al. |
| 2006/0057209 A1 | 3/2006 | Chapman et al. |
| 2006/0073484 A1 | 4/2006 | Mathies et al. |
| 2006/0076068 A1 | 4/2006 | Young et al. |
| 2006/0140051 A1 | 6/2006 | Kim et al. |
| 2006/0163143 A1 | 7/2006 | Chirica et al. |
| 2006/0177832 A1 | 8/2006 | Brenner |
| 2006/0186043 A1 | 8/2006 | Covey et al. |
| 2006/0210994 A1 | 9/2006 | Joyce |
| 2006/0210998 A1 | 9/2006 | Kettlitz et al. |
| 2006/0260941 A1 | 11/2006 | Tan et al. |
| 2006/0263789 A1 | 11/2006 | Kincaid |
| 2006/0266645 A1 | 11/2006 | Chen et al. |
| 2006/0292032 A1 | 12/2006 | Hataoka et al. |
| 2007/0015179 A1 | 1/2007 | Klapperich et al. |
| 2007/0017812 A1 | 1/2007 | Bousse |
| 2007/0020654 A1 | 1/2007 | Blume et al. |
| 2007/0031865 A1 | 2/2007 | Willoughby |
| 2007/0034025 A1 | 2/2007 | Pant et al. |
| 2007/0105163 A1 | 5/2007 | Grate et al. |
| 2007/0122819 A1 | 5/2007 | Wu et al. |
| 2007/0175756 A1 | 8/2007 | Nguyen et al. |
| 2007/0183935 A1 | 8/2007 | Clemmens et al. |
| 2007/0184463 A1 | 8/2007 | Molho et al. |
| 2007/0184547 A1 | 8/2007 | Handique et al. |
| 2007/0202531 A1 | 8/2007 | Grover et al. |
| 2007/0218485 A1 | 9/2007 | Davis et al. |
| 2007/0237686 A1 | 10/2007 | Mathies et al. |
| 2007/0238109 A1 | 10/2007 | Min et al. |
| 2007/0248958 A1 | 10/2007 | Jovanovich et al. |
| 2007/0263049 A1 | 11/2007 | Preckel et al. |
| 2007/0292941 A1 | 12/2007 | Handique et al. |
| 2007/0297947 A1 | 12/2007 | Sommers et al. |
| 2008/0014576 A1 | 1/2008 | Jovanovich et al. |
| 2008/0014589 A1 | 1/2008 | Link et al. |
| 2008/0047836 A1 | 2/2008 | Strand et al. |
| 2008/0064610 A1 | 3/2008 | Lipovsek et al. |
| 2008/0124723 A1 | 5/2008 | Dale et al. |
| 2008/0131904 A1 | 6/2008 | Parce et al. |
| 2008/0138809 A1 | 6/2008 | Kapur et al. |
| 2008/0160630 A1 | 7/2008 | Liu et al. |
| 2008/0179255 A1 | 7/2008 | Jung et al. |
| 2008/0179555 A1 | 7/2008 | Landers et al. |
| 2008/0217178 A1 | 9/2008 | Ben-Asouli et al. |
| 2008/0237146 A1 | 10/2008 | Harrison et al. |
| 2008/0241844 A1 | 10/2008 | Kellogg |
| 2008/0242560 A1 | 10/2008 | Gunderson et al. |
| 2008/0257437 A1 | 10/2008 | Fernandes et al. |
| 2008/0262747 A1 | 10/2008 | Kain et al. |
| 2008/0281090 A1 | 11/2008 | Lee et al. |
| 2008/0302732 A1 | 12/2008 | Soh et al. |
| 2008/0311585 A1 | 12/2008 | Gao et al. |
| 2009/0004494 A1 | 1/2009 | Blenke et al. |
| 2009/0011959 A1 | 1/2009 | Costa et al. |
| 2009/0020427 A1 | 1/2009 | Tan et al. |
| 2009/0023603 A1 | 1/2009 | Selden et al. |
| 2009/0026082 A1 | 1/2009 | Rothberg et al. |
| 2009/0035770 A1 | 2/2009 | Mathies et al. |
| 2009/0053799 A1 | 2/2009 | Chang-Yen et al. |
| 2009/0056822 A1 | 3/2009 | Young et al. |
| 2009/0060797 A1 | 3/2009 | Mathies et al. |
| 2009/0084679 A1 | 4/2009 | Harrison et al. |
| 2009/0087850 A1 | 4/2009 | Eid et al. |
| 2009/0092970 A1 | 4/2009 | Williams et al. |
| 2009/0134069 A1 | 5/2009 | Handique |
| 2009/0137413 A1 | 5/2009 | Mehta et al. |
| 2009/0148933 A1 | 6/2009 | Battrell et al. |
| 2009/0178934 A1* | 7/2009 | Jarvius .............. B01L 3/502707 205/777.5 |
| 2009/0181411 A1 | 7/2009 | Battrell et al. |
| 2009/0183990 A1 | 7/2009 | Shoji et al. |
| 2009/0233325 A1 | 9/2009 | Mori et al. |
| 2009/0253181 A1 | 10/2009 | Vangbo et al. |
| 2009/0269504 A1 | 10/2009 | Liao |
| 2009/0286327 A1 | 11/2009 | Cho et al. |
| 2009/0311804 A1 | 12/2009 | McBrady et al. |
| 2009/0314970 A1 | 12/2009 | McAvoy et al. |
| 2009/0314972 A1 | 12/2009 | McAvoy et al. |
| 2009/0325183 A1 | 12/2009 | Lao et al. |
| 2009/0325276 A1 | 12/2009 | Battrell et al. |
| 2010/0010472 A1 | 1/2010 | Moore |
| 2010/0035252 A1 | 2/2010 | Rothberg et al. |
| 2010/0068723 A1 | 3/2010 | Jovanovich et al. |

(56) References Cited

U.S. PATENT DOCUMENTS

| | | |
|---|---|---|
| 2010/0075858 A1 | 3/2010 | Davis et al. |
| 2010/0092948 A1 | 4/2010 | Davis et al. |
| 2010/0093068 A1 | 4/2010 | Williams et al. |
| 2010/0111770 A1 | 5/2010 | Hwang et al. |
| 2010/0129810 A1 | 5/2010 | Greiner et al. |
| 2010/0137143 A1 | 6/2010 | Rothberg et al. |
| 2010/0165784 A1 | 7/2010 | Jovanovich et al. |
| 2010/0172898 A1 | 7/2010 | Doyle et al. |
| 2010/0173392 A1 | 7/2010 | Davis et al. |
| 2010/0173398 A1 | 7/2010 | Peterman |
| 2010/0178210 A1 | 7/2010 | Hogan et al. |
| 2010/0197507 A1 | 8/2010 | Rothberg et al. |
| 2010/0209957 A1 | 8/2010 | Hogan et al. |
| 2010/0210008 A1 | 8/2010 | Strand et al. |
| 2010/0218623 A1 | 9/2010 | Eggers et al. |
| 2010/0221726 A1 | 9/2010 | Zenhausern et al. |
| 2010/0228513 A1 | 9/2010 | Roth et al. |
| 2010/0233696 A1 | 9/2010 | Joseph et al. |
| 2010/0243916 A1 | 9/2010 | Maurer et al. |
| 2010/0248363 A1 | 9/2010 | Hogan et al. |
| 2010/0266432 A1 | 10/2010 | Pirk et al. |
| 2010/0285578 A1 | 11/2010 | Selden et al. |
| 2010/0285606 A1 | 11/2010 | Phillips et al. |
| 2010/0285975 A1 | 11/2010 | Mathies et al. |
| 2010/0291666 A1 | 11/2010 | Collier et al. |
| 2010/0303687 A1 | 12/2010 | Blaga et al. |
| 2010/0304355 A1 | 12/2010 | Shuler et al. |
| 2010/0304986 A1 | 12/2010 | Chen et al. |
| 2011/0003301 A1 | 1/2011 | Raymond et al. |
| 2011/0005932 A1* | 1/2011 | Jovanovich ...... G01N 35/00029 204/453 |
| 2011/0008785 A1 | 1/2011 | Tan et al. |
| 2011/0008813 A1 | 1/2011 | Dilleen et al. |
| 2011/0014606 A1 | 1/2011 | Steinmetzer et al. |
| 2011/0027913 A1 | 2/2011 | Bau et al. |
| 2011/0038758 A1 | 2/2011 | Akaba et al. |
| 2011/0039303 A1 | 2/2011 | Jovanovich et al. |
| 2011/0041935 A1 | 2/2011 | Zhou et al. |
| 2011/0045505 A1 | 2/2011 | Warthoe et al. |
| 2011/0053784 A1 | 3/2011 | Unger et al. |
| 2011/0070578 A1 | 3/2011 | Bell et al. |
| 2011/0124049 A1 | 5/2011 | Li et al. |
| 2011/0126910 A1 | 6/2011 | May |
| 2011/0127222 A1 | 6/2011 | Chang-Yen et al. |
| 2011/0136179 A1 | 6/2011 | Binlee et al. |
| 2011/0137018 A1 | 6/2011 | Chang-Yen et al. |
| 2011/0171086 A1 | 7/2011 | Prins et al. |
| 2011/0172403 A1 | 7/2011 | Harrold |
| 2011/0186466 A1 | 8/2011 | Kurowski et al. |
| 2011/0189678 A1 | 8/2011 | McBride et al. |
| 2011/0195495 A1 | 8/2011 | Selden et al. |
| 2011/0206576 A1 | 8/2011 | Woudenberg et al. |
| 2011/0207140 A1 | 8/2011 | Handique et al. |
| 2011/0212440 A1 | 9/2011 | Viovy et al. |
| 2011/0212446 A1 | 9/2011 | Wang et al. |
| 2011/0223605 A1 | 9/2011 | Bienvenue et al. |
| 2011/0229897 A1 | 9/2011 | Bell et al. |
| 2011/0229898 A1 | 9/2011 | Bell et al. |
| 2011/0256530 A1 | 10/2011 | Hogan |
| 2011/0312614 A1 | 12/2011 | Selden et al. |
| 2012/0055798 A1 | 3/2012 | Selden et al. |
| 2012/0100522 A1 | 4/2012 | Saghbini et al. |
| 2012/0181460 A1 | 7/2012 | Eberhart et al. |
| 2012/0240127 A1 | 9/2012 | Brittenham et al. |
| 2012/0267247 A1 | 10/2012 | Tan et al. |
| 2012/0279638 A1 | 11/2012 | Zhou et al. |
| 2012/0290648 A1 | 11/2012 | Sharkey |
| 2012/0308987 A1 | 12/2012 | Hogan et al. |
| 2012/0309637 A1 | 12/2012 | Schumm et al. |
| 2012/0315635 A1 | 12/2012 | Vangbo et al. |
| 2012/0322666 A1 | 12/2012 | Pham et al. |
| 2013/0053255 A1 | 2/2013 | Vangbo et al. |
| 2013/0074944 A1 | 3/2013 | Van Gelder |
| 2013/0084565 A1 | 4/2013 | Landers et al. |
| 2013/0105017 A1 | 5/2013 | Zhou et al. |
| 2013/0115607 A1 | 5/2013 | Nielsen et al. |
| 2013/0139895 A1* | 6/2013 | Vangbo ............. B01L 3/502738 137/2 |
| 2013/0203634 A1 | 8/2013 | Jovanovich et al. |
| 2013/0209326 A1 | 8/2013 | Williams et al. |
| 2013/0210129 A1 | 8/2013 | Selden et al. |
| 2013/0213810 A1 | 8/2013 | Tan et al. |
| 2013/0217026 A1 | 8/2013 | Egan et al. |
| 2013/0224846 A1 | 8/2013 | Jovanovich et al. |
| 2013/0230906 A1 | 9/2013 | Martinelli et al. |
| 2013/0240140 A1 | 9/2013 | Kurowski et al. |
| 2013/0260380 A1 | 10/2013 | Hall et al. |
| 2013/0287645 A1 | 10/2013 | Shaike et al. |
| 2013/0344475 A1 | 12/2013 | Jovanovich et al. |
| 2014/0045704 A1 | 2/2014 | Jovanovich et al. |
| 2014/0065628 A1 | 3/2014 | Van Gelder et al. |
| 2014/0065689 A1 | 3/2014 | Hogan et al. |
| 2014/0073043 A1 | 3/2014 | Holmes |
| 2014/0161686 A1 | 6/2014 | Bort et al. |
| 2014/0170645 A1 | 6/2014 | Jovanovich et al. |
| 2014/0246618 A1 | 9/2014 | Zhou et al. |
| 2014/0370519 A1 | 12/2014 | Vangbo et al. |
| 2015/0021502 A1 | 1/2015 | Vangbo |
| 2015/0024436 A1 | 1/2015 | Eberhart et al. |
| 2015/0136602 A1 | 5/2015 | Jovanovich et al. |
| 2015/0136604 A1 | 5/2015 | Nielsen et al. |
| 2016/0016140 A1 | 1/2016 | Jovanovich et al. |
| 2016/0053314 A1 | 2/2016 | Jovanovich et al. |
| 2016/0096176 A1 | 4/2016 | Jarvius et al. |
| 2016/0116439 A1 | 4/2016 | Kindwall et al. |
| 2016/0367981 A1 | 12/2016 | Wunderle et al. |
| 2017/0002399 A1 | 1/2017 | Eberhart et al. |
| 2017/0197213 A1 | 7/2017 | Nielsen et al. |

FOREIGN PATENT DOCUMENTS

| | | |
|---|---|---|
| CN | 1354692 A | 6/2002 |
| CN | 1593338 A | 3/2005 |
| CN | 101004423 A | 7/2007 |
| CN | 101312759 A | 11/2008 |
| CN | 101553306 | 10/2009 |
| CN | 102459565 | 5/2012 |
| EP | 0459241 B1 | 10/1994 |
| EP | 0637999 A1 | 2/1995 |
| EP | 0527905 B1 | 11/1995 |
| EP | 1065378 B1 | 4/2002 |
| EP | 1411340 A2 | 4/2004 |
| EP | 1411340 A3 | 5/2004 |
| EP | 1658890 B1 | 5/2008 |
| EP | 2345739 A2 | 7/2011 |
| EP | 2345739 A3 | 10/2011 |
| JP | H10206384 A | 8/1998 |
| JP | 2003536058 A | 12/2003 |
| JP | 2004025159 A | 1/2004 |
| JP | 2004108285 A | 4/2004 |
| JP | 2004180594 A | 7/2004 |
| JP | 2005323519 A | 11/2005 |
| JP | 2005337415 A | 12/2005 |
| JP | 2005345463 A | 12/2005 |
| JP | 2007155491 A | 6/2007 |
| JP | 2007198765 A | 8/2007 |
| JP | 2008513022 A | 5/2008 |
| WO | WO-9604547 A1 | 2/1996 |
| WO | WO-9852691 A1 | 11/1998 |
| WO | WO-9853300 A2 | 11/1998 |
| WO | WO-9853300 A3 | 2/1999 |
| WO | WO-9936766 A1 | 7/1999 |
| WO | WO-9940174 A1 | 8/1999 |
| WO | WO-0040712 A1 | 7/2000 |
| WO | WO-0060362 A1 | 10/2000 |
| WO | WO-0061198 A1 | 10/2000 |
| WO | WO-0101025 A2 | 1/2001 |
| WO | WO-0138865 A1 | 5/2001 |
| WO | WO-0101025 A3 | 7/2001 |
| WO | WO-0185341 A1 | 11/2001 |
| WO | WO-0224949 A1 | 3/2002 |
| WO | WO-0241995 A1 | 5/2002 |
| WO | WO-0243615 A2 | 6/2002 |
| WO | WO-0243615 A3 | 3/2003 |

(56) References Cited

FOREIGN PATENT DOCUMENTS

| | | |
|---|---|---|
| WO | WO-03062462 A2 | 7/2003 |
| WO | WO-03085379 A2 | 10/2003 |
| WO | WO-03085379 A3 | 12/2003 |
| WO | WO-2004038363 A2 | 5/2004 |
| WO | WO-2004062804 A1 | 7/2004 |
| WO | WO-2004080597 A2 | 9/2004 |
| WO | WO-2004098757 A2 | 11/2004 |
| WO | WO-2004038363 A3 | 12/2004 |
| WO | WO-2005072858 A1 | 8/2005 |
| WO | WO-2005075081 A1 | 8/2005 |
| WO | WO-2005121308 A1 | 12/2005 |
| WO | WO-2005123950 A2 | 12/2005 |
| WO | WO-2004098757 A3 | 5/2006 |
| WO | WO-2007002579 A2 | 1/2007 |
| WO | WO-2007064635 A1 | 6/2007 |
| WO | WO-2007082480 A1 | 7/2007 |
| WO | WO-2008012104 A2 | 1/2008 |
| WO | WO-2008024319 A2 | 2/2008 |
| WO | WO-2008030631 A2 | 3/2008 |
| WO | WO-2008024319 A3 | 4/2008 |
| WO | WO-2008039875 A1 | 4/2008 |
| WO | WO-2008012104 A3 | 5/2008 |
| WO | WO-2008115626 A2 | 9/2008 |
| WO | WO-2008115626 A3 | 11/2008 |
| WO | WO-2009008236 A1 | 1/2009 |
| WO | WO-2009015296 A1 | 1/2009 |
| WO | WO-2007002579 A3 | 9/2009 |
| WO | WO-2009108260 A2 | 9/2009 |
| WO | WO-2009129415 A1 | 10/2009 |
| WO | WO-2009108260 A3 | 12/2009 |
| WO | WO-2010041174 A1 | 4/2010 |
| WO | WO-2010041231 A2 | 4/2010 |
| WO | WO-2010042784 A3 | 7/2010 |
| WO | WO-2010041231 A3 | 9/2010 |
| WO | WO-2010109392 A1 | 9/2010 |
| WO | WO-2010130762 A2 | 11/2010 |
| WO | WO-2010141921 A1 | 12/2010 |
| WO | WO-2011003941 A1 | 1/2011 |
| WO | WO-2011011172 A1 | 1/2011 |
| WO | WO-2010130762 A3 | 2/2011 |
| WO | WO-2011012621 A1 | 2/2011 |
| WO | WO-2011034621 A2 | 3/2011 |
| WO | WO-2011056215 A1 | 5/2011 |
| WO | WO-2011084703 A2 | 7/2011 |
| WO | WO-2011094577 A2 | 8/2011 |
| WO | WO-2011034621 A3 | 11/2011 |
| WO | WO-2011084703 A3 | 12/2011 |
| WO | WO-2012024657 A1 | 2/2012 |
| WO | WO-2012024658 A2 | 2/2012 |
| WO | WO-2012136333 A2 | 10/2012 |
| WO | WO-2013130910 A1 | 9/2013 |
| WO | WO-2014014587 A2 | 1/2014 |
| WO | WO-2014055936 A1 | 4/2014 |
| WO | WO2015/073999 | 5/2015 |
| WO | WO2015/078998 | 6/2015 |

OTHER PUBLICATIONS

Tanaka et al., An active valve incorporated into a microchip using a high strain electroactive polymer, Sensors and Actuators B 184 (2013) 163-169, Apr. 20, 2013.*

Au et al., Microvalves and Micropumps for BioMEMS, Micromachines 2011, 2(2), 179-220, May 24, 2011.*

Amendment and Request for Correction of Inventorship dated Jan. 10, 2008 in U.S. Appl. No. 10/750,533.

Anderson, et al. A miniature integrated device for automated multistep genetic assays. Nucleic Acids Research. 2000;28:e60.

Armani, et al. Re-configurable fluid circuits by PDMS elastomer micromachining. Proceedings of IEEE Micro Electro Mechanical Systems: MEMS. 1999; 222-227.

Bennett, et al. Toward the 1,000 dollars human genome. Pharmacogenomics, 6 (4) 373-382. (Jun. 2005).

Bings, et al. Microfluidic Devices Connected to Fused-Silica Capillaries with Minimal Dead Dead Volume. Analytical Chemistry. 1999;71(15):3292-3296.

Blazej, et al. Microfabricated bioprocessor for integrated nanoliter-scale Sanger DNA sequencing. Proc. Natl. Acad. Sci. USA 2006;103:7240-7245.

Blazej, et al. Polymorphism Ratio Sequencing: A New Approach for Single Nucleotide Polymorphism Discovery and Genotyping. Genome Research. 2003;13:287-293.

Branton, et al. The potential and challenges of nanopore sequencing. Nat Biotechnol. Oct. 2008;26(10):1146-53. doi: 10.1038/nbt.1495.

Brenner, et al. Gene expression analysis by massively parallel signature sequencing (MPSS) on microbead arrays. Nature Biotechnology, 18: 630-634 (2000).

Buchholz, et al. The use of light scattering for precise characterization of polymers for DNA sequencing by capillary electrophoresis. Electrophoresis. 2001;22:4118-4128.

CAPLUS abstract of Krohkin et al. Modified silica as a stationary phase for ion chromatography. Journal of Chromatography A. 1995;706:93-8.

Chan, et al. Microfabricated Polymer Devices for Automated Sample Delivery of Peptides for Analysis by Electrospray Ionization Tandem Mass Spectrometry. Analytical Chemistry. 1999;71(20):4437-4444.

Chiem, et al. Microchip systems for immunoassay: an integrated immunoreactor with electrophoretic separation for serum theophylline determination. Clinical Chemistry.1998;44(3):591-598.

Chiem, et al. Room temperature bonding of micromachined glass devices for capillary electrophoresis. Sensors and Actuators. 2000;B63(3):147-152.

Chinese office action dated Jan. 31, 2011 for CN 200580035911.7. (in Chinese with English translation).

Chinese office action dated Jul. 8, 2011 for CN 200580035911.7. (in Chinese with English translation).

Coleman, et al. A sequential injection microfluidic mixing strategy. Microfluidics and Nanofluidics. 2005;319-327.

Zhang, et al. Microfabricated Devices for Capillary Electrophoresis-Electrospray Mass Spectrometry. Analytical Chemistry. 1999;71(15):3258-3264.

Curcio, et al. Continuous Segmented-Flow Polymerase Chain Reaction for High-Throughput Miniaturized DNA Amplification. Analytical Chemistry. 2003;75(1):1-7.

Datasheet Cycle Sequencing, Retrieved from the internet, URL:http//answers.com/topic/cyclesequencing. Printed Sep. 3, 2010, pp. 1-2.

Diehl et al. BEAMing: single-molecule PCR on microparticles in water-in-oil emulsions. Nature Methods 3(7):551-559 (2006).

Doherty, et al. Sparsely Cross-linked "Nanogel" Matrices as Fluid, Mechanically Stablized Polymer Networks for High-Throughput Microchannel DNA Sequencing. Analytical Chemistry. 2004;76:5249-5256.

Doherty, et al. Sparsely cross-linked "nanogels" for microchannel DNA sequencing. Electrophoresis. 2003;24(24):4170-4180.

Dorfman, et al. Contamination-Free Continuous Flow Microfluidic Polymerase Chain Reaction for Quantitative and Clinical Applications. Analytical Chemistry. 2005;77(11):3700-3704.

Doyle, et al. Self-Assembled Magnetic Matrices for DNA Separation Chips. Science. 2000;295:2237.

Dressman, et al. Transforming single DNA molecules into fluorescent magnetic particles for detection and enumeration of genetic variations. Proc Natl Acad Sci USA. 2003;100(15):8817-8822.

Eid, et al. Real-time DNA sequencing from single polymerase molecules. Science. Jan. 2, 2009;323(5910):133-8. doi: 10.1126/science.1162986. Epub Nov. 20, 2008.

Emrich, et al. Microfabricated 384-Lane Capillary Array Electrophoresis Bioanalyzer for Ultrahigh-Throughput Genetic Analysis. Analytical Chemistry. 2002;74(19):5076-5083.

Ericson, et al. Electroosmosis- and Pressure-Driven Chromatography in Chips Using Continuous Beds. Analytical Chemistry. 2000;72(1):81-87.

Erratum for Margulies, et al. Genome sequencing in microfabricated high-density picolitre reactors. Nature. 2005;437(7057):376-80.

European search report and search opinion dated Jun. 6, 2011 for Application No. 10011511.2.

(56) References Cited

OTHER PUBLICATIONS

European search report and search opinion dated Jun. 22, 2016 for EP Application No. 11818879.6.
European search report and search opinion dated Aug. 17, 2011 for Application No. 08799648.4.
European search report and search opinion dated Sep. 11, 2013 for EP Application No. 10784213.
European search report dated Jul. 13, 2016 for EP Application No. 09714332.5.
European search report dated Oct. 29, 2012 for EP Application No. 07853470.8.
European search report dated Dec. 18, 2009 for Application No. 03808583.3.
European search report dated Sep. 1, 2010 for Application No. 5804847.1.
Ewing, et al. Base-Calling of Automated Sequencer Traces Using Phred. I. Accuracy Assessment. Genome Research. 1998;8:175-185.
Ewing, et al. Base-Calling of Automated Sequencer Traces Using Phred. II. Error probabilities. Genome Research. 1998;8:186-194.
Figeys, et al. A Microfabricated Device for Rapid Protein Identification by Microelectrospray Ion Trap Mass Spectrometry. Analytical Chemistry. 1997;69(16):3153-3160.
Figeys, et al. An Integrated Microfluidics-Tandem Mass Spectrometry System for Automated Protein Analysis. Analytical Chemistry. 1998;70(18):3728-3734.
Figeys, et al. Microfabricated Device Coupled with an Electrospray Ionization Quadrupole Time-of-Flight Mass Spectrometer: Protein Identifications Based on Enhanced-Resolution Mass Spectrometry and Tandem Mass Spectrometry Data. Rapid Communications in Mass Spectrometry. 1998;12:1435-1444.
Figeys, et al. Nanoflow Solvent Gradient Delivery from a Microfabricated Device for Protein Identifications by Electrospray Ionization Mass Spectrometry. Analytical Chemistry. 1998;70(18):3721-3727.
Francis, et al. Flow analysis based on a pulsed flow of solution: theory, instrumentation and applications. Talanta. 2002;58(6):1029-1042.
Fuentes, et al. Detecting minimal traces of DNA using DNA covalently attached to superparamagnetic nanoparticles and direct PCR-ELISA. Biosens Bioelectron. Feb. 15, 2006;21(8):1574-80. Epub Aug. 29, 2005.
Fuller, et al. The challenges of sequencing by synthesis. Nat Biotechnol. Nov. 2009;27(11):1013-23. doi: 10.1038/nbt.1585. Epub Nov. 6, 2009.
Ghadessy, et al. Directed evolution of polymerase function by compartmentalized self-replication. Proc Natl Acad Sci USA. 2001;98:4552-4557.
Giddings, et al. A software system for data analysis in automated DNA sequencing. Genome Research. 1998;8:644-665.
Goll, et al. Microvalves with bistable buckled polymer diaphragms. Journal of Micromechanics and Microengineering. 1996;6:77-79.
Grodzinski, et al. Microfluidic System Integration in Sample Preparation Chip-Sets—a Summary. Conf. Proc. IEEE Eng. Med. Biol. Soc. 2004;4:2615-2618.
Grover, et al. An integrated microfluidic processor for single nucleotide polymorphism-based DNA computing. Lab on a Chip. 2005;5(10):1033-1040.
Grover, et al. Development and multiplexed control of latching pneumatic valves using microfluidic logical structures. Lab on a chip. 2006;6:623-631.
Grover, et al. Monolithic membrane valves and diaphragm pumps for practical large-scale integration into glass microfluidic devices. Sensors and Actuators. 2003;689:315-323.
Grover, et al. Practical Valves and Pumps for Large-Scale Integration into Microfludic Analysis Devices. Micro Total Analysis Systems. 2002;1:136-138.
Hansen, et al. A robust and scalable microfluidic metering method that allows protein crystal growth by free interface diffusion. Proc Natl Acad Sci USA. 2002;99(26):16531-16536.

Harrison, et al. Micromachining a Miniaturized Capillary Electrophoresis-Based Chemical Analysis System on a Chip. Science. 1993;261(5123):895-897.
Hayes, et al. EDGE: A Centralized Resource for the Comparison, Analysis, and Distribution of Toxicogenomic Information. Molecular Pharmacology. 2005;67(4):1360-1368.
Heath, et al. PCR primed with VNTR core sequences yields species specific patterns and hypervariable probes. Nucleic Acids Res. Dec. 11, 1993;21(24):5782-5.
Holland, et al. Point-of-care molecular diagnostic systems—past, present and future. Curr Opin Microbiol. Oct. 2005;8(5):504-9.
Hultman, et al. Bidirectional Solid-Phase Sequencing of In Vitro-Amplified Plasmid DNA. BioTechniques. 1991;10(1):84-93.
International Preliminary Report for corresponding PCT Application No. PCT/CA2000/01421 dated Feb. 14, 2002.
International Preliminary Report for corresponding PCT Application No. PCT/US2005/018678 dated Nov. 13, 2007.
International Preliminary Report for corresponding PCT Application No. PCT/US2005/033347 dated Mar. 20, 2007.
International Preliminary Report for corresponding PCT Application No. PCT/US2007/007381 dated Sep. 23, 2008.
International Preliminary Report for corresponding PCT Application No. PCT/US2007/002721 dated Aug. 5, 2008.
International Preliminary Report for corresponding PCT Application No. PCT/US2007/061573 dated Aug. 26, 2008.
International search report and written opinion dated Jan. 5, 2012 for PCT Application No. PCT/US2011/048527.
International search report and written opinion dated Jan. 29, 2016 for PCT Application No. PCT/US2015/056764.
International search report and written opinion dated Mar. 8, 2013 for PCT/US2012/061223.
International search report and written opinion dated Mar. 24, 2011 for PCT Application No. PCT/US2010/058227.
International search report and written opinion dated Apr. 30, 2012 for PCT/US2012/021217.
International search report and written opinion dated Jun. 9, 2011 for PCT Application No. PCT/US2011/030973.
International search report and written opinion dated Jul. 22, 2013 for PCT Application No. US2013/028462.
International search report and written opinion dated Sep. 1, 2010 for PCT Application No. PCT/US2010/040490.
International search report and written opinion dated Oct. 26, 2011 for PCT Application No. PCT/US11/38180.
International search report and written opinion dated Oct. 26, 2015 for PCT/US2015/028510.
Yu, et al. Towards stationary phases for chromatography on a microchip: Molded porous polymer monoliths prepared in capillaries by photoinitiated in situ polymerization as separation media for electrochromatography. Electrophoresis. 2000;21:120-127.
International search report dated Oct. 6, 2010 for PCT Application No. PCT/US10/37545.
International search report dated Apr. 5, 2001 for PCT Application No. PCT/CA2000/01421.
International search report dated May 14, 2010 for PCT Application No. PCT/US2009/006640.
International search report dated Jul. 11, 2008 for PCT Application No. PCT/US07/61573.
International search report dated Jul. 30, 2010 for PCT Application No. PCT/US2010/36464.
International search report dated Aug. 18, 2009 for PCT Application No. PCT/US09/00419.
International search report dated Aug. 23, 2006 for PCT Application No. PCT/US2005/033347.
International search report dated Aug. 26, 2004 PCT Application No. PCT/US2003/41466.
International search report dated Sep. 25, 2007 for PCT Application No. PCT/US2007/002721.
Zhang, et al. A Microdevice with Integrated Liquid Junction for Facile Peptide and Protein Analysis by Capillary Electrophoresis/Electrospray Mass Spectrometry. Analytical Chemistry. 2000;72(5):1015-1022.
International written opinion dated Oct. 6, 2010 for PCT Application No. PCT/US10/37545.

(56) References Cited

OTHER PUBLICATIONS

International written opinion report dated Jul. 30, 2010 for PCT Application No. PCT/US2010/36464.
Jacobson, et al. Electrokinetic Focusing in Microfabricated Channel Structures. Anal. Chem., 1997, 69 (16), pp. 3212-3217.
Japanese office action dated May 11, 2012 for Application No. 2008-553535 (English translation).
Japanese office action dated May 27, 2011 for Application No. 2007-532553 (in Japanese with English translation).
Japanese office action dated Jul. 28, 2011 for Application No. 2008-553535 (in Japanese with English translation).
Japanese Office Action dated Dec. 21, 2010 for Application No. JP2001-540363 (in Japanese with English translation).
Japanese Office Action dated Apr. 27, 2010 for Application No. JP2001-540363 (in Japanese with English translation).
Ju, et al. Fluorescence energy transfer dye-labeled primers for DNA sequencing and analysis. Proc. Natl. Acad. Sci. USA. 1995;92:4347-4351.
Kan, et al. A novel thermogelling matrix for microchannel DNA sequencing based on poly-N-alkoxyalkylaclylamide copolymers. Electrophoresis. 2003;24(24):4161-4169.
Koh, et al. Integrating Polymerase Chain Reaction, Valving, and Electrophoresis in a Plastic Device for Bacterial Detection. Analytical Chemistry. 2003;75(17):4591-4598.
Kopp, et al. Chemical Amplification Continuous-Flow PCR on a Chip. Science. 1998;280:1046-1048.
Lagally, et al. Fully integrated PCR-capillary electrophoresis microsystem for DNA analysis. Lab on a Chip. 2001;1(2):102-107.
Lagally, et al. Integrated Portable Genetic Analysis Microsystem for Pathogen/Infectious Disease Detection. Analytical Chemistry. 2004;76:3162-3170.
Lagally, et al. Monolithic integrated microfluidic DNA amplification and capillary electrophoresis analysis system. Sensors and Actuators. 2000;663(3)138-146.
Lagally, et al. Single-Molecule DNA Amplification and Analysis in an Integrated Microfluidic Device. Analytical Chemistry. 2001;73(3):565-570.
Lazar, et al. Subattomole-Sensitivity Microchip Nanoelectrospray Source with Time-of-Flight Mass Spectrometry Detection. Analytical Chemistry. 1999;71(17):3627-3631.
Li, et al. Integration of Microfabricated Devices to Capillary Electrophoresis-Electrospray Mass Spectrometry Using a Low Dead Volume Connection: Application to Rapid Analyses of Proteolytic Digests. Analytical Chemistry. 1999;71(15):3036-3045.
Li, et al. Rapid and sensitive separation of trace level protein digests using microfabricated devices coupled to a quadrupole—time-of-flight mass spectrometer. Electrophoresis. 2000;21:198-210.
Li, et al. Separation and Identification of Peptides from Gel-Isolated Membrane Proteins Using a Microfabricated Device for Combined Capillary Electrophoresis/Nanoelectrospray Mass Spectrometry. Analytical Chemistry. 2000;72(3):599-609.
Licklider, et al. A Micromachined Chip-Based Electrospray Source for Mass Spectrometry. Analytical Chemistry. 2000;72(2):367-375.
Lisec, et al. A bistable pneumatic microswitch for driving fluidic components. Sensors and Actuators. 1996;A54:746-749.
Liu, et al. Automated parallel DNA sequencing on multiple channel microchips. Proc. Natl. Acad. Sci. USA. 2000;97(10):5369-5374.
Liu, et al. Optimization of High-Speed DNA Sequencing on Microfabricated Capillary Electrophoresis Channels. Analytical Chemistry. 1999;71:566-573.
Lund-Olesen, et al. Capture of DNA in microfluidic channel using magnetic beads: Increasing capture efficiency with integrated microfluidic mixer. Journal of Magnetism and Magnetic Materials 311 (2007): 396-400.
Mamanova, et al. FRT-seq: amplification-free, strand-specific transcriptome sequencing. Nat Methods. Feb. 2010;7(2):130-2. doi: 10.1038/nmeth.1417. Epub Jan. 17, 2010.
Melin, et al. A Passive 2-Dimensional Liquid Sample Micromixer. 7th International Conference on Miniaturized Chemical and Biochemical Analysis Systems. 2003;167-170.

Metzker, M. Sequencing technologies—the next generation. Nat Rev Genet. Jan. 2010;11(1):31-46. doi: 10.1038/nrg2626. Epub Dec. 8, 2009.
MillGat pump user manual, version 2.12, published 2005, pp. 1-28.
Mitra, et al. Digital genotyping and haplotyping with polymerase colonies. Proc Natl Acad Sci USA. 2003.100(10):15926-5931.
Norris, et al. Fully-integrated, multiplexed STR-based human identification using a single microfluidic chip and automated instrument. Available at http://www.promega.com/geneticidproc/ussymp20proc/oralpresentations/landersbienvenue.pdf. Accessed Jun. 2, 2010.
Notice of allowance dated Jan. 31, 2017 for U.S. Appl. No. 14/552,389.
Notice of allowance dated Feb. 19, 2013 for U.S. Appl. No. 12/845,650.
Notice of allowance dated Apr. 25, 2013 for U.S. Appl. No. 12/815,685.
Notice of allowance dated May 3, 2010 for U.S. Appl. No. 11/670,866.
Notice of allowance dated May 5, 2015 for U.S. Appl. No. 13/202,884.
Notice of allowance dated Jun. 9, 2011 for U.S. Appl. No. 12/831,949.
Notice of allowance dated Jun. 25, 2014 for U.S. Appl. No. 13/656,503.
Notice of allowance dated Jul. 8, 2013 for U.S. Appl. No. 13/717,585.
Notice of allowance dated Nov. 12, 2014 for U.S. Appl. No. 13/967,957.
Notice of allowance dated Nov. 22, 2013 for U.S. Appl. No. 13/590,965.
Notice of allowance dated Dec. 7, 2012 for U.S. Appl. No. 12/795,515.
Obeid, et al. Microfabricated Device for DNA and RNA Amplification by Continuous-Flow Polymerase Chain Reaction and Reverse Transcription-Polymerase Chain Reaction with Cycle Number Selection. Analytical Chemistry. 2003;75(2): 288-295.
Ocvirk, et al. High Performance Liquid Chromatography Partially Integrated onto a Silicon Chip. Analytical Methods and Instrumentation. 1995;2:74-82.
Ocvirk, et al. Optimization of confocal epifluorescence microscopy for microchip-based miniaturized total analysis systems. The Analyst. 1998;123:1429-1434.
Office action dated Jan. 13, 2017 for U.S. Appl. No. 14/253,622.
Office action dated Jan. 17, 2014 for U.S. Appl. No. 13/656,503.
Office action dated Jan. 22, 2013 for U.S. Appl. No. 12/845,650.
Office action dated Feb. 14, 2017 for U.S. Appl. No. 14/804,675.
Office action dated Feb. 28, 2013 for U.S. Appl. No. 13/113,968.
Office action dated Mar. 19, 2009 for U.S. Appl. No. 11/670,866.
Office action dated Mar. 24, 2010 for U.S. Appl. No. 11/670,866.
Office action dated Mar. 24, 2015 for U.S. Appl. No. 13/202,884.
Office action dated Mar. 30, 2012 for U.S. Appl. No. 12/795,515.
Office action dated Apr. 1, 2014 for U.S. Appl. No. 13/202,884.
Office action dated Apr. 15, 2015 for U.S. Appl. No. 13/896,581.
Office action dated May 22, 2012 for U.S. Appl. No. 12/526,015.
Office action dated May 30, 2014 for U.S. Appl. No. 13/656,503.
Office action dated Jul. 1, 2016 for U.S. Appl. No. 14/253,622.
Office action dated Jul. 26, 2012 for U.S. Appl. No. 12/845,650.
Office action dated Aug. 9, 2016 for U.S. Appl. No. 14/500,846.
Office action dated Aug. 23, 2012 for U.S. Appl. No. 13/287,398.
Office action dated Aug. 24, 2012 for U.S. Appl. No. 12/026,510.
Office action dated Aug. 29, 2012 for U.S. Appl. No. 12/605,217.
Office action dated Sep. 11, 2014 for U.S. Appl. No. 13/967,957.
Office action dated Sep. 15, 2014 for U.S. Appl. No. 13/886,068.
Office action dated Oct. 29, 2013 for U.S. Appl. No. 13/202,884.
Office action dated Nov. 14, 2012 for U.S. Appl. No. 12/526,015.
Office action dated Dec. 29, 2016 for U.S. Appl. No. 14/824,333.
Office action dates Jan. 15, 2014 for U.S. Appl. No. 12/321,594.
Office action dates Feb. 27, 2013 for U.S. Appl. No. 13/590,965.
Office action dates Sep. 19, 2012 for U.S. Appl. No. 12/321,594.
Office action dates Dec. 7, 2012 for U.S. Appl. No. 13/590,051.
Office Action Final dated Feb. 6, 2008 issued in U.S. Appl. No. 11/139,018.
Office Action dated Apr. 27, 2007 in U.S. Appl. No. 11/139,018
Office Action dated Jul. 2, 2007 in U.S. Appl. No. 10/540,658.
Office Action dated Jul. 12, 2007 in U.S. Appl. No. 10/750,533.
Oh, et al. A review of microvalves. J. Micromech. Microeng. 2006; 16:R13-R39.

(56) References Cited

OTHER PUBLICATIONS

Ohori, et al. Partly disposable three-way mirovalve for a medical micro total analysis system (muTAS). Sensors and Actuators. 1998;A64(1): 57-62.
Oleschuk, et al. Trapping of Bead-Based Reagents within Microfluidic Systems: On-Chip Solid-Phase Extraction and Electrochromatography. Analytical Chemistry. 2000;72:585-590.
Olsen, et al. Immobilization of DNA Hydrogel Plugs in Microfluidic Channels. Analytical Chemistry. 2002;74:1436-1441.
Paegel, et al. High-throughput DNA sequencing with a 96-lane capillary array electrophoresis bioprocessor. Proc Natl Acad Sci USA. 2002;99:574-579.
Paegel, et al. Microchip Bioprocessor for Integrated Nanovolume Sample Purification and DNA Sequencing. Analytical Chemistry. 2002;74(19):5092-5098.
Paegel, et al. Microfluidic devices for DNA sequencing: sample preparation and electrophoretic analysis. Current Opinion in Biotechnology. 2003;14(1):42-50.
Paegel, et al. Turn Geometry for Minimizing Band Broadening in Microfabricated Capillary Electrophoresis Channels. Analytical Chemistry. 2000;72:3030-3037.
PCT Notification of Transmittal of the International Search Report and the Written Opinion of the International Searching Authority, or the Declaration, dated Jun. 17, 2008, Application No. PCT/US2007/082568.
Peoples, et al. Microfluidic Immunoaffinity Separations for Bioanalysis. J. Chromat. B. 2008;866:14-25 (available online Aug. 30, 2007).
Peterson, et al. Enzymatic Microreactor-on-a-Chip: Protein Mapping Using Trypsin Immobilized on Porous Polymer Monoliths Molded in Channels of Microfluidic Devices. Analytical Chemistry. 2002;74:4081-4088.
Ramsey, et al. Generating Electrospray from Microchip Devices Using Electroosmotic Pumping. Analytical Chemistry. 1997;69(6):1174-1178.
Rohr, et al. Porous polymer monoliths: Simple and efficient mixers prepared by direct polymerization in the channels of microfluidic chips. Electrophoresis. 2001;22:3959-3967.
Rye, et al. High-sensitivity two-color detection of double-stranded DNA with a confocal fluorescence gel scanner using ethidium homodimer and thiazole orange. Nucleic Acids Research. 1991;19(2):327-333.
Scherer, et al. High-Pressure Gel Loader for Capillary Array Electrophoresis Microchannel Plates. Biotechniques. 2001;31(5):1150-1154.
Schomburg, et al. Design Optimization of Bistable Microdiaphragm Valves. Sensors and Actuators. 1998;A64:259-264.
Seifar, et al. Capillary electrochromatography with 1.8-mum ODS-modified porous silica particles. Journal of Chromatography. 1998; A808:71-77.
Shaikh, et al. A modular microfluidic architecture for integrated biochemical analysis. Proc Natl Acad Sci U S A. Jul. 12, 2005;102(28):9745-50. Epub Jun. 28, 2005.
Shendure, et al. Next-generation DNA sequencing. Nat Biotechnol. Oct. 2008;26(10):1135-45. doi: 10.1038/nbt1486.
Simpson, et al. High-throughput genetic analysis using microfabricated 96-sample capillary array electrophoresis microplates. Proc Natl Acad Sci USA. 1998;95:2256-2261.
Simpson, et al. Microfabrication Technology for the Production of Capillary Array Electrophoresis Chips. Biomedical Microdevices. 1998;1:7-26.
Soper, et al. Sanger DNA Sequencing Reactions Performed in a Solid-Phase Nanoreactor Directly Coupled to Capillary Gel Electrophoresis. Analytical Chemistry. 1998;70:4036-4043.
Spiering, et al. Novel microstructures and technologies applied in chemical analysis techniques. 1997 International Conference on Solid-State Sensors and Actuators. 1997;1:511-514.
Stevens, et al. Bacterial Separation and Concentration from Complex Sample Matrices: a Review. Crit. Rev. Microbiol. 2004;30(1):7-24.

Takao, et al. A Pneumatically Actuated Full In-Channel Microvalve With MOSFET-Like Function in Fluid Channel Networks. Journal of Microelectromechanical Systems. 2002;11(5):421-426.
Takao, et al. Microfluidic Integrated Circuits for Signal Processing Using Analogous Relationship Betweeen Pneumatic Microvalve and MOSFET. Journal of Microelectromechanical Systems. 2003;12(4):497-505.
Thomas, et al. Application of Genomics to Toxicology Research. Environmental Health Perspectives. 2002;110(6):919-923.
Tice, et al. Formation of Droplets and Mixing in Multiphase Microfluidics at Low Values of the Reynolds and the Capillary Numbers. Langmuir. 2003;19:9127-9133.
Todd Thorsen, et al., "Microfluidic Large-Scale Integration", www.sciencemag.org, Science, vol. 298, Oct. 18, 2002, pp. 580-584.
Unger, et al. Monolithic microfabricated valves and pumps by multilayer soft lithography. Science. Apr. 7, 2000;288(5463):113-6.
U.S. Appl. No. 10/540,658 Office Action Final dated Feb. 19, 2008.
U.S. Appl. No. 61/709,417, filed Oct. 4, 2012.
U.S. Appl. No. 90/011,453, filed Jan. 21, 2011.
U.S. Appl. No. 14/032,173, filed Sep. 10, 2013.
U.S. Appl. No. 14/474,047, filed Aug. 29, 2014.
Van Der Moolen, et al. A Micromachined Injection Device for CZE: Application to Correlation CZE. Analytical Chemistry. 1997;69(20):4220-4225.
Van Der Moolen, et al. Correlation Capillary Zone Electrophoresis, a Novel Technique to Decrease Detection Limits. Chromatographia. 1995;40(7/8):368-374.
Van Ness, et al. Isothermal Reactions for the Amplification of Oligonucleotides. Proc. Nat. Acad. Sci. USA. 2003;100 (8):4504-4509.
Vazquez, et al. Electrophoretic Injection within Microdevices. Analytical Chemistry. 2002;74:1952-1961.
Veenstra, et al. The design of an in-plane compliance structure for microfluidical systems. Sensors and Actuators. 2002;681:377-383.
Waller, et al. Quantitative Immunocapture PCR Assay for Detection of Campylobacter jejuni in Foods. Applied Environmental Microbiology. 2000; 66(9):4115-4118.
Weimer, et al. Solid-Phase Capture of Proteins, Spores, and Bacteria. Applied Environmental Microbiology. 2001;67(3):1300-1307.
Wen, et al. Microfabricated isoelectric focusing device for direct electrospray ionization-mass spectrometry. Electrophoresis. 2000;21:191-197.
Wikipedia brochure for defining stocahstic process. Sep. 2, 2009.
Williams, et al. Amplification of complex gene libraries by emulsion PCR. Nature Methods. 2006;3(7):545-50.
Woolley, et al. Functional Integration of PCR Amplification and Capillary Electrophoresis in a Microfabricated DNA Analysis Device. Analytical Chemistry. 1996;68(23):4081-4086.
Wright, et al. Behavior and Use of Nonaqueous Media without Supporting Electrolyte in Capillary Electrophoresis and Capillary Electrochromatography. Analytical Chemistry. 1997;69(16):3251-3259.
Xiang, et al. An Integrated Microfabricated Device for Dual Microdialysis and On-Line ESI-Ion Trap Mass Spectrometry for Analysis of Complex Biological Samples. Analytical Chemistry. 1999;71(8):1485-1490.
Xue, et al. Integrated Multichannel Microchip Electrospray Ionization Mass Spectrometry: Analysis of Peptides from On-Chip Tryptic Digestion of Melittin. Rapid Communications in Mass Spectrometry. 1997;11:1253-1256.
Xue, et al. Multichannel Microchip Electrospray Mass Spectrometry. Analytical Chemistry. 1997;69(3):426-430.
Yang, et al. A MEMS thermopneumatic silicone rubber membrane valve. Sensors and Actuators. 1998;A64(1):101-108.
Yu, et al. Preparation of Monolithic Polymers with Controlled Porous Properties for Microfluidic Chip Applications Using Photoinitiated Free Radial Polymerization. Journal of Polymer Science. 2002;40:755-769.
European search report with written opinion dated Jul. 12, 2017 for EP14861199.
Notice of allowance dated Jun. 9, 2017 for U.S. Appl. No. 14/824,333.
Notice of allowance dated Jun. 12, 2017 for U.S. Appl. No. 14/804,675.

(56) References Cited

OTHER PUBLICATIONS

Notice of allowance dated Jun. 22, 2017 for U.S. Appl. No. 14/824,333.
Co-pending U.S. Appl. No. 15/342,914, filed Nov. 3, 2016.
Krsek, et al. Comparison of different methods for the isolation and purification of total community DNA from soil. Journal of Microbiological Methods 39.1 (1999): 1-16.
International Preliminary Report on Patentability, issued in PCT Application No. PCT/US14/66008, dated May 24, 2016.
International Search Report and Written Opinion, issued in PCT Application No. PCT/US14/66008, dated Mar. 3, 2015.
CN Search Report issued in Application No. 201480071855.1, dated Apr. 12, 2017.
CN First Office Action issued in Application No. 201480071855.1, dated Apr. 12, 2017.
CN Supplemental Search Report issued in Application No. 201480071855.1, dated Feb. 4, 2018.
CN Second Office Action issued in Application No. 201480071855.1, dated Feb. 11, 2018.
EP Search Report and Written Opinion issued in Application No. EP 14 861 199.9, dated Oct. 18, 2017.
Co-pending U.S. Appl. No. 15/117,053, filed Aug. 5, 2016.
Co-pending U.S. Appl. No. 15/154,086, filed May 13, 2016.
International search report and written opinion dated Mar. 3, 2015 for PCT Application No. PCT/US2014/066008.
Co-pending U.S. Appl. No. 14/659,108, filed Mar. 16, 2015.
Co-pending U.S. Appl. No. 14/824,333, filed Aug. 12, 2015.
Co-pending U.S. Appl. No. 14/919,620, filed Oct. 21, 2015.
Office Action issued in U.S. Appl. No. 15/117,053, dated May 7, 2018.
Office Action issued in U.S. Appl. No. 15/173,894, dated Jan. 23, 2018.
International Search Report and Written Opinion issued in Application No. PCT/US2016/037711 dated Sep. 16, 2016.
International Preliminary Report of Patentability issued in Application No. PCT/US2016/037711 dated Dec. 19, 2017.
International Preliminary Report of Patentability issued in Application No. PCT/US15/28510 dated Dec. 1, 2016.
CN Third Office Action issued in Application No. 201480071855.1, Global Dossier dated Aug. 13, 2018.
First Examination Report dated Oct. 9, 2018, issued in Application No. 14861199.9.

\* cited by examiner

Move lysis solution into sample container (sample container vented on top). Heat container, aspirate mix if required.

Pull lysate back into syringe, capturing DNA on solid phase in reaction chamber

Move lysis solution into waste

Push/pull STR mastermix and primers into STR reaction chamber

Thermal cycle to amplify STRs

Fill syringe with air (open vent), push STR products to output

Normally Open Valve With Flexible Ram

CARTRIDGES AND INSTRUMENTS FOR SAMPLE ANALYSIS

CROSS-REFERENCE

This application claims the benefit of the filing dates of U.S. provisional application 61/905,804 filed Nov. 18, 2013 and of U.S. provisional application 61/981,678, filed Apr. 14, 2014, each of which is incorporated by reference in its entirely.

STATEMENT AS TO FEDERALLY SPONSORED RESEARCH

None.

BACKGROUND OF THE INVENTION

One barrier to the broad adoption of rapid DNA-based human identification is the consumable cost. A low-cost cartridge using small amounts of reagents would reduce this barrier. Previous approaches have focused on automation and manufacturing process improvement to reduce the cost to make a given cartridge.

Versions of systems including sample cartridges and fluidic systems for sample extraction and analysis are described in, for example, U.S. Pat. No. 6,190,616 (Jovanovich et al.); U.S. Pat. No. 6,551,839 (Jovanovich et al.); U.S. Pat. No. 6,870,185 (Jovanovich et al.); U.S. Pat. No. 7,244,961 (Jovanovich et al.); U.S. Pat. No. 7,445,926 (Mathies et al.); U.S. Pat. No. 7,799,553 (Mathies et al.); U.S. Pat. No. 8,173,417 (Tan et al.); U.S. Pat. No. 8,206,974 (Tan et al.); U.S. Pat. No. 8,394,642 (Jovanovich et al.); U.S. Pat. No. 8,425,861 (Selden et al.); U.S. Pat. No. 8,431,340 (Jovanovich et al.); U.S. Pat. No. 8,720,036 (Selden et al.) and U.S. Pat. No. 8,858,770 (Tan et al.); US patent applications 2009/0178934 (Jarvius); 2009/0253181; 2011/0039303 (Jovanovich et al.); 2011/0126911 (Kobrin et al.); 2011/0220502 (Selden et al.); 2012/0181460 (Eberhart et al.); 2013/0139895 (Vangbo) and 2013/0115607 (Nielsen et al.); and International Patent Application WO/US2013/130910.

SUMMARY OF THE INVENTION

Fluidic devices are provided, for example in the form of a cartridge, for sample extraction and analyte reaction and analysis.

Provided herein is a cartridge comprising one or more fluidic circuits that each comprise at least one diaphragm valve; wherein the cartridge comprises: (a) a body comprising (i) a surface comprising a valve seat in fluidic communication with a valve inlet and a valve outlet and (ii) at least one port in fluidic communication with the fluidic circuit; and (b) a layer of deformable material covering the valve seat and the at least one port, wherein a portion of the layer of deformable material functions as a diaphragm which, in combination with the valve seat, forms a diaphragm valve, and wherein the diaphragm, when actuated (for example, by being moved into contact with the valve seat or by being moved out of contact with the valve seat), regulates fluid flow across the diaphragm valve, and comprising at least one conduit through the layer of deformable material, each conduit communicating with a port; and wherein the cartridge is configured to engage a cartridge interface, putting the deformable material in direct contact with a surface of cartridge interface, putting the diaphragm in communication with a source of positive and/or negative pressure that actuates the diaphragm (e.g., pneumatically or mechanically) and putting the at least one port in communication with a fluid or pneumatic line through the conduit, wherein the layer of deformable material optionally functions as a gasket sealing the at least one port against leakage. In one embodiment the fluidic circuit further comprises a reaction chamber formed in the body, optionally covered with a film of heat conductive material (e.g., a metal film). In another embodiment the fluidic circuit further comprises a chamber configured to receive a sample comprising a biological material, said chamber optionally comprising a close tab. An example of such an instrument and cartridge is shown in FIGS. 1-5.

Also provided herein is an instrument comprising: (a) at least one cartridge interface comprising: (i) an engagement unit configured to receive a removably insertable cartridge and to engage a received cartridge with a manifold assembly and, optionally, a thermal regulator, wherein the cartridge comprises at least one fluidic circuit comprising at least one fluid channel, at least one exit port; and at least one diaphragm valve comprising a valve seat configured to regulate fluid flow in the at least one fluidic circuit; and a layer of deformable material covering the valve seat and the at least one port, wherein the deformable material functions as a diaphragm in the diaphragm valve and comprises at least one conduit through the layer, each conduit communicating with a port; and (ii) a manifold assembly comprising an engagement surface configured to directly contact the deformable layer of a received cartridge and having a plurality of transmission channels communicating with ports on the engagement surface; wherein engaging a cartridge with the manifold assembly: (A) puts the diaphragm in communication with a first port on the engagement surface configured to transmit positive or negative pressure to the diaphragm, and (B) puts the exit ports in communication with second ports on the engagement surface configured to transmit fluid into or out of a fluidic circuit through the transmission channels; and (iii) a thermal regulator which, when engaged with a received cartridge, puts a heat pump (e.g., a thermoelectric heater, e.g., a Peltier device) in thermal contact with a thermal cycling chamber in the cartridge or a heating element in thermal contact with a chamber in the cartridge. In one embodiment the instrument of further comprises any of: (b) a pneumatic pressure source configured to deliver positive or negative pneumatic pressure to a transmission channel of the manifold assembly; (c) a pump configured to move liquid into or out of a transmission channel of the manifold assembly; (d) a source of reagents in fluid communication with a transmission channel of the manifold assembly; (e) an analysis module configured to perform at least one analysis (e.g., electrophoresis) on a fluid received from the cartridge; and (f) a control module comprising executable code that, when executed, controls operation of the instrument.

Also provided herein is a cartridge comprising a first layer and a deformable layer: (a) wherein the first layer comprises: (i) a first side contacting the deformable layer, wherein the first side comprises a plurality of fluidic circuits, each fluidic circuit comprising at least one fluidic channel; and (ii) a second side comprising at least one fluidic distribution channel, which fluidic distribution channel is covered by a cover layer; (iii) a plurality of vias in the first layer, each via configured to put the fluidic distribution channel in communication with a fluidic channel; and (iv) optionally, at least one via in the first layer configured to put the fluidic distribution channel in communication with a port on a side of the first layer configured to engage a source of fluid; and (b) optionally comprising an actuation layer comprising at least one actuation circuit configured to actuate a diaphragm against a valve seat in the first side. An example of such a cartridge is shown in FIGS. 6 and 9.

Also provided herein is a cartridge comprising a first layer, a second layer and a deformable layer sandwiched there between: (a) wherein the first layer comprises: (i) a first side contacting the deformable layer, wherein the first side comprises a plurality of fluidic circuits, each fluidic circuit comprising at least one fluidic channel and at least one valve seat; (ii) a second side comprising at least one pneumatic distribution channel, which pneumatic distribution channel is optionally covered by a cover layer; (iii) at least one via in the first layer configured to put a pneumatic distribution channel in communication with the deformable layer; and (iv) optionally, at least one via in the first layer configured to put a pneumatic distribution channel in communication with a port on a side of the first layer configured to engage in a source of pneumatic pressure; (b) wherein portions of the deformable layer, in combination with valve seats in the first layer form diaphragm valves; and (c) wherein the actuation layer comprises at least one actuation circuit comprising at least one branch channel, wherein each branch channel is configured to actuate a diaphragm against a valve seat in a different fluidic circuit and further comprises a valve seat; and wherein positive or negative pressure applied to a pneumatic distribution channel transmits pressure through the via to actuate a diaphragm portion of the deformable layer into or out of contact with the valve seat in the branched channel, wherein closing the control valve inhibits actuation the diaphragm valve in the fluidic circuit. An example of such a configuration is shown in FIG. 10.

Also provided herein is a cartridge comprising: (a) a body comprising a polymer and comprising at least one functional feature on a surface of the body and configured to transmit fluid (e.g., a port, a via, a fluid channel, a chamber, a valve inlet and valve outlet and/or a valve seat); and (b) a layer of deformable material thermally bonded to the body and covering the functional feature (optionally, wherein at least one portion of the layer comprises a permanent deformation), and wherein application of positive or negative pressure to at least one portion of the layer actuates the deformable material into or out of contact with a functional feature on the surface of the body; and wherein the cartridge is configured to engage a cartridge interface configured to supply positive or negative pressure to the at least one portion of the layer. In one embodiment the cartridge further comprises a fluid-filled chamber in the body, wherein the chamber has an opening sealed closed with a heat seal material. In another embodiment the deformable material comprises a heat seal material. In another embodiment the deformable material comprises a material selected from polypropylene, polyethylene, polystyrene, cycloolefin co-polymer (COC), mylar, polyacetate and a metal. An example of valves in such a cartridge is shown in FIGS. 7, 8, 13, and 14 (seal not shown in all figures).

Also provided herein is a device comprising the aforementioned cartridge and a ram configured to actuate a diaphragm of a diaphragm valve on the body.

Also provided herein is a device comprising a cartridge and a clamping device: (a) wherein the cartridge comprises: (i) a body comprising: (A) at least one fluidic circuit comprising: (I) at least one functional feature on a surface of the body and configured to transmit fluid (e.g., a port, a fluid channel, a chamber, a valve inlet and valve outlet and/or a valve seat), wherein the functional feature optionally comprises a ridge on the surface of the body; and (II) at least one compartment containing a liquid, wherein the compartment communicates with the functional feature through one or more vias in the body; and (ii) a layer of deformable material covering the functional feature; and (b) wherein the clamping device, when engaged with the cartridge, applies sufficient pressure to the deformable material to deform the deformable material against the cartridge body and seal against movement of liquid from the compartment and through the at least one functional feature; and wherein removing the clamping device releases pressure to the deformable material, allowing the seal to open (e.g., through an elastic response of the deformable material or through application of positive or negative pressure against the seal). In one embodiment the clamping device comprises a mechanical clamp or a vacuum seal. An example of such a cartridge is shown in FIGS. 6 and 11.

Also provided herein is a cartridge comprising: (a) a fluidics layer comprising a surface having at least one diaphragm valve comprising a valve seat (e.g., a recessed valve seat); (b) a deformable layer mated to the surface, wherein a portion of the deformable layer functions as a diaphragm which, when actuated, is configured to move into or out of contact with the valve seat; and wherein the portion of the deformable layer functioning as a diaphragm comprises a boss positioned on a side of the deformable layer opposite of a side that contacts the valve seat; and (c) optionally comprising: a rigid substrate mated with the deformable layer and comprising apertures exposing the bosses and configured to receive a ram that contacts the boss and actuates the diaphragm, e.g., by application of mechanical pressure; or configured to engage an interface comprising apertures exposing the bosses and configured to receive a ram that contacts the boss and actuates the diaphragm, e.g., by application of mechanical pressure. An example of such a cartridge is shown in FIGS. 15 A and B.

Also provided herein is a cartridge comprising: (a) a base comprising: (I) a central barrel comprising a pump chamber and movable syringe, (II) a base floor comprising a port station comprising a floor port; and (III) a channel fluidically connecting the barrel chamber to the port in the floor; and (b) a turret configured to revolve around the central barrel and comprising a plurality of turret chambers, each turret chamber comprising a turret chamber aperture in a chamber floor of the turret chamber and facing the base floor, wherein positioning a turret chamber at the port station puts the turret chamber aperture in fluid communication with the barrel chamber through the floor port, and wherein the floor closes a turret chamber aperture when the turret chamber is positioned at at least one position other than the port station; and wherein at least one turret chamber further comprises a channel communicating between the floor port and an exit port. An example of such a cartridge is shown in FIG. 17.

Also provided herein is a instrument comprising a cartridge interface and a removable cartridge engaged therewith: (a) wherein the interface comprises a base and one or more hollow bore pins for delivering fluid to a port in the cartridge, wherein the pin is biased against the base by the cartridge and protrudes through an aperture in the base; and wherein the pin comprises a home lead-in configured to put the pin in a home position after the bias is released by removal of the cartridge; and a tapered end configured to mate with a guide in the cartridge; and (b) wherein the cartridge comprises a fluidic circuit comprising a port and a pin guide communicating with the port, wherein the pin guide comprises a mating cone configured to mate with a tapered end of the pin and a pin guide lead-in configured to guide the pin into the mating cone when the cartridge exerts a bias against the tapered end of the pin during engagement with the interface. An example of such a combination is shown in FIG. 18.

Also provided herein is a cartridge comprising: (a) a body comprising at least one puncturing element, at least one fluidic channel and at least one flange; and (b) a reagent reservoir comprising at least one fluidically isolated, fluid filled compartment; a breakable seal in a wall of the compartment and a breakable tab attached to an outside wall of the compartment; wherein the cartridge is configured such that when the reagent reservoir is engaged with the body: (i) the puncturing elements punctures the breakable seal, putting the compartment in fluidic communication with the channel; and (ii) the flange exerts a force against the breakable tab, breaking the tab and forming a vent in the compartment. An example of such an embodiment is shown in FIG. 12.

Also provided herein is a fluidic device comprising one or more diaphragm valves, each diaphragm valve configured to regulate fluid flow in a fluidic channel, wherein the fluidic device comprises a fluidics layer, an actuation element and a deformable membrane, wherein each diaphragm valve comprises: a) a diaphragm comprised in the deformable membrane; b) a valve seat comprised in the fluidics layer and recessed from a surface of the fluidics layer that contacts the deformable membrane so that the diaphragm does not close the diaphragm valve unless positive pressure is exerted on the diaphragm; and c) a valve inlet and a valve outlet comprised in the fluidics layer and in fluid communication with a fluidic channel; and d) a ram configured to actuate the diaphragm; wherein the deformable membrane comprises a plastic material adhered to the fluidics layer through a heat activated adhesive, thermal fusion, chemical bonding or a pressure sensitive adhesive, and wherein the deformable membrane is configured such that pressure on the deformable membrane presses the membrane against the valve seat, thereby closing the valve and wherein the valve can be opened by releasing pressure of the ram against the deformable membrane or by pushing liquid through the valve. In one embodiment the deformable membrane is not an elastomeric material, e.g., is not PDMS. In another embodiment the deformable membrane comprises a laminate comprising the plastic material and a deformable, space-filling material, wherein pressure against the space-filling material causes the space filling material to fill the valve chamber sufficiently so that of the plastic material closes the valve. In another embodiment the deformable material has a durometer value of between 10 to 80 Shore D. In another embodiment the deformable material has a thickness sufficient such that the mechanical pressure is applied the deformable material sufficiently fills the valve chamber to form a seal between the plastic material in a valve seat to close the valve. In another embodiment the deformable, space-filling material comprises a solid foam. In another embodiment the deformable material is attached to the plastic material through an adhesive. In another embodiment the deformable material is pressed into contact with the plastic layer through an interface device. In another embodiment the fluidics layer comprises a polymer, e.g. a thermoplastic.

Also provided herein is a fluidic device comprising one or more diaphragm valves, each diaphragm valve configured to regulate fluid flow one or more fluidic channels, wherein the fluidic device comprises a fluidics layer, an actuation element and a deformable membrane, wherein each diaphragm valve comprises: a) a diaphragm comprised in the deformable membrane; b) a valve seat comprised in the fluidics layer and recessed from a surface of the fluidics layer that contacts the deformable membrane so that the diaphragm does not close the diaphragm valve unless positive pressure is exerted on the diaphragm; and c) a valve inlet and a valve outlet comprised in the fluidics layer and in fluid communication with a fluidic channel; and d) a ram comprised as an actuation element having a forked end comprising tines, wherein the end has a surface complying with the valve seat and wherein the tines are compliant to lateral pressure whereby pressure by the ram on the diaphragm and against the valve seat closes the valve. Embodiments are shown in FIGS. 29-32.

Also provided herein is a fluidic device comprising a sample input, a sample output and a waste chamber, all fluidically connected through fluid channels wherein the waste chamber comprises a material that degrades nucleic acid. In one embodiment the material that degrades nucleic acid comprises a hypochlorite salt. In another embodiment the material that degrades nucleic acid comprises an enzyme such as an exonuclease or an endonuclease.

Also provided herein is a fluidic device comprising a fluidic circuit comprising sample input, a reaction chamber and a sample output, wherein the reaction chamber comprises a solid substrate, e.g., solid phase extraction material, for retaining analyte from a sample. In one embodiment the solid substrate comprises a material that binds nucleic acid. In another embodiment the solid substrate comprises Whatman FTA paper, a carboxylated material, a sponge-like material, a polymer membrane, or glass particles. In another embodiment the solid substrate binds a predetermined amount of material. Embodiments are shown in FIGS. 22-28.

Also provided herein is a method comprising 1. A method comprising: (a) providing a reaction mixture comprising: (I) a sample comprising mammalian (e.g., human) DNA, (II) reagents for amplifying short tandem repeats (STRs) in the mammalian DNA (e.g., labeled primers, nucleotides and polymerase) and (III) a mammalian-specific probe selected to be amplified in the reaction and including a label that is distinguishable from the labeled primers; (b) performing an STR reaction comprising amplifying STRs in the sample and the mammalian specific probe; (c) detecting an amount of amplified mammalian specific probe in the reaction, e.g., over time, e.g. performing real-time PCR; and (d) optionally, stopping the STR reaction based on the amount of amplified mammalian specific probe detected. In one embodiment the labels are fluorescent labels and the distinguishable label has a wavelength above or below the highest or lowest wavelength of labeled primers. In another embodiment the mammalian specific probe further comprises a quencher such as a Black Hole Quencher® or a TaqMan® probe.

INCORPORATION BY REFERENCE

All publications and patent applications mentioned in this specification are herein incorporated by reference to the same extent as if each individual publication or patent application was specifically and individually indicated to be incorporated by reference.

BRIEF DESCRIPTION OF THE DRAWINGS

The novel features of the disclosure are set forth with particularity in the appended claims. A better understanding of the features and advantages of the present disclosure will be obtained by reference to the following detailed description that sets forth illustrative claims, in which the principles of the disclosure are utilized, and the accompanying drawings of which:

FIG. 10A shows an exploded view of the cartridge. FIG. 10B shows an exploded view in clamshell format. The cartridge comprises a fluidics layer 1001, pneumatic layer 1003 and an deformable layer 1005 sandwiched between them. Fluidics layer 1001 includes at least one fluidic channel 1007 that includes recessed valve seat 1009. The fluidics layer also comprises a control line 1011 having a branch 1013 that communicates through a via 1015 with a surface of the fluidics layer mated with the deformable layer. The pneumatic layer comprises a pneumatic channel 1017 comprising one or more branches 1019. Each branch controls one diaphragm valve. The branch includes a valve relief 1021 positioned on the deformable layer opposite the valve seat in the fluidics layer into which the deformable layer can be deformed and which can transmit pressure to the diaphragm, actuating the diaphragm into the valve seat 1009. The branch also comprises a valve seat 1023 positioned opposite via 1015, which via connects to pneumatic control line 1011. Assertion of positive or negative pressure against control line 1011 to the diaphragm actuates the diaphragm against or away from the valve seat 1023 in the pneumatic layer. When pressed against the valve seat, this prevents transmission of pressure through pneumatic actuation channel 1017, rendering the diaphragm valve 1009 that controls fluid in fluidic line 1007 inoperative.

DETAILED DESCRIPTION OF THE INVENTION

I. Instruments for Engaging and Operating Fluidic Cartridges

In one aspect provided herein is a cartridge comprising: (a) a body comprising a fluidic circuit comprising: (1) a sample chamber comprising an opening configured to receive a sample and a via through the body; (2) a reaction chamber; (3) diaphragm valve elements including a valve inlet and a valve outlet, each configured as a via through the body, and a valve seat; (4) a plurality of ports through the body; and (5) one or more fluidic channels in a surface of the body, wherein the one or more fluidic channels put the sample chamber (e.g., through the via), the reaction chamber, the valve elements (e.g., through the valve inlet and valve outlet), and each of the plurality of ports in fluidic communication with each other; (b) a cover layer attached to the body and sealing the via, the fluidic channels and the reaction chamber; and (c) a deformable layer attached to the body, wherein the deformable layer (i) comprises a plurality of holes, each hole communicating with a port; and (ii) in combination with the valve inlet, the valve outlet and the valve seat, form a diaphragm valve configured to regulate fluid flow in the fluidic circuit.

In another aspect provided herein is an instrument comprising: (a) at least one cartridge interface comprising: (1) an engagement assembly having a first position to receive a cartridge as described herein and a second position to engage a received cartridge with a manifold assembly and an optional thermal regulator; (2) a manifold assembly having a plurality of channels, each channel opening onto a front port and a back port, wherein, when the engagement assembly has received a cartridge and is in the second position, a plurality of front ports fluidically engage ports in the cartridge and pneumatically engage the diaphragm of the diaphragm valve, and wherein the deformable material serves as a gasket for fluidic engagement; (3) an optional thermal control assembly (e.g., thermal cycler) configured to place a heat spreader in thermal contact with a thermal cycling chamber of an engaged cartridge and to regulate temperature of the thermal cycling chamber, when the engagement assembly is the second position; (b) a pneumatic and fluidic assembly comprising: (1) a source of pneumatic pressure; (2) a plurality of fluid sources; (3) a plurality of transmission lines connecting a source of pneumatic pressure in each of the plurality of sources in fluid communication with a back port of the manifold assembly; (4) a pump configured to move fluids from the source through the transmission lines.

Figure 1:
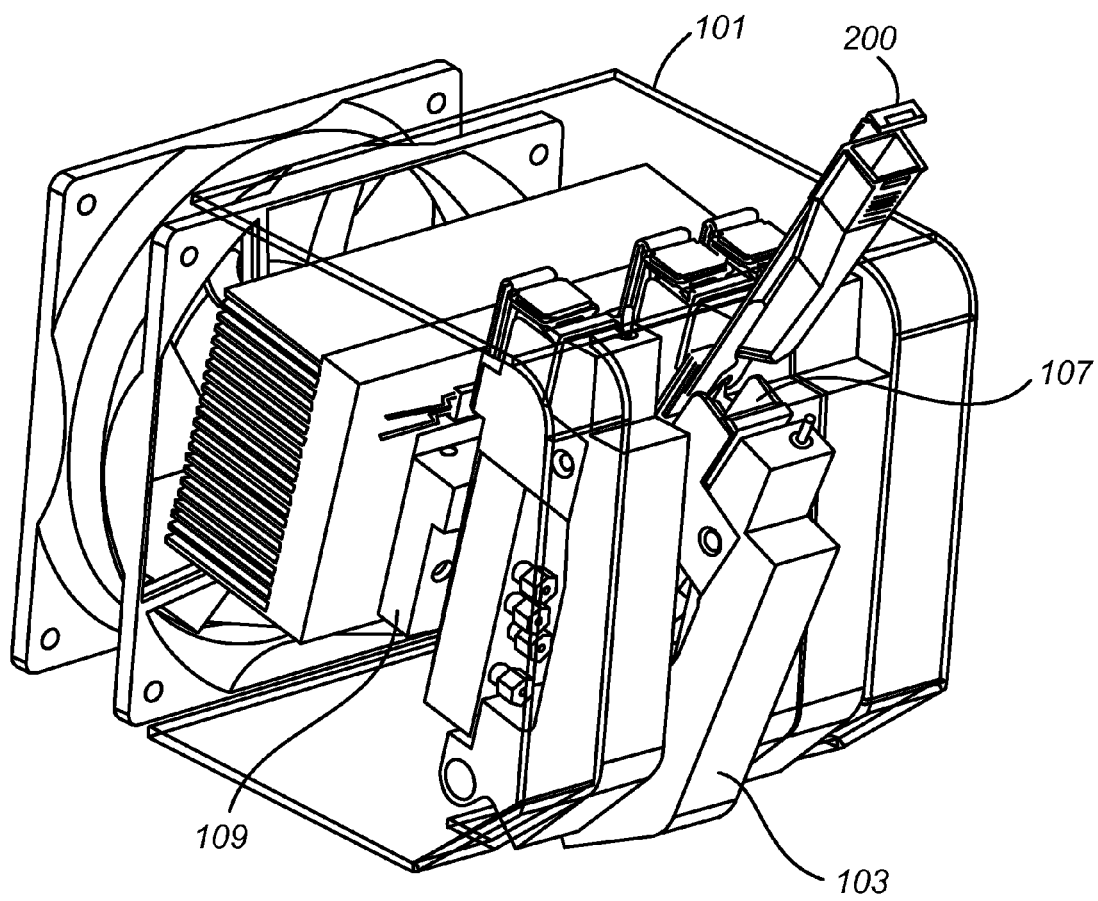
FIG. 1 shows an instrument 101 comprising an interface adapted to engage a cartridge, including a cartridge interface 103 and a cartridge 200 inserted into a slot 107. The embodiment shown contains four cartridge-receiving sub-assemblies and Peltier device 109.
Figure 4:
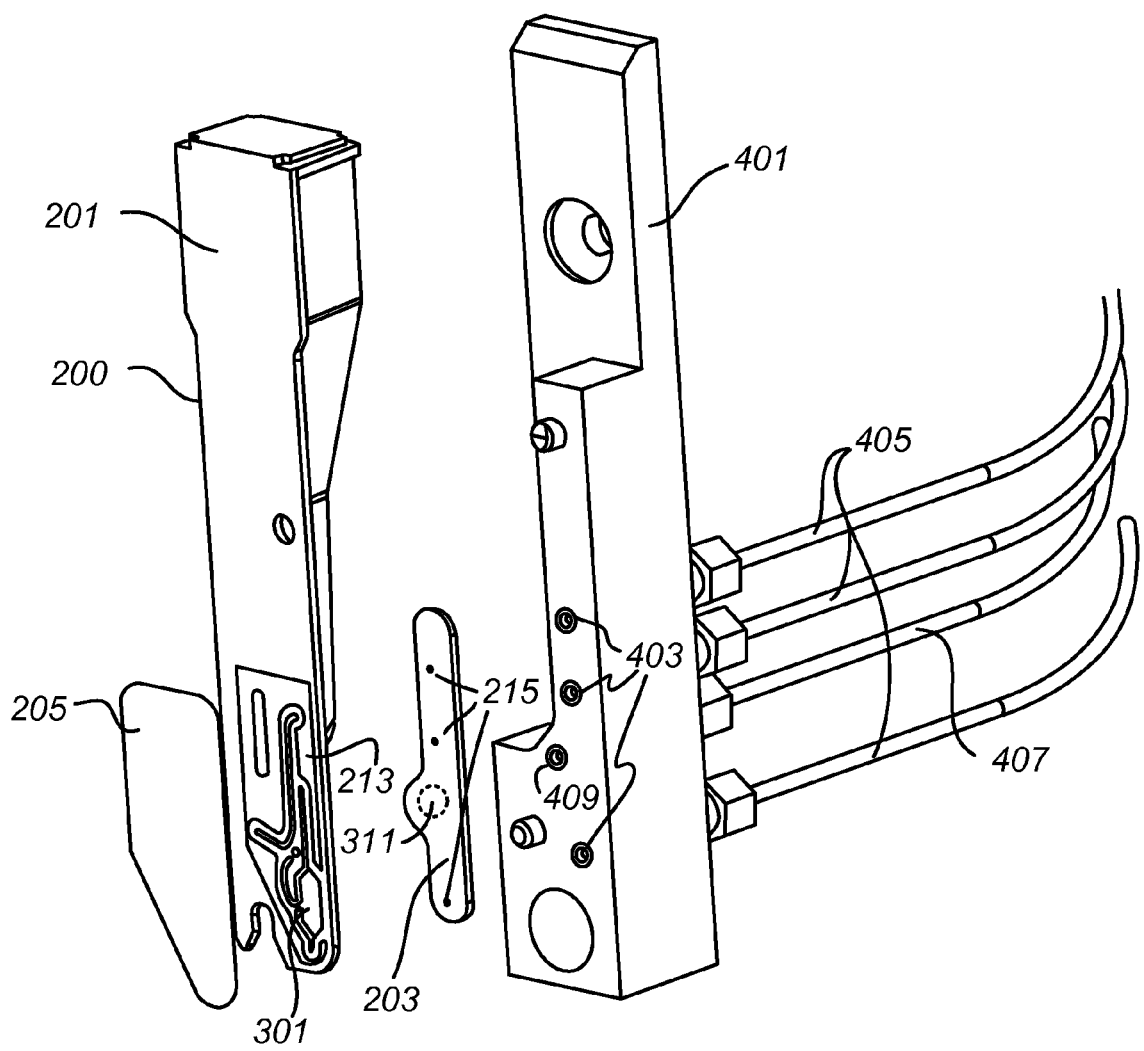
FIG. 4 shows from one aspect an exploded view of a cartridge 200 and an assembly 401 of a cartridge interface. The cartridge includes body 201, cover sheet 205, and deformable layer 203. The body includes, on one side, fluidic channel 213 and reaction chamber 301. Fluidic channels communicate through apertures in body 201 with a face covered by deformable layer 203. The deformable layer 203 includes ports 215 configured to align with ports 403 on the interface assembly 401 and an area 311 positioned to function as a diaphragm in a diaphragm valve. Fluidic lines 405 connect to interface assembly 401 and transmit fluids to port 403 which connects to cartridge 201. Pneumatic line 407 also connects to interface assembly 401 and transmits positive or negative pneumatic pressure to port 409 which actuates diaphragm for 311.
Figure 5:
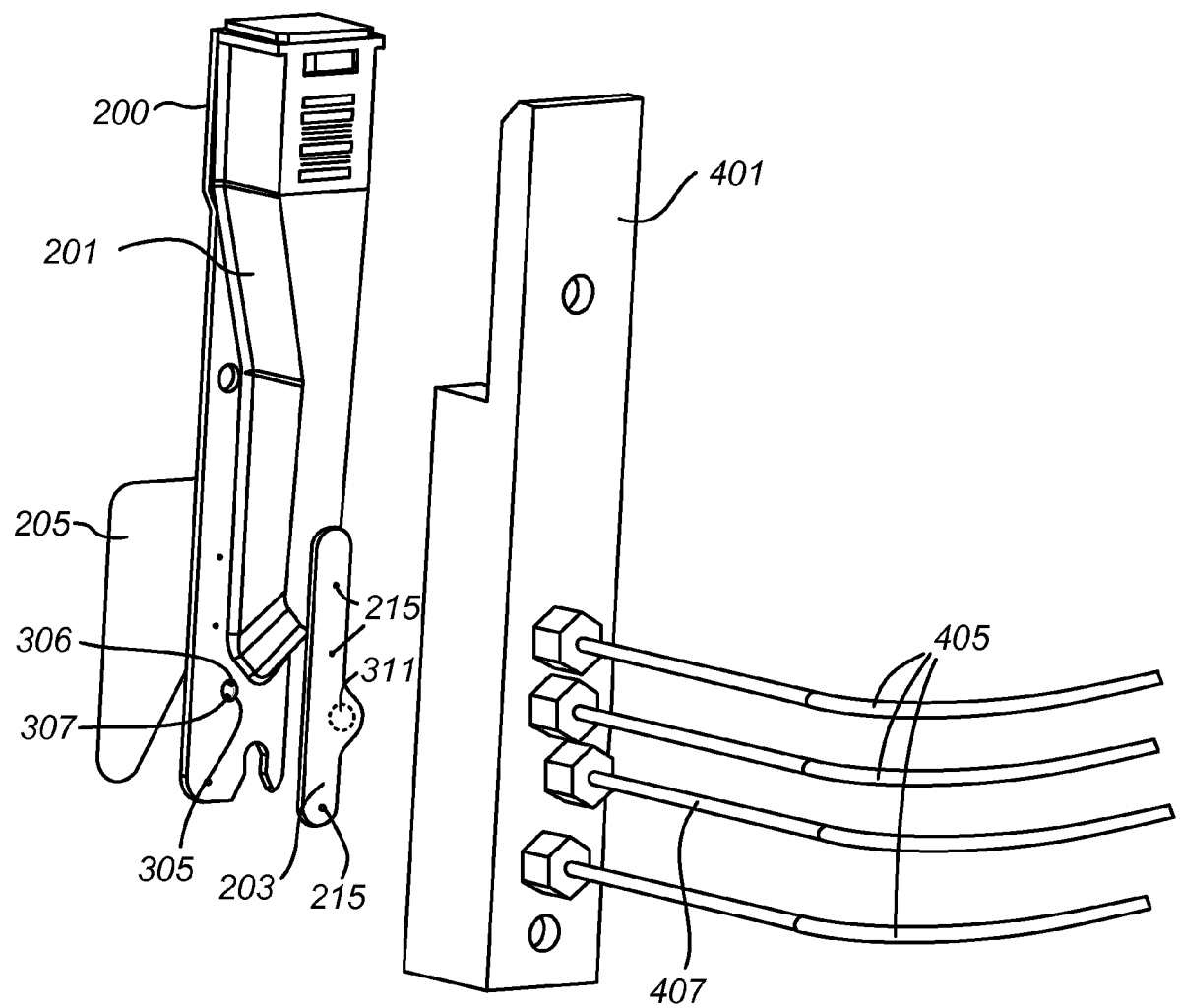
FIG. 5 shows from another aspect an exploded view of a cartridge of this disclosure and an assembly 401 of a cartridge interface. Body 201 includes a valve body with valve seat 305 with apertures 306 and 307 which is covered by deformable layer 203. Interface assembly (401) includes pneumatic line 407 that, when engaged with deformable layer 203, transmits positive or negative pressure to actuate diaphragm 311. Interface assembly 401 also includes fluid lines 405 communicating through passages in interface 401 with apertures 215 in the deformable layer 203 to allow movement of fluids into, through an out of fluidic circuits in the cartridge.

FIG. 1 shows an interface configured for a cartridge. Referring to FIGS. 4 and 5, for a single sample cartridge, the interface may also include three fluidic connections 405 and one pneumatic connection 407 to control the valve. These can be low-dead-volume connections which connect to the pneumatic and fluidic assembly through tubes. Alternatively, they can be rams such as pogo pins (e.g., 1801 of FIG. 18).

This configuration permits samples to be inserted into cartridges, and cartridges to be independently inserted into a slot, even if other slots are processing other samples. Thus, in one embodiment, the system can process samples independently.

The cartridge described in FIGS. 1-5 minimizes the cost of manufacture by minimizing the functions that need to be handled by the disposable cartridge. These functions are moved onto a pneumatic and fluidic assembly, which can be a permanent or semi-permanent part of the system.

In this embodiment, the cartridge can comprise an injection molded body, for example, a plastic, a deformable film; and a foil, such as a metal foil, each bonded to the body. The body can have integrated alignment features 209 and 225 so that it can be easily and accurately inserted into the interface. The plastic material can include any plastic known to those skilled in the art, such as polypropylene, polystyrene, polyethylene, polyethylene terephthalate, polyester, polyamide, poly(vinylchloride), polycarbonate, polyurethane, polyvinylidene chloride, cyclic olefin copolymer (COC), or any combination thereof.

The cartridge may be scribed with a barcode or QR code for optical identification or have an EEPROM or RFID or other similar identification device mounted on the cartridge that can assist in sample tracking and optionally contain information about the chemistry, process to be performed, lot number, expiration date, and other information.

The body can have a folding tab 211 that can be snapped shut after the swab is inserted, either by the operator or the system. More than one style of body, each adapted to a swab, punch type, or sample type can be produced. After the tab is snapped shut, the body can serve to contain the sample, providing protection against contamination and facilitating re-testing or recovery of the sample as required.

The body can also define the volumes for two process chambers. The swab, punch, or other sample type is placed in a compartment 207 that also serves as a lysis chamber. To accommodate the swab, punch, or other sample type, it can have a volume ranging from, e.g., 10 µL to 15 mL or 1 ml to 10 ml. Cells are lysed and DNA extracted from the swab, punch, or other sample type in this chamber. The second chamber 301, called the reaction chamber, can serve to capture DNA or house a small amount of lysate for direct amplification. It can also be where cleanup and/or amplification occurs. To minimize the duration of thermocycling and the amount of energy required, this second chamber can have minimal volume, perhaps ranging from 2 µl to 25 µl, although other configurations are practical.

Figure 2:
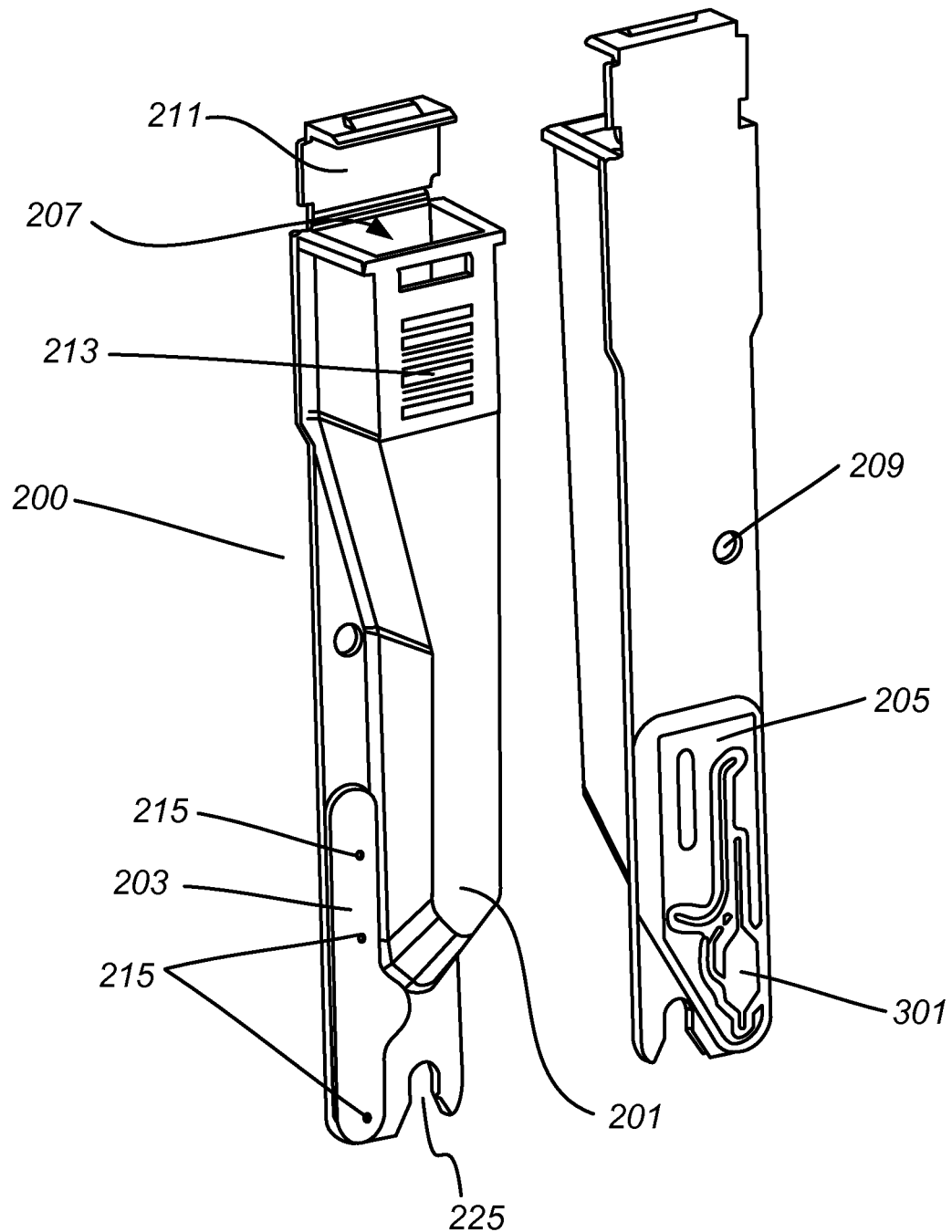
FIG. 2 shows cartridge 200, which is insertable into instrument 101. The cartridge includes a body 201. It further includes elastic layer 203 attached to a surface of the body. Layer 203 provides a diaphragm for a diaphragm valve on a surface of body 201, as well as ports 215 communicating with fluidic channels in body 201. The cartridge also includes cover sheet 205 that seals a chamber in the body and/or functions to transmit heat to or from the chamber. For example, when the cartridge is engaged with the interface, the chamber can function as a thermal cycling chamber and cover sheet 205 can be in contact with a source of thermal energy, such as a Peltier device 109. The cartridge also includes a slot 207 adapted for receiving a sample. Aperture 209 and notch 225 are alignment features configured to align cartridge 200 with cartridge interface 103. The cartridge also includes a closable cap 211.
Figure 3:
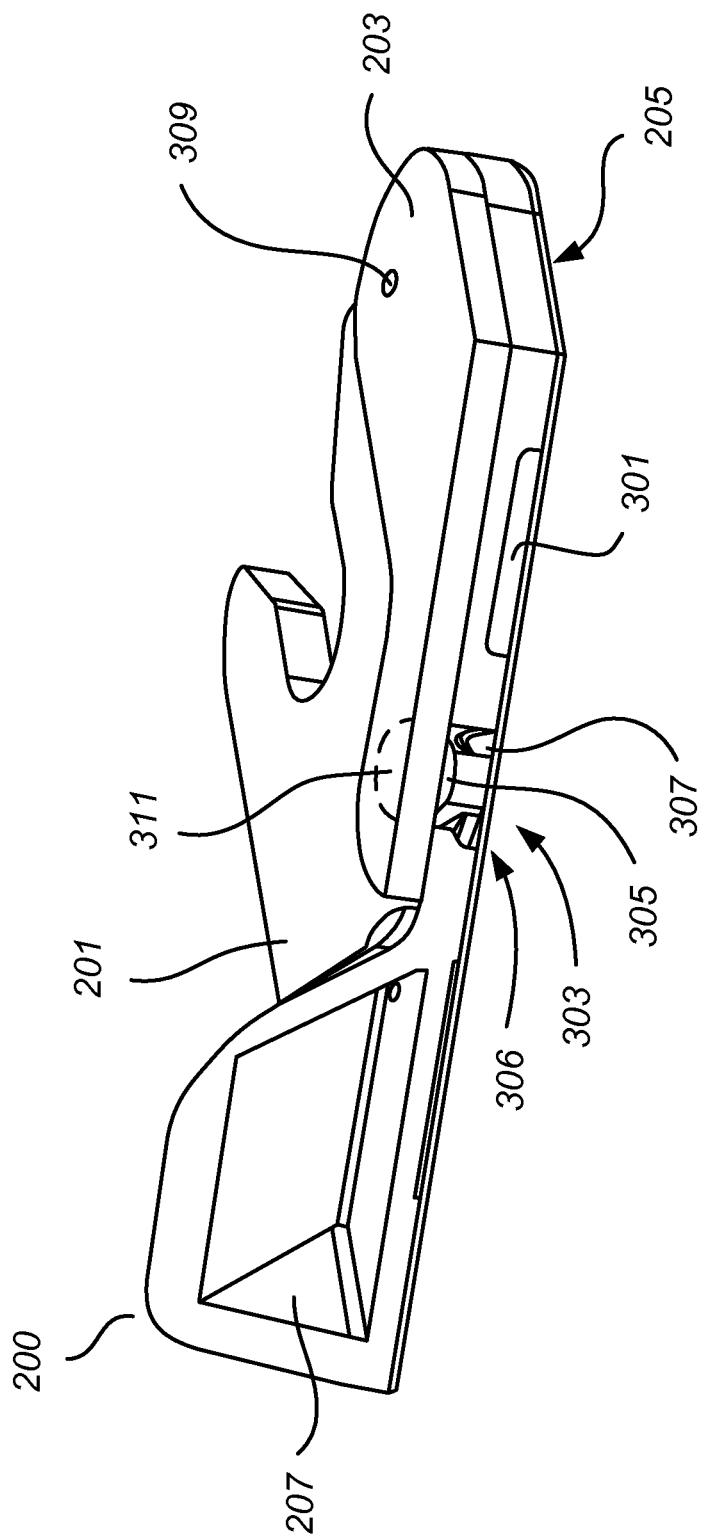
FIG. 3 shows a cutaway view of cartridge 200. Reaction chamber 301 is in thermal contact with the cover sheet 205 which can be sealed to the body. Cartridge 200 includes diaphragm valve 303. Diaphragm valve 303 includes recessed valve seat 305 defining a valve chamber. Valve inlet 306 and valve outlet 307 are configured as vias through body 201 and communicate with fluidic channels in the body. Deformable layer 203 includes a portion functioning as a diaphragm 311. Putting diaphragm 311 into contact with valve seat 305 closes diaphragm valve 303. Deformable layer 203 also comprises port 309 that communicates with a fluidic conduit in the cartridge. When the cartridge is engaged with a cartridge interface, deformable layer 203 functions as a gasket that seals around port 309.

Referring to FIGS. 2 and 3, to an area of the cartridge body 201, a deformable film 203 can be bonded on one side, and a cover sheet 205, such as a plastic film or metal foil, can be bonded to the other.

The deformable material used in cartridges disclosed herein can be a plastic material (plastic deformation) or an elastic material (elastic deformation). The plastic material can comprise, without limitation, a polymer or a metal. Suitable plastic materials include, without limitation, polypropylene and polyethylene. Suitable metals include aluminum. Suitable elastic materials include, for example, elastomeric materials such a polysiloxanes, e.g., PDMS. Other deformable materials are further described herein.

In one embodiment, the deformable film serves as a gasket for three low-dead-volume connections. These provide an inlet, an outlet, and a purge line that can be used to flush out the cartridge and outlet line. The deformable film also serves as the flexible diaphragm for a valve. The valve seat 305 can be formed into the cartridge body. The inputs 306 and outputs 307 to the valve can be vias through the body, channels between the body and the deformable, or both.

The valve can be actuated by positive or negative pressure or applied to the deformable material over the valve seat. In another embodiment the valve can be actuated by a ram exerting mechanical force on cover sheet 205.

The deformable material may also fill a hole in the body, creating a flexible valve on the far side of the body. The deformable material can be pressed from the near side to deform through the body, and seal against a surface on the far side of the body.

In addition to being mechanically simple, structuring the cartridge around one molded body with functional elements on the surface increases the robustness. Leaks are critical problems, so the fluidic and pneumatic connections need to line up to enable sealing. Tolerance variations accumulate across assemblies, typically with each part contributing some variation. As a result, simpler assemblies can be more robust even with the same part tolerances. Furthermore, the single sample cartridge and other simplified cartridges in this instant disclosure involve only a few connections, further reducing the risk of leakage. Additionally, the effect of thermal expansion increases with size, so having few connections that are also close together reduces the risks still more.

This embodiment integrates parts, reducing materials and assembly costs. In one embodiment, it is designed with pneumatic ports, fluidic ports, and valve controls (either mechanical or pneumatic) onto one side. This simplifies connections and permits more space for other functions such as a temperature regulator (e.g., a thermocycler) to contact the cartridge, an optical system to interrogate the cartridge, or other measurement devices.

Figure 16A:
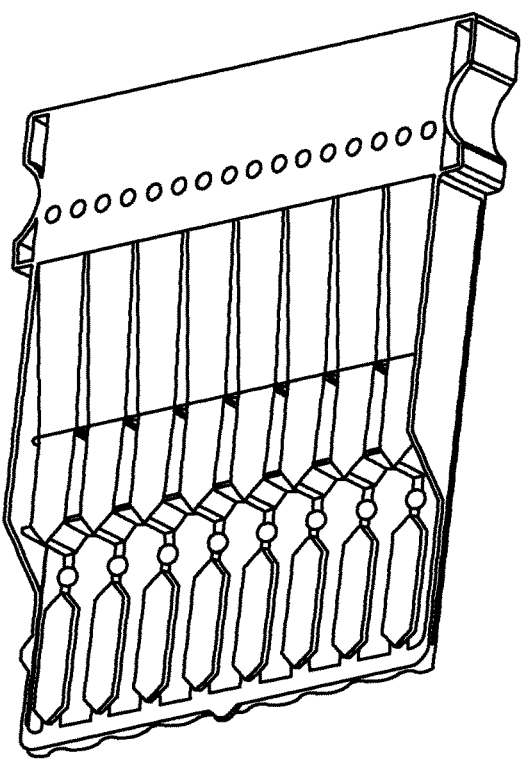
FIGS. 16A and 16B show, respectively, a front and back view of a multi-sample cartridge.
Figure 16B:
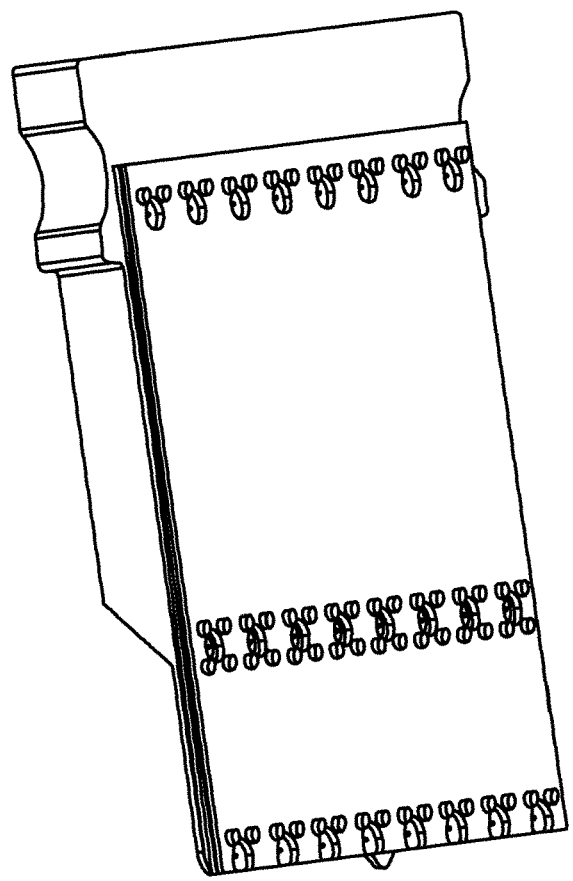

Cartridges constructed in this or other embodiments can also be built to accommodate multiple samples. These multi-sample cartridges can permit the operator to run multiple samples without having to insert multiple cartridges. (See, e.g., FIGS. 6 and 16)

Alternatively, single-sample cartridges can be assembled onto multi-cartridge holders. Operators running many samples at a time are able to take the rack containing used cartridges out of the system and insert the new rack containing unused cartridges. Operators running only a few samples are able to populate only as many spaces as they wish. The remaining spaces can be filled with dummy cartridges or left empty depending on the configuration.

The single-sample cartridges become particularly advantageous when paired with a latched cartridge interface 101 that can permit them to be inserted and removed singly. This can provide more flexible sample flow.

This interface can have a number of cartridge positions 103 or 'slots' that can open and close independently. They can apply a compressive force on the cartridges. They can be held closed by solenoids, or another means controlled by the software, or could be manually latched.

An operator with a new sample to run can insert the sample into a cartridge, and snap the cartridge top closed. He or she can then ask the system to open a slot. If a slot is not in use, the system opens it, permitting the sample to be inserted. If a processed cartridge is in the slot, the operator removes it. The operator could read the barcode, QR code, RFID or other identifying material on the cartridge before it is inserted or the system could read as it is inserted or afterwards. The operator can then push the interface closed, and enter additional information if necessary. The system can then start processing the sample immediately or start it automatically when next possible.

In an alternative embodiment, an operator with a new sample can manually open a slot or direct the system to open a slot. If a slot is not in use, the system opens it. If a processed cartridge is in the slot, the operator removes it. The operator inserts a cartridge. The operator could read the barcode, QR code, RFID or other identifying material on the cartridge before it is inserted or the system could read as it is inserted. The operator could then read the barcode, QR code, RFID or other identifying material on the sample if there is one and place the sample into the cartridge in the slot; alternatively the operator could enter sample tracking information manually into the system. After the sample has been added, the top of the cartridge can be closed by the operator or by the instrument. The operator can then push the interface closed manually or the instrument can close the interface. The system can then start processing the sample immediately or start it automatically when next possible.

This instant embodiment can be automated with a loading system that automatically inserts and removes cartridges as needed into slots. The automation can include mechanisms to load samples from a variety of sample types such as a collection of tubes containing swabs, microtiter plates containing liquid samples that can include preprocessing from single sources or mixtures, tubes containing liquid samples that can include preprocessing from single sources or mixtures, blood containers such as Vacutainers, or other containers for additional sample types.

The interface for each cartridge can float, permitting it to seal around the various fluidic and pneumatic connections on one side, while pressing the cartridge against the thermo regulator (e.g., thermocycler) 109 on the other. As shown, the floating interface rotates, pressing the cartridge against a fixed temperature regulator. Alternatively, multiple smaller thermocyclers could be used. These can rotate or translate, possibly pressing the cartridges against a common pneumatic and fluidic assembly.

After processing, the slot may remain closed to avoid contamination.

The interface can press the cartridge against a temperature regulator, e.g., a Peltier device. This contact can be against the foil or film 205 enclosing the reaction chamber. Depending on the chemistry used, on the opposite side of the reaction chamber, the interface can house an LED, filter, and photodiode for reaction quantification or another detector.

In such an embodiment, when the reaction is a short tandem repeat (STR) reaction, in many jurisdictions for casework samples, the amount of human DNA must be quantified. The typical forensic process is to quantify an extracted sample using real time polymerase chain reaction (PCR) in a separate instrument before the sample is STR amplified. In this instant disclosure, a human specific probe is added to the STR mixture which has fluorescence outside the range used by the STR kit. The reaction chamber 301 is interrogated by a suitable wavelength of light for the human specific probe while the STR is being PCR amplified. The human specific probe can be a quencher such as a Black Hole Quencher® or a TaqMan® probe or other chemistries well know to one skilled in the art. As the PCR cycles increase, the fluorescence from the human specific probe is monitored to quantify the amount of human DNA in the reaction. In a preferred embodiment, the number of amplification cycles can be adjusted based upon the amount of human DNA measured; this can be on a cartridge-by-cartridge monitoring if independent thermal cyclers are in use. One advantage is that the human specific probe will allow the concurrent STR amplification to achieve an optimal amplification and produce an amount of STR product that is optimal for the kit regardless of amount of starting DNA in the sample. A second advantage is the real monitoring concurrent with the STR amplification allows integration of a sample-to-answer system without having an additional separate quantification process. A third advantage is for low copy number samples where there is barely enough sample to produce a good STR profile the integration of the quantification with the STR amplification prevents the aliquot typically used for quantification from causing the remaining sample to not have enough DNA for a successful STR amplification.

Figure 19:
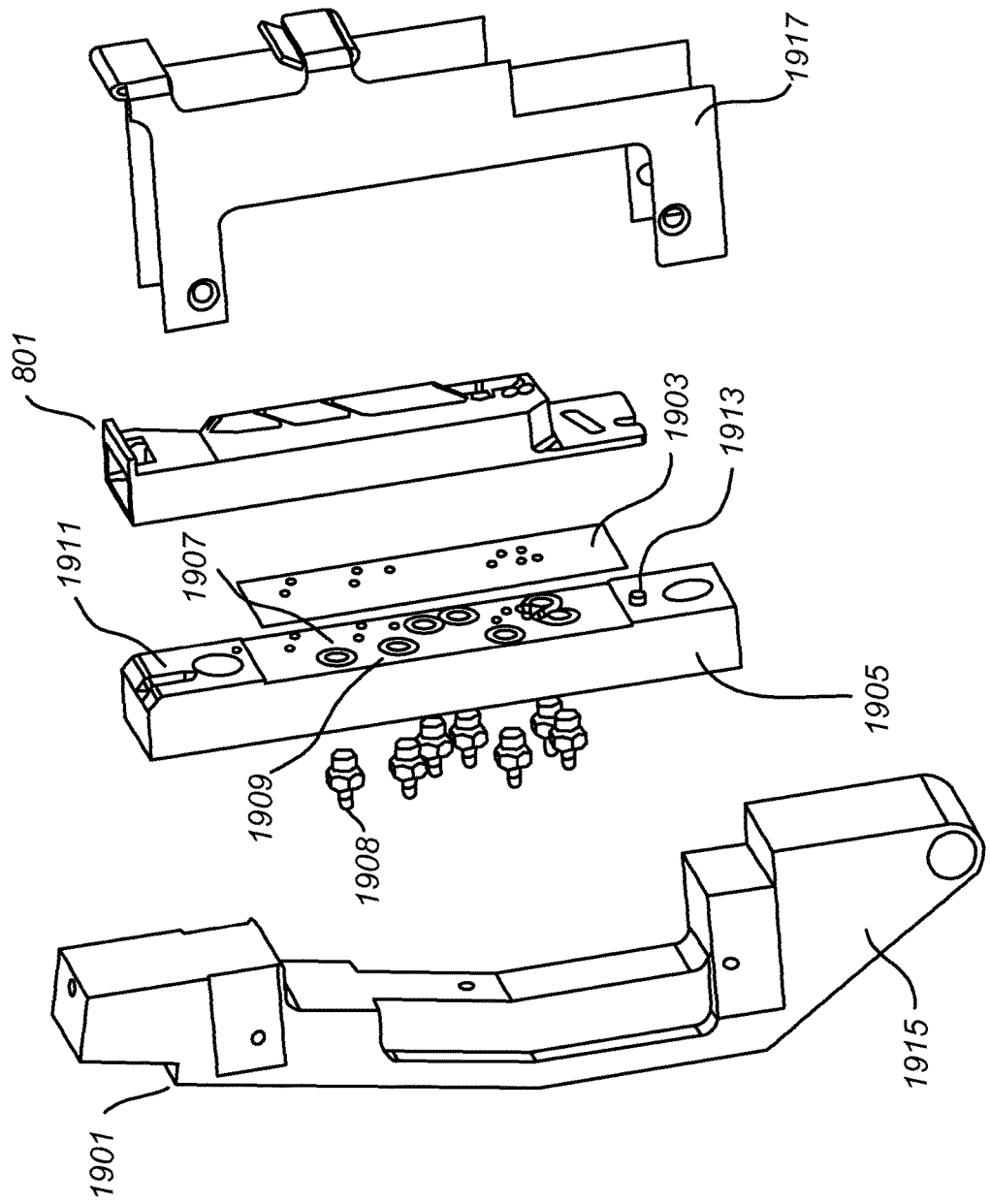
FIG. 19 shows an exploded view of an interface slot.
Figure 20:
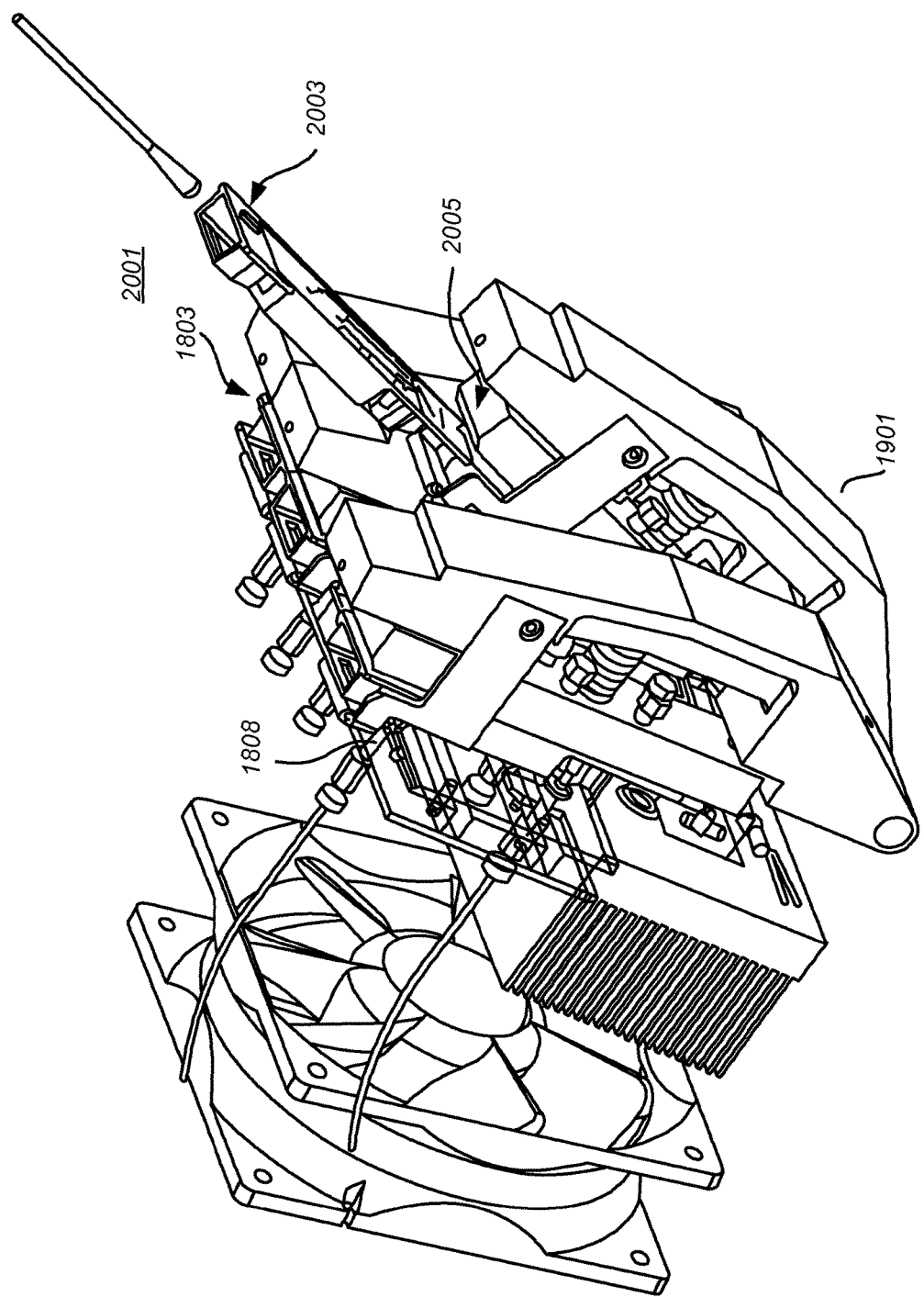
FIG. 20 shows a cartridge interface 1901.

In addition to actuating the valve diaphragms (e.g., 311, 1301) mechanically, they can be actuated pneumatically. In one embodiment, the interface 1901 (FIG. 19) provides, for each valve, an interface diaphragm 1903 that conveys a pressure to the cartridge diaphragm 1301, pushing it against the valve seat 1317 to close the valve. The interface diaphragm is bonded to the interface block 1905 and encloses a threaded hole 1907 with a fitting 1908 to connect to the flexible tube carrying the pneumatic signal. Each hole can correspond to a valve, which it can close or permit to open, controlled by the pneumatic signal. The interface diaphragm may be silicone rubber bonded with RTV, with rings 1909 to limit delamination from fatigue. However, other deformable materials can be used.

The interface block 1905 is a component in the interface latch subassembly 1901. The block has alignment features 1911 and 1913 that mate to the cartridge alignment features 2003 and 2005 accurately locating the cartridge in the interface. The block mounts flexibly to a hinge arm 1915 that pivots to engage the cartridge to the interface, or permit the operator to insert or remove cartridges. A frame 1917 loosely guides the cartridge during insertion, ensuring that it can mate with the alignment features.

The single body cartridge allows on-chip storage/integration of reagent reservoir, including, for example, for example, capillary electrophoresis separation gel. This embodiment also permits STR manipulation without having reagents contact PDMS, which can interfere with certain biochemical reactions. This embodiment permits an integrated reaction chamber: The reaction chamber volume is defined by the outside of the fluidic layer and enclosed (e.g., by heat seal plastic, heat seal foil, graphite, etc). It can connect to the circuit either by vias through the fluidics layer, or by enclosed channels along the surface.

In systems that use STR components that are sensitive to PDMS or other diaphragm materials, the second side can house the STR components in reservoirs 603 (FIG. 6) and use reaction chambers 605 separate from the PDMS layer 909. To improve room-temperature stability, the STR components can be stored separately. Vias through the fluidics layer may push or pull the STR components into the reaction chamber, without having the bulk of the STR mixture contact the PDMS or other membranes.

In addition to STR components, other reagents can also be stored on the second side of the fluidics layer. For laminated cartridges, which need to maintain a high degree of flatness near the pneumatic and fluidic circuits, these storage chambers could be above or below the laminate, or off to the side. The storage volumes would need vents near the top, and outlets near the bottom or narrowed sections capable of drawing the fluids upwards like a straw.

To minimize the risk of contamination from one sample to another, reagents that are used before amplification could have separate chambers above the laminated area. Reagents used after amplification, when contamination is less of a risk, can be shared among all sample circuits. This approach permits all reagents needed to run the system to be stored on a single cartridge.

Those reagents which require low pressures for movement or containment can be handled with diaphragm valves. Those reagents which require higher pressures, such as the separation gel, can be drawn out at low pressure into another chamber, and then pushed into the capillaries at high pressure.

II. Cartridges Having a Fluid Distribution Channel

Figure 6:
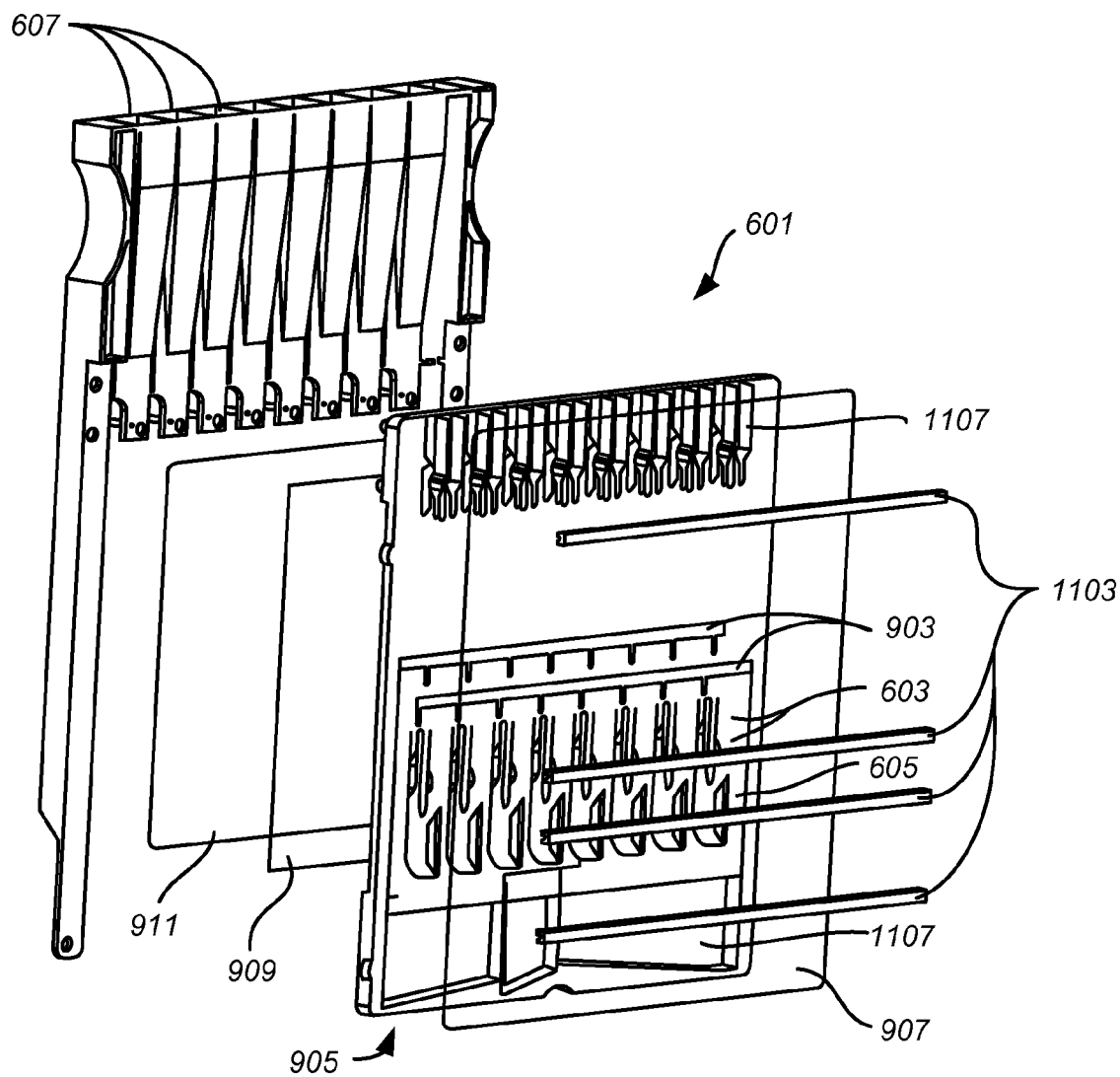
FIG. 6 shows cartridge 601 comprising a plurality of sample receptacles 607 and comprising reagent chambers in piece 905, distribution channels 903 that distribute reagents from reservoirs 603 across a plurality of fluidic circuits. Piece 905 includes reagent chambers 1107. Piece 905 is covered with deformable layer 907. Clamping elements 1103 apply pressure to deformable layer 907. Deformation of the deformable layer against piece 907 blocks movement of liquid through passages. This prevents movement of reagents through fluidic circuits during shipping.
Figure 7:
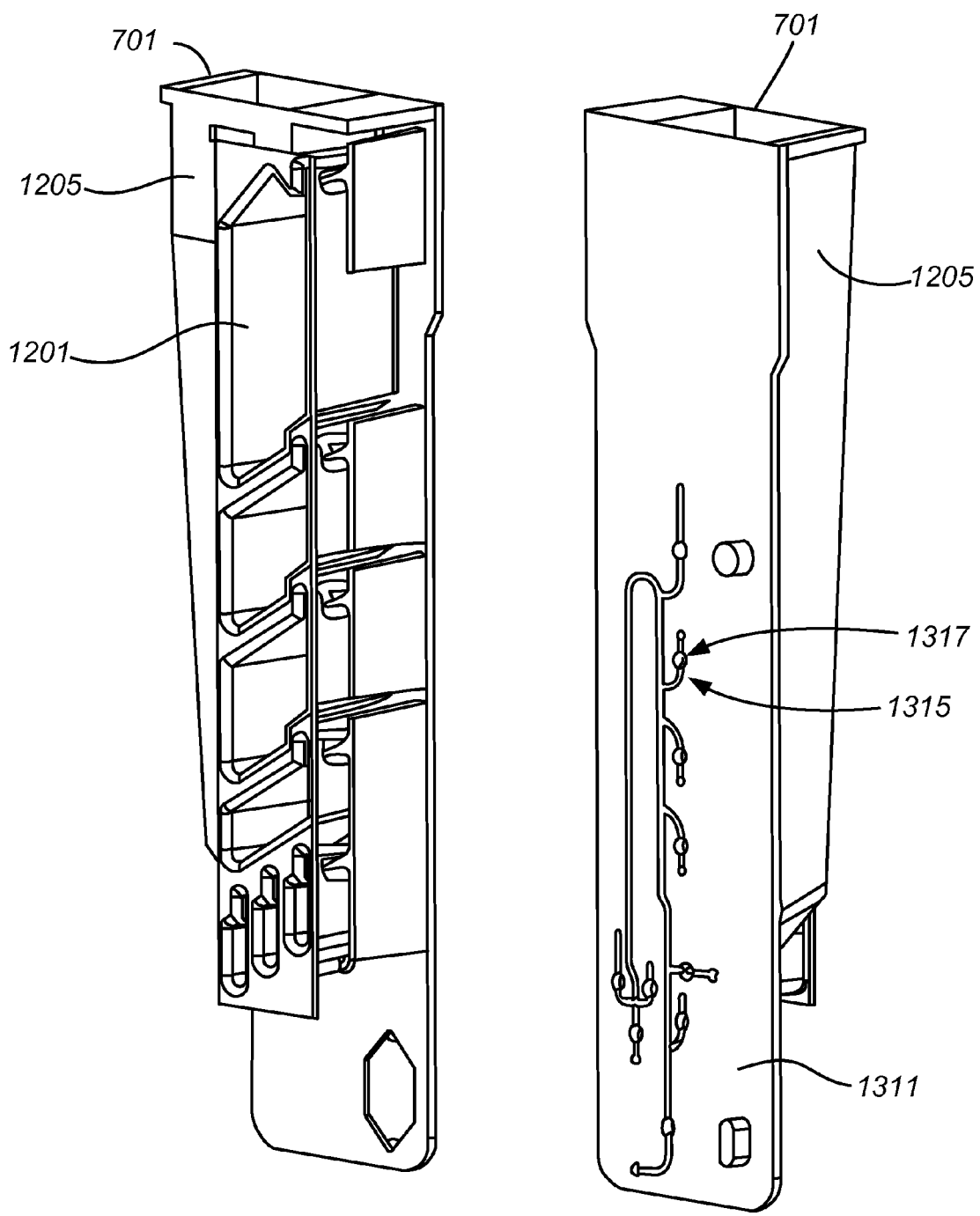
FIG. 7 shows a cartridge 701 comprising a body 1205 having, on side 1311, fluidic channel 1315 and valve seat 1317. On another side, the cartridge has a reagent container having open compartments 1201 that can comprise a seal of a layer of material, for example through a heat seal, to fluidically isolate fluids contained in the compartments until use.
Figure 9:
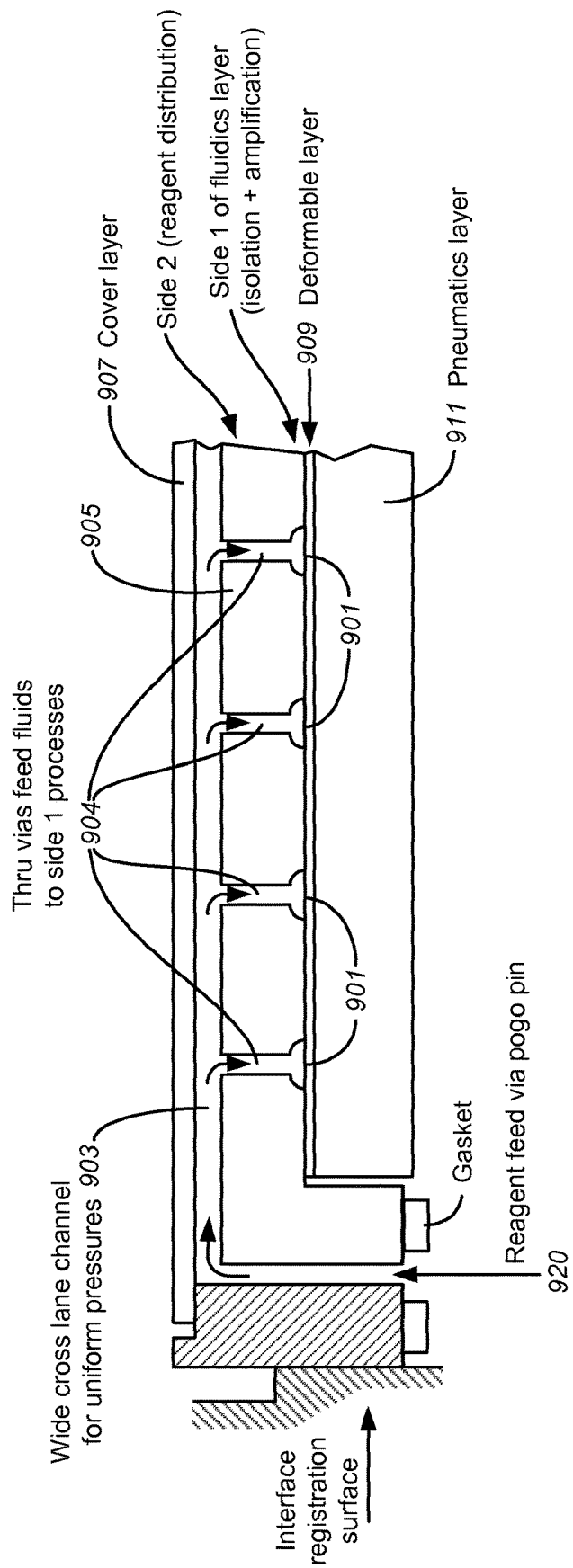
FIG. 9 shows an embodiment of a cartridge having a fluid distribution channel. Body 905 comprises a surface on one side that comprises a plurality of fluidic channels 901 oriented in a first direction. Body 905 also comprises a surface on a second side comprising a channel 903 having an orientation that is oblique to the first direction, for example, at right angles to the first direction. Channel 903 on a second side communicates with each of a plurality of fluidic channels on the first side through vias 904 that traverse body 905. Channel 903 is closed by a cover layer 907. Channel 903 optionally communicates with a source of fluid through a bore 920 in piece 905. Fluid channels 901 are covered by a deformable layer 909. Channels 901 also can comprise valve seats. Portions of the deformable layer can function as diaphragms to open or close the valves. These can be operated through pneumatic layer 911 comprising pneumatic channels that actuate the diaphragms. Alternatively, the cartridge can be engaged with an interface that provides an actuation force to the diaphragms.

A double-sided fluidic layer offers a number of capabilities for multi-sample cartridges, such as an embodiment as shown in FIG. 6. For example, as shown in FIG. 9, if the circuits for individual samples are on one side of the fluidic layer, e.g., through channel 901, the other side of the fluidic layer could provide right-to-left channels, e.g., 903, to distribute reagents. Reagent distribution can otherwise require an additional fluidics part or external manifold.

III. Pneumatic Channels to Selectively Block Diaphragm Valves

Figure 10:
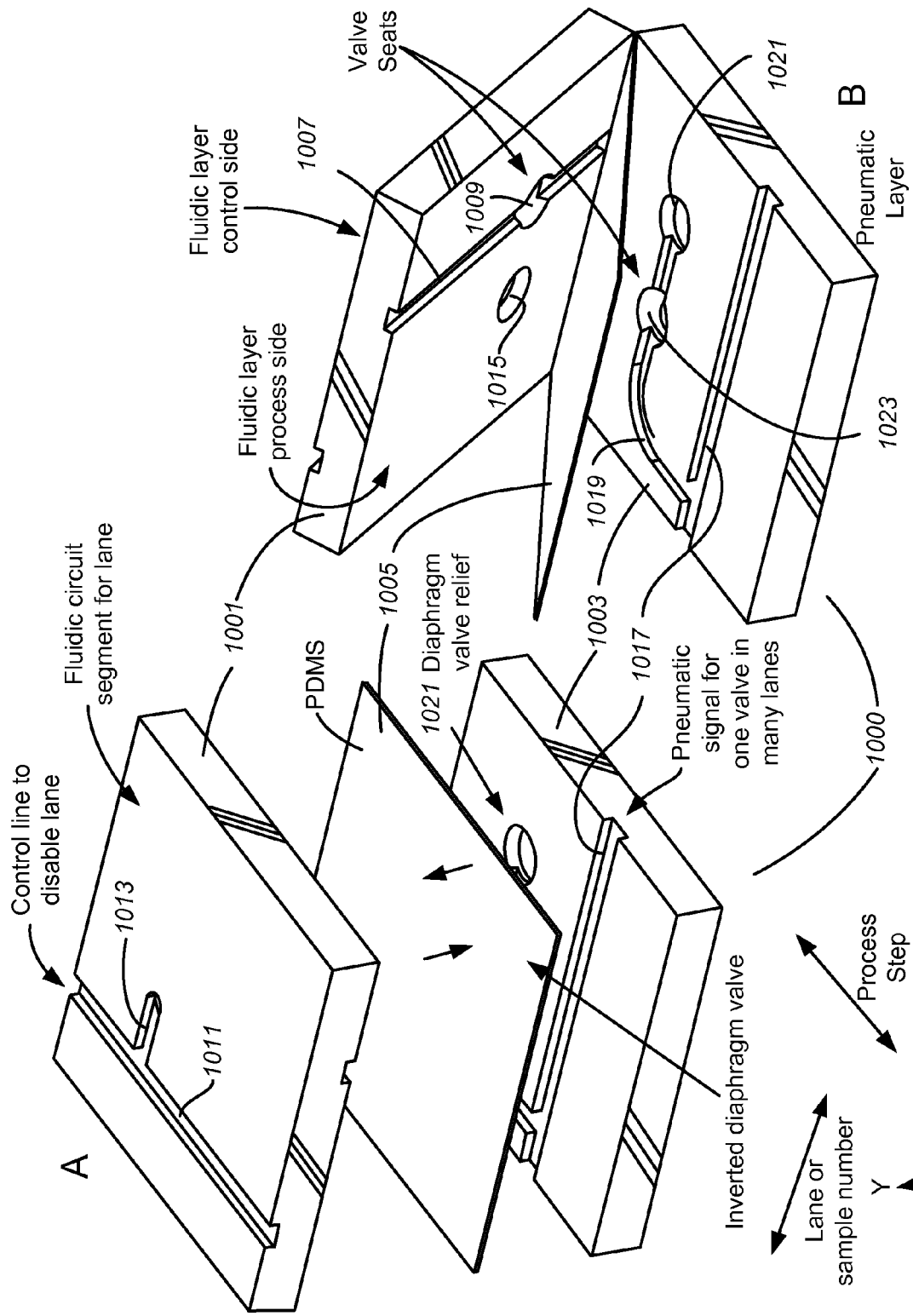
FIGS. 10A and 10B show a segment of cartridge 1000 having a control line configured to disable a selected diaphragm valve in the cartridge.

The right-to-left channels can also route pneumatic control signals to enable or disable specific circuits, as shown in FIG. 10. This selective enabling or disabling of circuits can permit some samples to be run immediately, and other circuits to be reserved to run samples later.

IV. Cartridges Having a Deformable Layer Sealed to a Plastic Body

Cartridges of this disclosure can have a body comprising a solid material. The solid material can be rigid, plastic (capable of irreversible deformation) or elastic (capable or reversible deformation). The body can be stiff or compliant. In some embodiments, the solid material is a polymer, e.g., a thermoplastic, such as polypropylene. The body can comprise an external surface comprising elements of fluidic circuits, such as channels, compartments, vias and valve seats. The body can be made by injection molding of the thermoplastic. These features can be covered with a layer of material attached to the surface of the cartridge body. The layer can function to seal otherwise open features such as channels and compartments. The material can be a deformable material that can deform to contact a valve seat, thereby closing the valve. In certain embodiments, the solid material is inelastic (not capable of elastic deformation). For example, the solid material is not an elastomer, such as PDMS.

The material can be attached to the surface of the body using a selective bonding process in which the material bonds to selected portions of the surface during the bonding process and does not bond to un-selected portions of the circuit after the bonding process is complete. For example, the material may bond to surfaces other than fluidic elements during the bonding process, and not bond to fluidic elements, such as channels and valve seats, after the bonding process. Methods for selective bonding include, for example, thermal bonding (e.g., heat sealing, welding, laser welding), chemical bonding (e.g., chemical bonding of oxide to PDMS) and selectively placed adhesives.

In one embodiment a layer of the deformable material is attached to a surface of a cartridge body through thermal bonding. This can include thermally bonding the material directly to the surface, or thermally bonding the material through an intermediate layer of material. In the latter case the material can be a laminate in which a deformable material is coated with a layer of material that contacts the surface and that melts at lower temperature. In either case bonding typically comprises contacting the deformable material to the body to form a combination and using a die to apply heat and pressure to the combination. Application of heat and pressure melts substrates in locations at which the material and body are in contact and fuse them, e.g., through coalescence. This process is more generally referred to as welding.

A material that bonds to a body through application of heat and pressure is referred to herein as "heat seal". Heat seals are well known in the art and are commercially available. For example, 4titude (Wolton, Surrey, UK) commercializes a variety of heat seals. These heat seals are described on the website 4ti.co.uk/sealing/heat-seals/. These include, for example, Clear Seal, Clear Weld Seal and Foil Seal. Heat seals also are produced by Axygen, a Corning brand (Corning, Tewksbury, Mass., USA). These include Axygen® PlateMax heat sealing film and sealing film rolls. See the website: catalog2.corning.com/LifeSciences/en-US/Shopping/Product.aspx?categoryname=Genomics+and+Proteomics(Lifesciences)%7cPCR+Products(Life sciences)%7cSealing+Films+and+Tapes+for+Microplates(Lifesciences)%7cHeat+Sealing+Films+and+Tapes+for+Microplates(Lifesciences).

The deformable material can be a homogenous or non homogenous material. In certain embodiments, the heat seal material is made from the same material as the body of the cartridge. It can comprise a thermoplastic (e.g., polypropylene, polyethylene, polystyrene, cycloolefin co-polymer (COC), mylar, polyacetate) or a metal (e.g., aluminum). See, e.g., WO 2012/136333. The heat seal can be produced by contacting a heat seal layer with the body and applying heat and pressure. Non-homogenous films include laminates having a first side for contact with the heater and a second side for contact with the body. The first side has higher melting temperature ("high melt") than the second side ('low melt"). This permits use of a heat source to bring the lower side to its melting temperature before the first side allowing bonding to the body without bonding to the heater.

In the single sample cartridge, one side of the body into which compartments are formed is covered in a film or foil that can be adhered or thermally attached to the body. This encloses a second functional layer while only requiring one molded part. This permits functional details—valves, channels, etc. on different sides of the body. In the case of the single sample cartridge, this permits the valves, pneumatic connections, and fluidic connections to be on one side of the cartridge, while the reaction chamber is on a different side of the cartridge. As a result, the temperature regulator controlling the reaction chamber temperature can do so through a thin film, rather than the deformable gasket, which can result in quicker and more controlled thermocycling.

Figure 13:
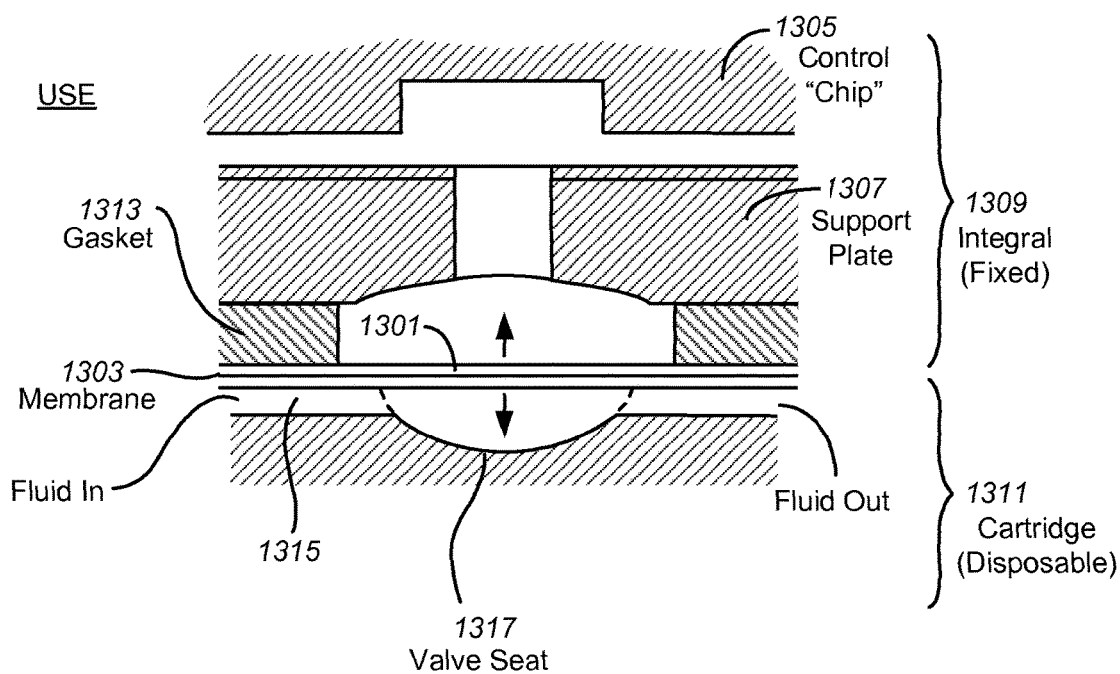
FIG. 13 shows a diaphragm valve with a thin sealing layer 1303 that can comprise a heat seal material.
Figure 14:
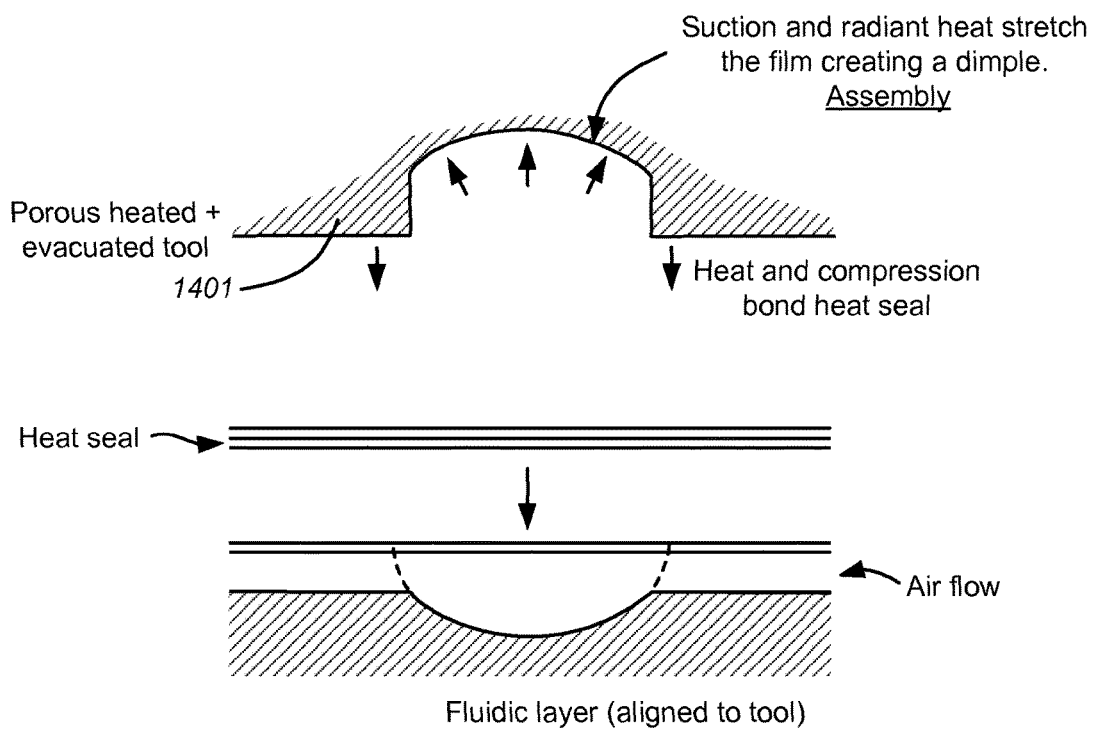
FIG. 14 shows a tool for introducing a dimple into a diaphragm.
Figure 15A:
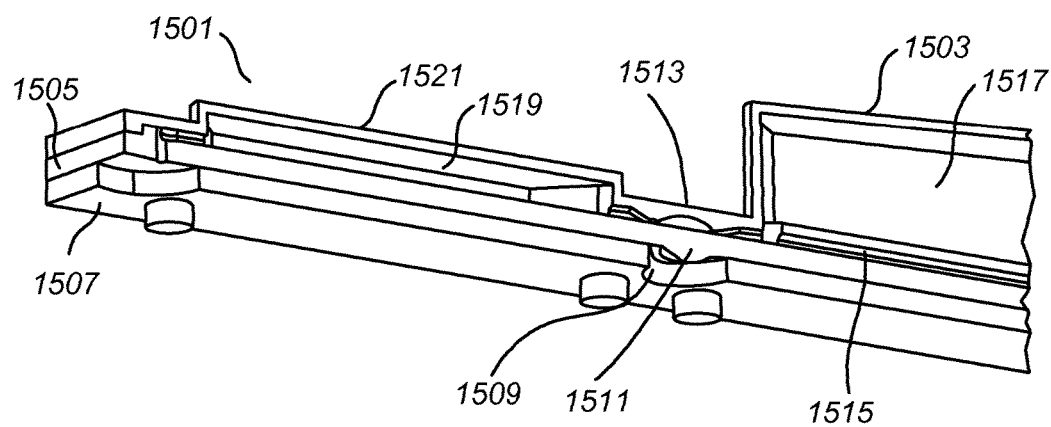
FIGS. 15A and 15B show cartridge 1501 having a body 1503 attached to an deformable layer 1505 and having a cover 1507 on the deformable layer so that the deformable layer in the cartridge is not open-faced. This cartridge includes a diaphragm valve 1513 that is normally open and that regulates fluid flow along a fluidic channel 1515. The cover 1507 covers the deformable layer and comprises an aperture 1509. The deformable layer includes a boss 1511 fitted with the aperture. A mechanical actuator, such as a piston, can be used to close the valve by actuating the diaphragm by the provided boss. This cartridge further comprises a chamber 1517 for receiving a swab or other sample and a reaction chamber 1519 in fluidic communication with channel 1515. The reaction chamber 1521 can be covered with a seal and/or can have a separate heat spreader layer 1521.
Figure 15B:
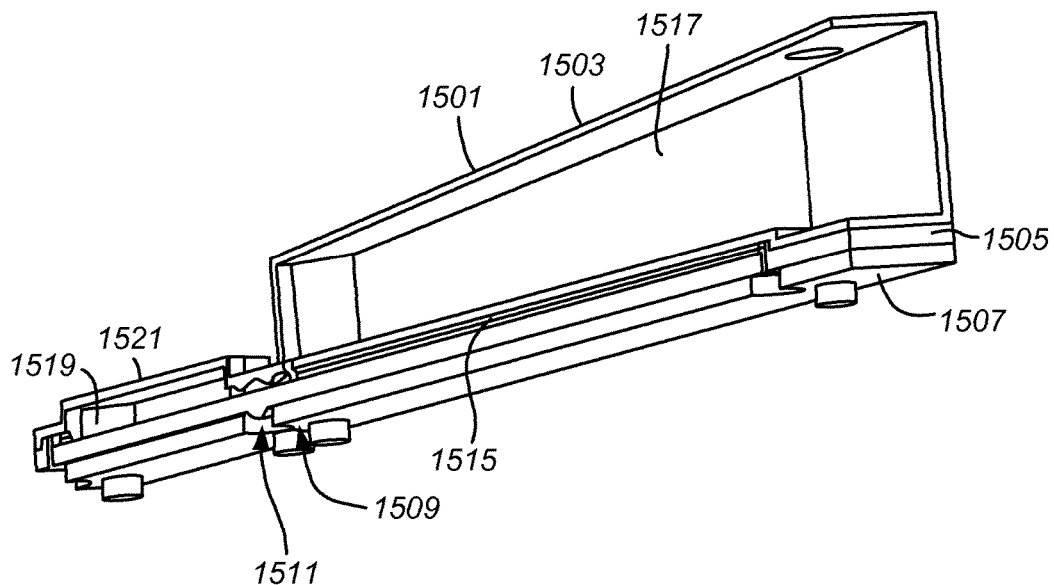

Referring to FIG. 13, in this embodiment, the valve diaphragms 1301 are formed by a film, such as a plastic film. These films are sealed to the cartridge body 1311, enclosing the fluidic circuit 1315. The sealing can be through a heat-seal, a pressure-seal, laser welding, chemical bonding, adhesive or other method well known to one skilled in the art. These valves can be actuated by a control circuit on the system 1305. However, the control circuit can be a permanent part of the system interface 1309 and need not be part of the disposable cartridge 1311. This control circuit can be mounted to a mechanical support plate, with through vias to conduct the pneumatic signals. Gaskets 1313 between the support plate 1307, control circuit 1305, and the cartridge will prevent leaks. In one embodiment the gaskets 1313 can be part of the interface 1309. In an alternative embodiment the gaskets 1313 can be part of the disposable cartridge 1311.

Depending on the film used, there can be a slight overhang around the perimeter of the valve, channel, or volume. This overhang can be due to adhesive or plastic flow during bonding. To prevent these from affecting the quality of the valve seal, the valve inlet, outlet, or both can be through vias in the valve seat 1317. The valve seat, away from the perimeter, can be less affected by the overhang.

Because of the limited flexibility of the film, it may be necessary to create a dimple over the valves. This can be achieved by coining the film downwards against the valve, with the limitation that the heat applied must not be enough to bond the film to the valve seat. A preferred approach would be to vacuform the dimples. The ordinary process of heat sealing involves applying a combination of heat and pressure to create a bond. If the heated tool (1401) was made from a porous material and had cavities cut above the valves, suction could be applied that can draw the film over the valve into the cavity, creating a dimple. This can occur at the same time as the film was being bonded to the body in other areas.

This embodiment can allow multiple fabrication and material options. For example, PDMS, which is commonly used in microfluidics, could be replaced with such a material, such as the heat seal films. This embodiment also reduces requirement for flatness in pieces, permitting other cartridge materials, such as polypropylene.

Figure 8:
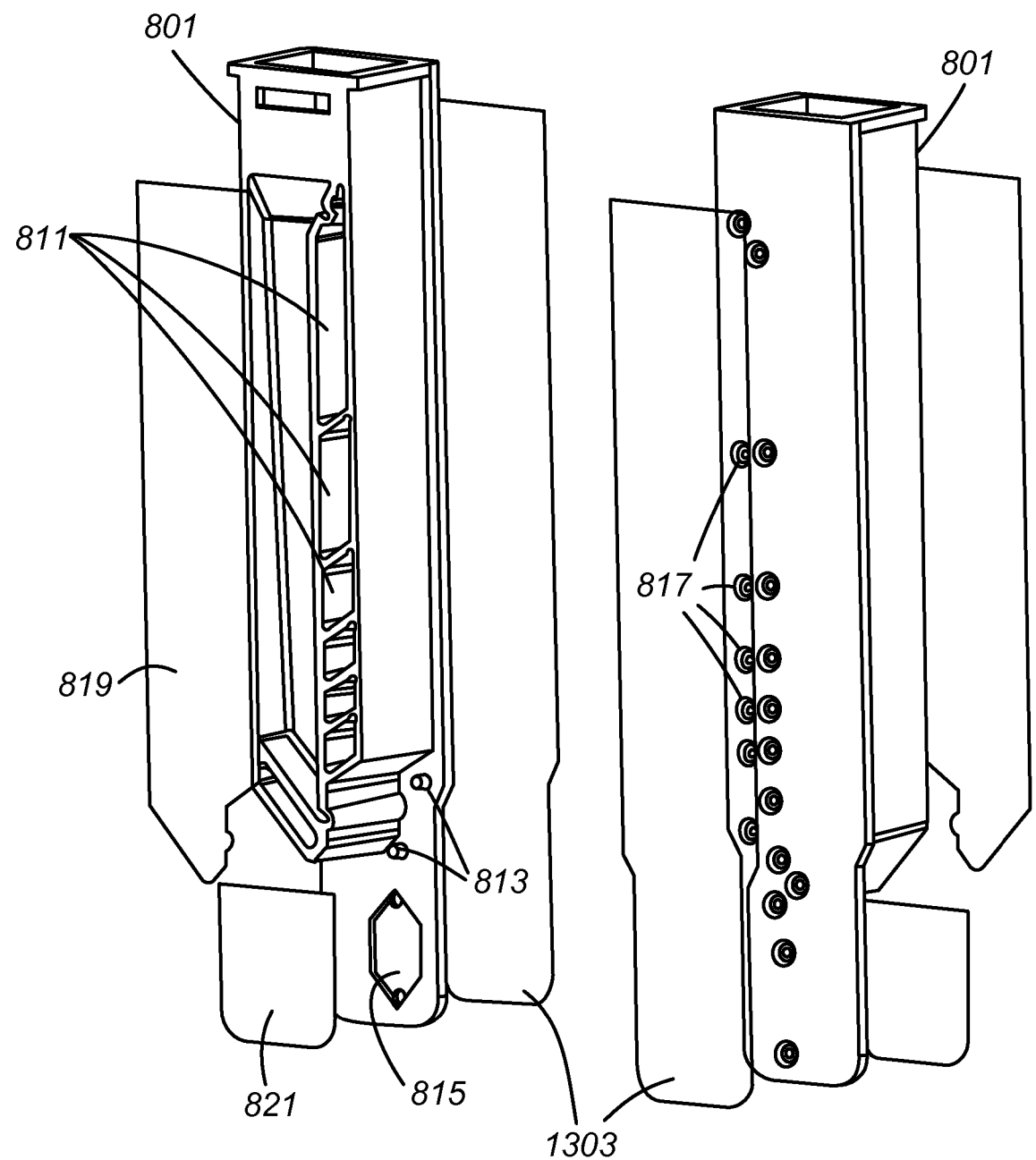
FIG. 8 shows a cartridge 801 comprising a body having a first side having open compartments 811, ports 813 and reaction chamber 815. The body also has a second side comprising valve seats 817. The layer 819 can be bonded to the first side of the body, sealing off the open compartments. The film 821 is capable of transmitting heat and will cover and seal reaction chamber 815. The deformable layer 1303 provides areas that function as diaphragms. When pressed against the second side, for example by a clamping device, the deformable layer 1303 is pressed into the valve seats, closing the valves and preventing fluid movement through fluidic circuits until use.

The use of the fluidics layer for reagent storage and the use of sections of the enclosing film for shipping as in the embodiment of 601, and the use of sections of the enclosing film to implement valves as in the embodiment of 701, permits the cartridge functions to be served by one molded piece and one or more bonded films. Another embodiment, as shown in FIG. 8, uses this construction.

V. Clamp-Sealed Cartridges

Figure 11:
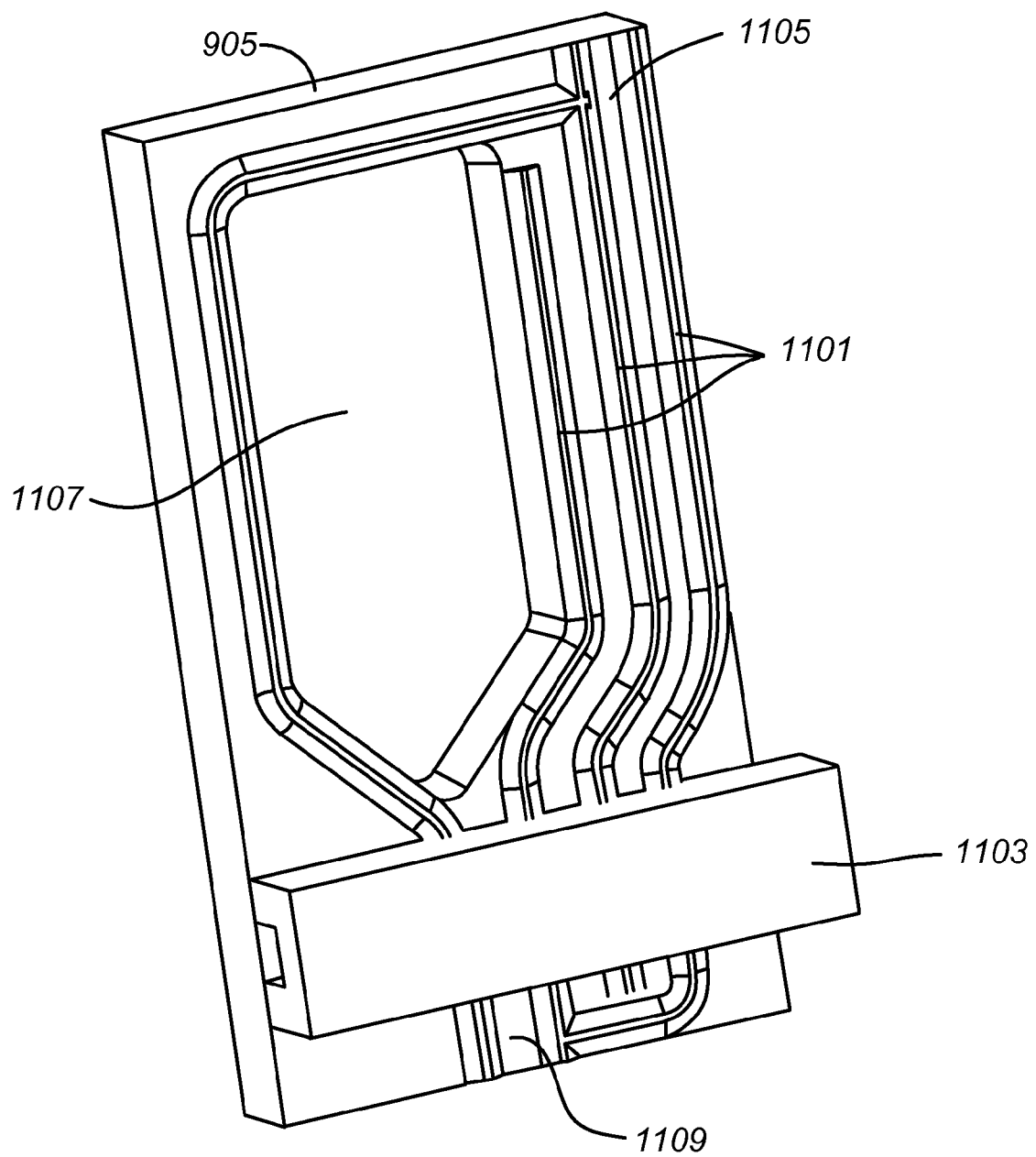
FIG. 11 shows a shipping clamp 1103 on cartridge 905.

FIG. 11 shows a section of the cartridge 601. By using raised lines or areas, e.g., ridges, 1101 to control the bonding of the film, vents can be built into the fluidic layer 905. These raised areas can provide a localized contact when bonding, controlling which areas are bonded and which areas are not, resulting in defined channels.

To close off the outlets 1109 and vents 1105 to these reagent chambers 1107, bar clamps 1103 can be built into the shipping container for the cartridge. These bar clamps can have some rigidity, but can be covered by a deformable or other material that can conform to the cartridge surface. It may have a basic shape or be formed to mate with the cartridge surface.

Bar clamp 1103 is able to hold the seal film cover (907, not shown in FIG. 11) against the body or fluidic layer 905, closing off the defined channels. After shipment but before use, the cartridge is removed from its packaging, which either removes the shipping clamps as the packaging is opened, or the clamps are removed separately from the cartridge after the cartridge is removed from the packaging.

If the flexible bar clamp is U-shaped as shown, it can close each channel in two places to prevent leakage. The operator will then be able to confirm that no leakage has taken place by examining the area between the two seals. Any leakage past both seals will generally leave a residual amount between the two seals.

Before use, the two vias leading to each of the reagent reservoirs are held closed by a shipping clamp. This shipping clamp can apply a uniform force to a flexible pad, causing the pad to deform and hold the valves closed. Alternatively, it can include a number of small rubber contacts that can individually hold each valve closed. This shipping clamp can then be removed before the cartridge is inserted into the system.

VI. Diaphragm Valve with a Bossed Diaphragm

Diaphragm valves also can be actuated mechanically using a ram, e.g., a pin. These can be actuated by a solenoid. If actuated by solenoid, it may be beneficial to add a boss (such as element 1511) to the outside of the deformable. This permits a ram to push against the boss, creating a centered force sealing the valve, even if the solenoid is not centered over the valve.

VII. Turret Cartridge

Cartridges actuated mainly by a syringe pump or by a manually operated syringe are included in this instant disclosure. The cartridges can be controlled by motors controlled by the computer on the system.

One embodiment of a cartridge utilizes a syringe pump for actuation, with selectable, specialized areas arranged in a ring. These areas can each store reagents, house the swab or punch, contact a temperature regulator, connect to the capillary for separation, etc.

Figure 17:
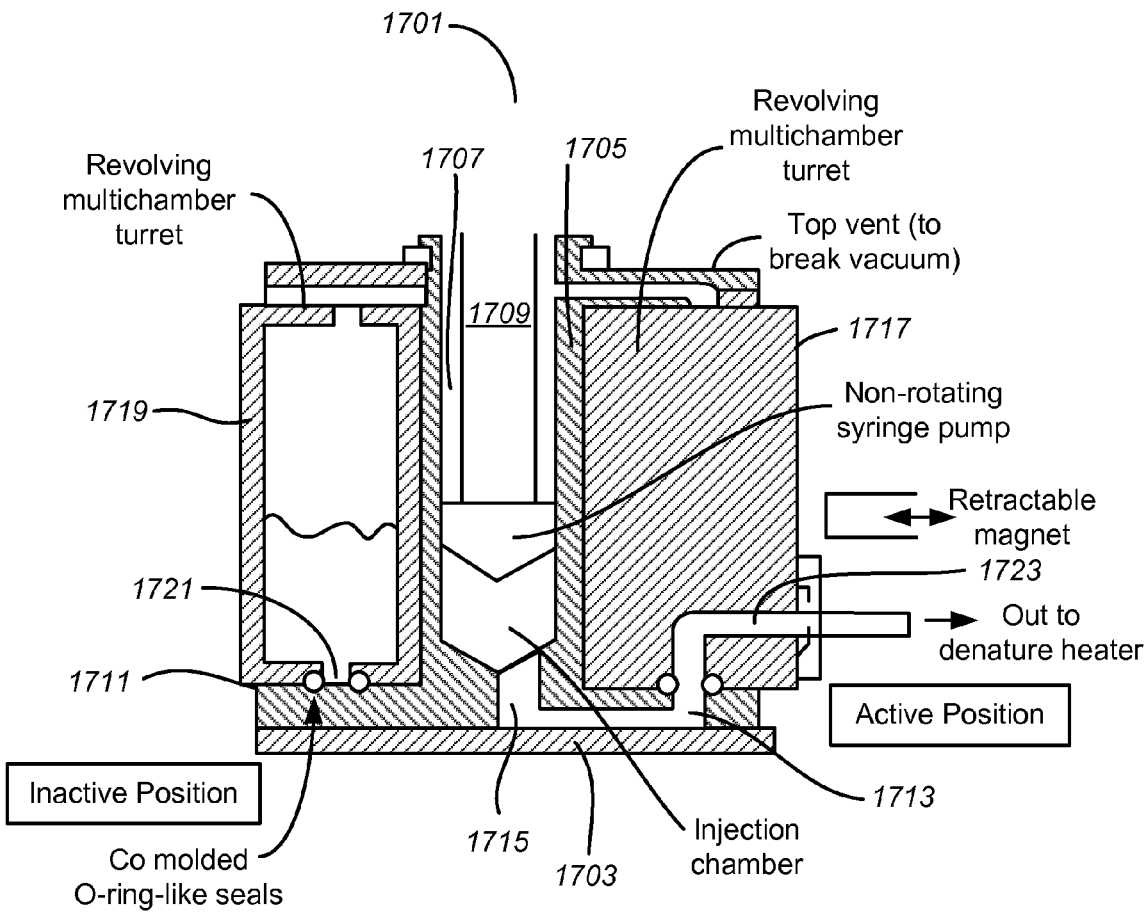
FIG. 17 shows a revolving multi-chamber turret. Cartridge 1701 comprises a base 1703. The base has a central barrel 1705 comprising a pump chamber 1707 and movable syringe 1709, a floor 1711 comprising a port station comprising a port 1713 and a channel 1715 fluidically connecting the barrel chamber to the port in the floor. The cartridge also has a turret 1717 configured to revolve around the central barrel 1705 and comprising a plurality of turret chambers (e.g., 1719), each turret chamber comprising a turret chamber aperture 1721, wherein the turret is configured to rotate around the syringe barrel, wherein positioning a turret chamber at the port station puts the turret chamber aperture in fluid communication with the barrel chamber through the floor aperture and wherein the floor covers a turret chamber aperture when turret chamber is positioned at least one position other than port station. At least one turret chamber further comprises a channel communicating between the port and an exit port 1723.

Referring to FIG. 17, the cartridge can implement a rotary selector valve, either by rotating the cartridge body 1717 or an internal valve. By rotating, various inputs or outputs can be selected. This rotation can be driven by, for example, a stepper motor. The syringe 1709 can in turn be driven by for example, a linear stepper motor. This permits a broad range of general functions to be controlled by two stepper motors. The interface can also make use of one or more temperature regulators. Thermocycling can be implemented by cycling the temperature of a temperature regulator, or by rotating to contact one of multiple controlled heat sources to reduce the power usage and may increase thermocycling speed. It can also have an LED, filter, and photodiode for reaction quantification.

One, two or three positions on the hub can be temperature controlled. One position on the hub can be open on top, for sample insertion. One or more positions can have external, retractable magnets.

Turret cambers can include: (A) Vent: air to injection chamber; (B) Vent: to denature heater; (C) lysis chamber/swab vial; (D) lysis buffer/Waste; (E) mix chamber/beads; (F) water; (G) ethanol; (H) STR lyosphere (amplification reagents); (I) capture solution and size standard (or lyosphere); (J) eluting agent; (K) electrophoresis separation gel; (L) reaction chamber.

Gel injection may be to a booster pump instead of directly to the capillary. This would avoid the need for high-pressure seals, in the sample cartridge (This would permit gel injection in parallel with other functions.) If the capillary can be mounted directly, denature heading may be complete by one of the heated positions, without an external denature heater. An external waste gate, at the cathode end of the capillary may still be necessary.

This embodiment can permit an interface consisting of one rotary and one stepper motor, eliminating pneumatic pumps, manifolds, anode module/gel filling mechanism, etc.

VIII. Lead-In Guiding Fluid Delivery Pogo Pin

Figure 18A:
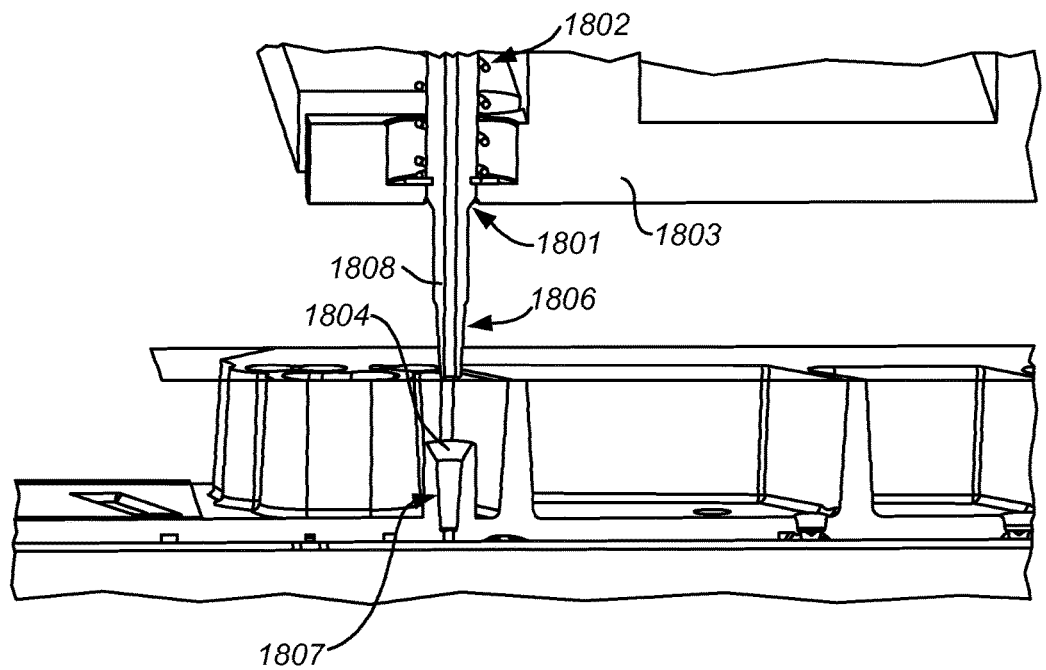
FIGS. 18A and 18B shows cross-sectional views of a self-aligning, self-resetting pogo pin 1801 reset into its home position, and fluidically connected to the cartridge, respectively.
Figure 18B:
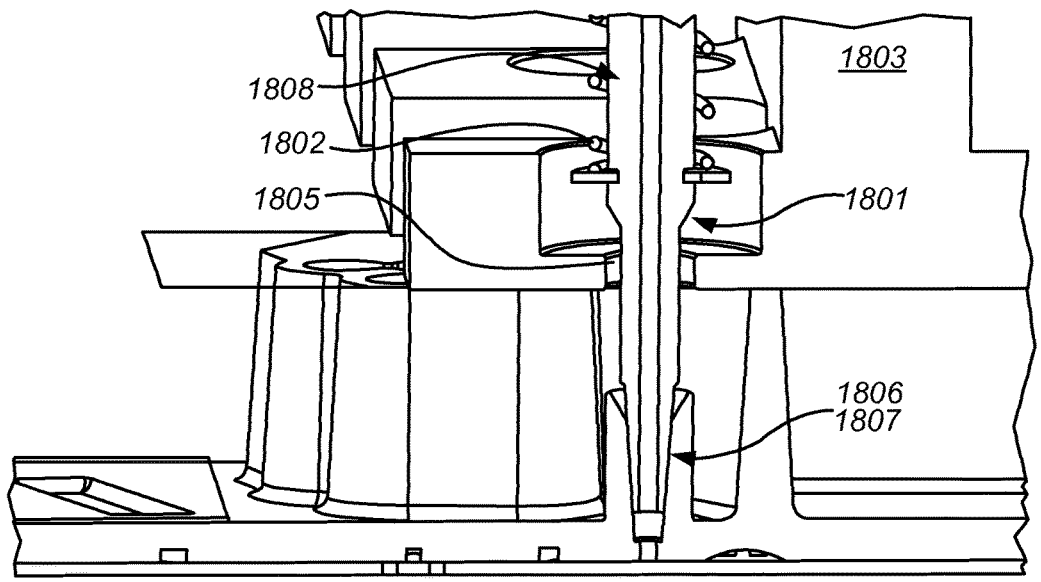

FIGS. 18A and 18B show a low-dead-volume floating connector 1808 in cross-section. When the interface is open as shown in FIG. 18A, the pogo is forced down against the home lead-in 1801 by a spring 1802. This will reset the pin to a consistent home position relative to the pogo block 1803. When the interface closes onto a cartridge that is off-center, the pogo contacts the engagement lead-in 1804 and is pushed up, freeing the engagement play 1805. The engagement lead-in then guides the cartridge within this play. Once aligned, the conic surfaces of the pogo pin 1806 and cartridge 1807 connect. The slight taper magnifies the force of the spring, creating a seal. This seal requires some flexibility in the cartridge. Since the surrounding wall thickness is driven by the engagement lead-in, this limits the lead-in size. The engagement lead-in 1804 and the engagement play 1805 will both need to be large enough to accommodate all manufacturing and other tolerance variations. If the pogo pins did not self-reset to a consistent home position, the engagement lead-in can changed to accommodate variations from the engagement play as well.

IX. Vent Tabs

Figure 12:
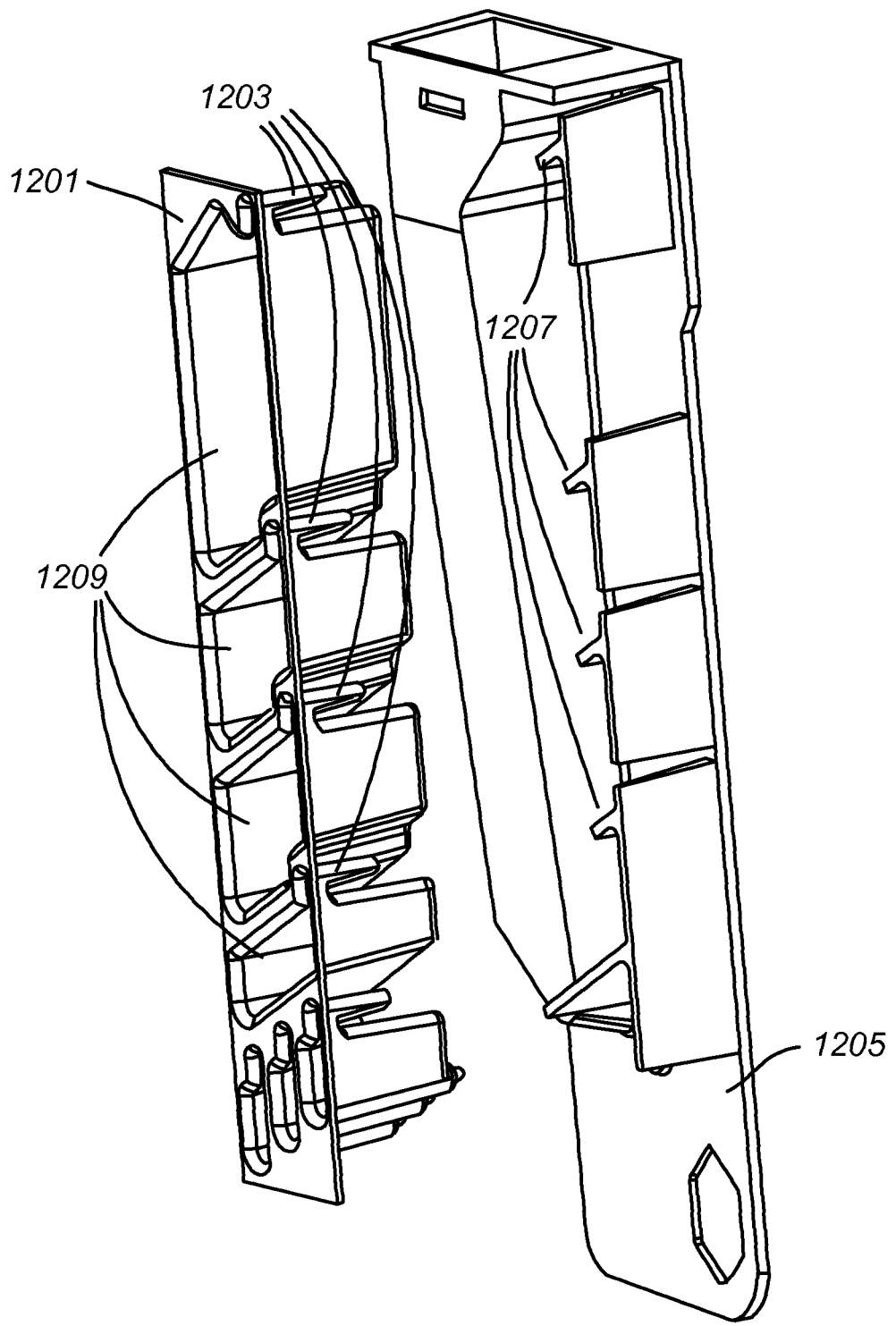
FIG. 12 shows a cartridge comprising a body 1205 and a reagent reservoir 1201. The reagent reservoir has compartments, 1209, that can contain a liquid and that can be sealed with a layer such as heat seal, chemical seal, adhesive or laser weld. The body can comprise puncturing elements (not shown) to puncture seals in a floor of compartment 1209 when the reagent reservoir is pressed against the body. The puncturing elements can be a solid material, e.g., that protrude from the body, and that may have a tapered end that is pointed or sharp and that is adapted to apply concentrated pressure to the floor and to puncture a hole in the floor. This creates a fluidic connection between the compartment and a fluidic circuit in body 1205. This combination also includes flanges 1207 and breakable tabs 1203. When reagent reservoir 1201 is pressed against body 1205, flange 1207 engages tab 1203 and applies a force which breaks tab 1203, thereby creating a vent in compartment 1209. This allows fluid in compartment 1209 to drain through the aperture in the floor of the compartment and into the fluidic circuit.

In an embodiment shown in FIG. 12, the cartridge includes two injection molded plastic parts, a cartridge body and a reagent reservoir. When in use, the reagent reservoir can be pressed against the body. This can snap open the vents, and engage connections between the body and the reservoir.

For cartridge concepts that have bodies 1205 and moveable reagent reservoirs 1201, such as the cartridge of the embodiment of 701, there is another approach to providing vents. This approach does not require additional parts. This is to build in designed-to-fail tabs (e.g., 1203) into the reagent reservoir. Before use, these tabs will remain closed, but will have a slight interference with the cartridge body 1205. When the reagent reservoir is engaged by pressing, these tabs will try to pull away from the main volume. It will tear or crack, opening a small vent in the reservoir.

This embodiment can provide a vent for on-cartridge reagent reservoirs without requiring additional degree of freedom in the interface or additional part in the cartridge.

The cartridge can utilize off-cartridge pumps to move liquids.

To avoid the need for high mechanical precision, these valves and channels can be larger than traditional microfluidic valves and channels.

X. Fluidic Device with Diaphragm Valve

The cartridge of this disclosure can include diaphragm valves. Diaphragm valve can be formed having a valve chamber in the fluidics layer of the cartridge and a deformable membrane attached to a surface of the fluidics layer and providing a diaphragm for opening and closing valve. In one embodiment, the valves are normally open. That is, at ambient pressure the valve is open and closing the valve involves applying positive pressure to the diaphragm opposite the valve seat. Applying negative pressure to the diaphragm opposite the valve seat can further open the valve. The diaphragm can be actuated by pneumatic or mechanical pressure. In an embodiment of this disclosure the diaphragm is mechanically actuated by positive pressure applied by a ram or rod having an end configured for insertion into the valve chamber. In certain embodiments the rod has a compliant end that promotes contact between the diaphragm and a valve seat, thereby sealing the valve closed. Withdrawal of the rod relieves pressure on the diaphragm, thereby opening the valve.

In one embodiment of a normally open valve, a surface of the fluidics layer comprises a recess that both defines a valve chamber and functions as a valve seat. At ambient pressure the deformable membrane does not sit against the valve seat and the valve is in an open configuration. Positive pressure on the deformable membrane from the side opposite the fluidics layer pushes the deformable membrane against the valve seat, closing the valve. The valve seat can take a curved shape that is convex with respect to the surface of the fluidic layer, against which the deformable membrane can conform. For example, the valve shape can be a section of a sphere or an inverted dimple or a dome. Such a configuration decreases the dead volume of the valve, e.g., by not including a valve chamber that contains liquid while the valve is closed. This valve also comprises a surface against which the deformable membrane can conform easily to close the valve. In another embodiment, the concave surface can comprise within it a sub-section having a convex surface, e.g., an inverted dimple comprising an extraverted dimple within it forming, for example, a saddle shape. The convex area rises up to meet the deformable membrane under pressure, creating a better seal for the valve.

Valve seats can be recessed with respect to the rest of the surface by about 25 microns to about 1000 microns, e.g., about 700 microns. Valves can communicate with fluidic channels that are either microfluidic or macrofluidic (e.g., having an aspect less than 500 microns or having an aspect greater than 500 microns or at least 1000 microns). In certain embodiments of a normally open valve, the concavity is recessed less than the channels to which it is connected. In certain embodiments the channels can enter partially into the concavity, for example forming a vault. In certain embodiments, the channels and concavity are formed by micromachining, injection molding or embossing.

XI. Valve Actuated by Ram with Compliant End

One embodiment involves closing a fluidic valve with a ram. The valve can be comprised in substrate that contains the valve and one or more input and output fluidic channels. There can be more than one input and output. These channels can enter the surface of the dome valve at any location on the surface as long as there is a sealing surface between channels. In certain embodiments, channels can enter the valve chamber through vias that connect with the channels. The dome valve is then covered with a membrane either elastic or non-elastic film. The film is affixed to the perimeter of the dome to create an air and liquid tight seal. The ram is then pressed against the film diaphragm with sufficient force to deform the diaphragm and press the film onto the dome surface. The pressure from the ram creates a fluidic seal between the orifices of the ports entering the dome valve.

In one embodiment the valve is configured as a router. The router can have, for example, four inlets/outlets. In this configuration the forked ram, when engaged, can block access to the router by some, but not all, of the inlets/outlets. For example, the forked ram could allow fluid flow through the router in a north-south direction or not it in an East-West direction.

The ram is structured such that there are one or more flexure posts defining an identical dome surface to match the valve dome surface with the offset of the thickness of the diaphragm. The flexure posts with the seal seat tips will be able to self align to the target seal areas of the dome, namely the perimeter of the orifice for the input and output channels of the valve. The flexure posts also concentrate the stress generated by the force applied to the overall post onto the active seal area.

Figure 29:
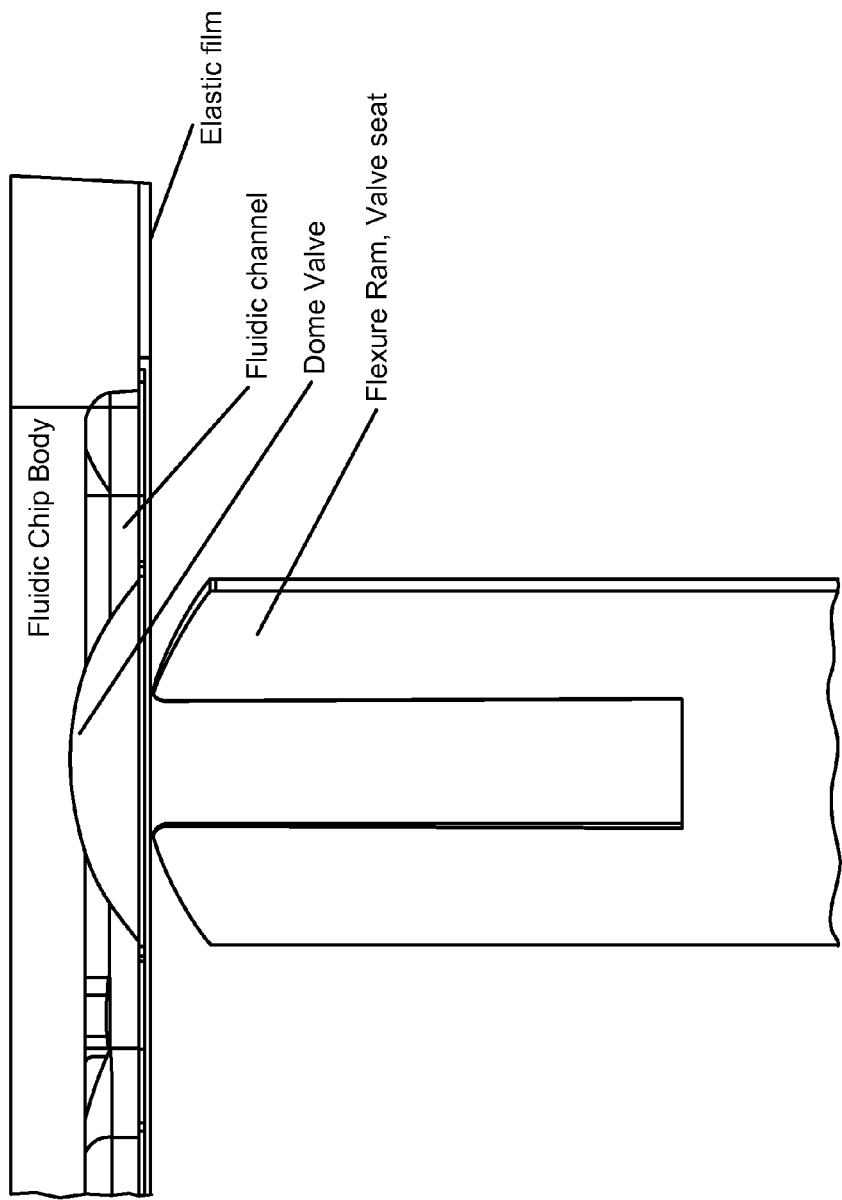
FIG. 29 shows a cutaway view of a normally open valve actuated by a ram having a tip with flexible elements.
Figure 30:
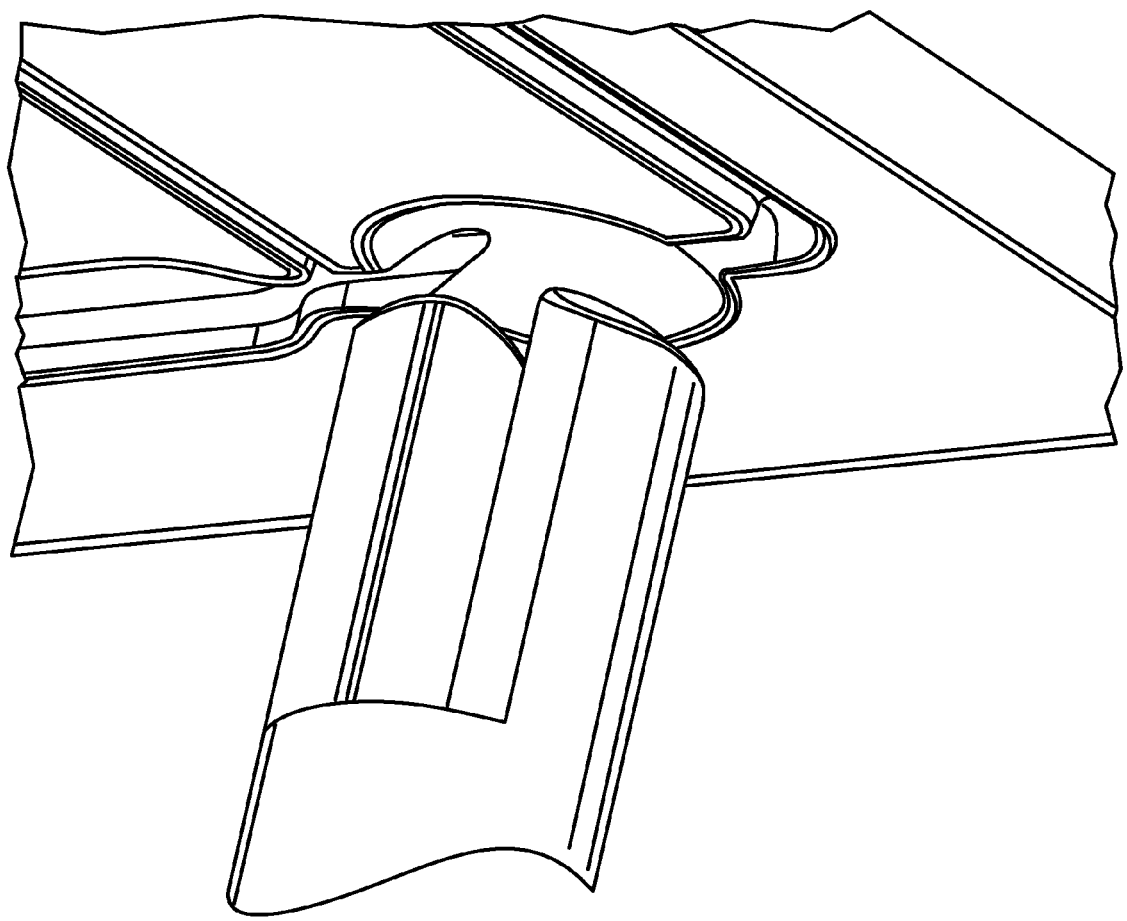
FIG. 30 shows a three-dimensional view of a valve of this disclosure.
Figure 31:
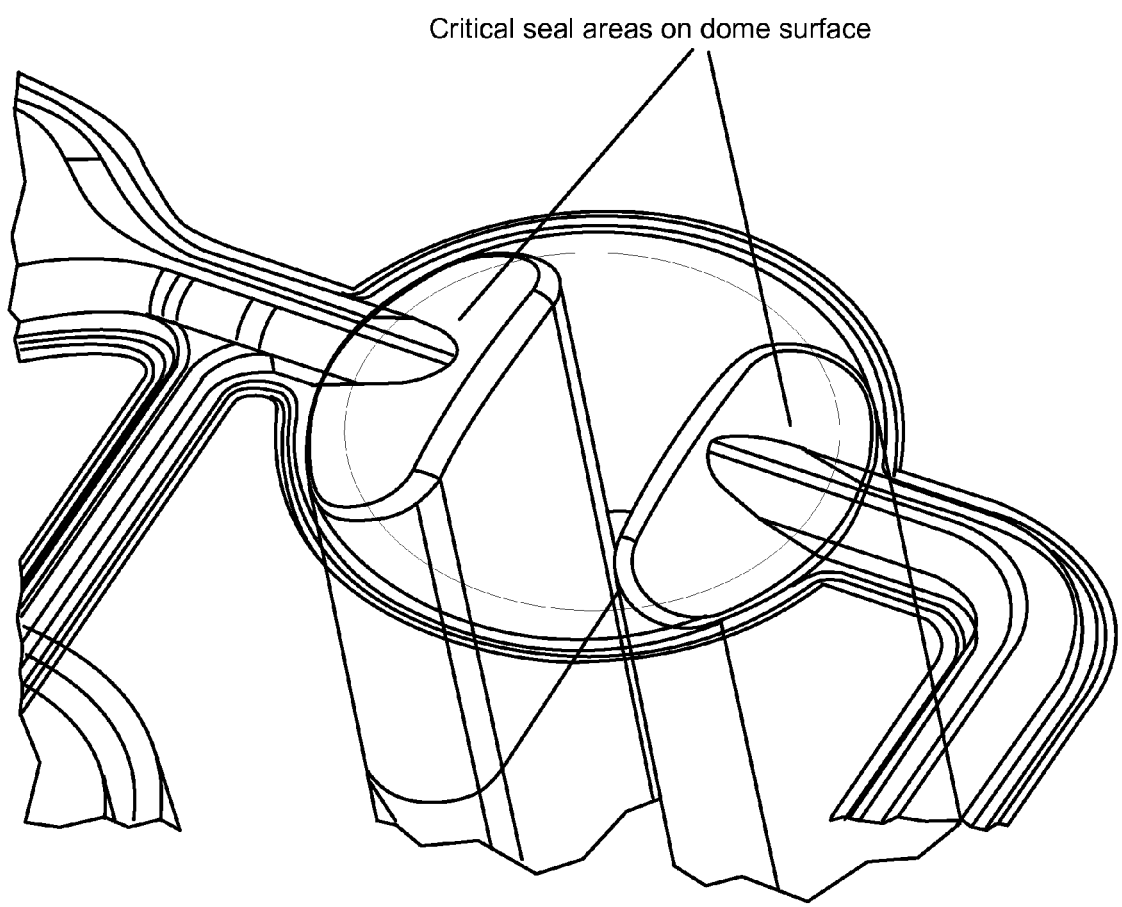
FIG. 31 shows a valve of this disclosure in a closed configuration. A flexible end of the ram presses a deformable membrane against a valve seat. The ram is configured to press the deformable membrane so as to seal the valve inlet and the valve outlet by pressure against the perimeter of the inlet and outlet in the valve seat.
Figure 32:
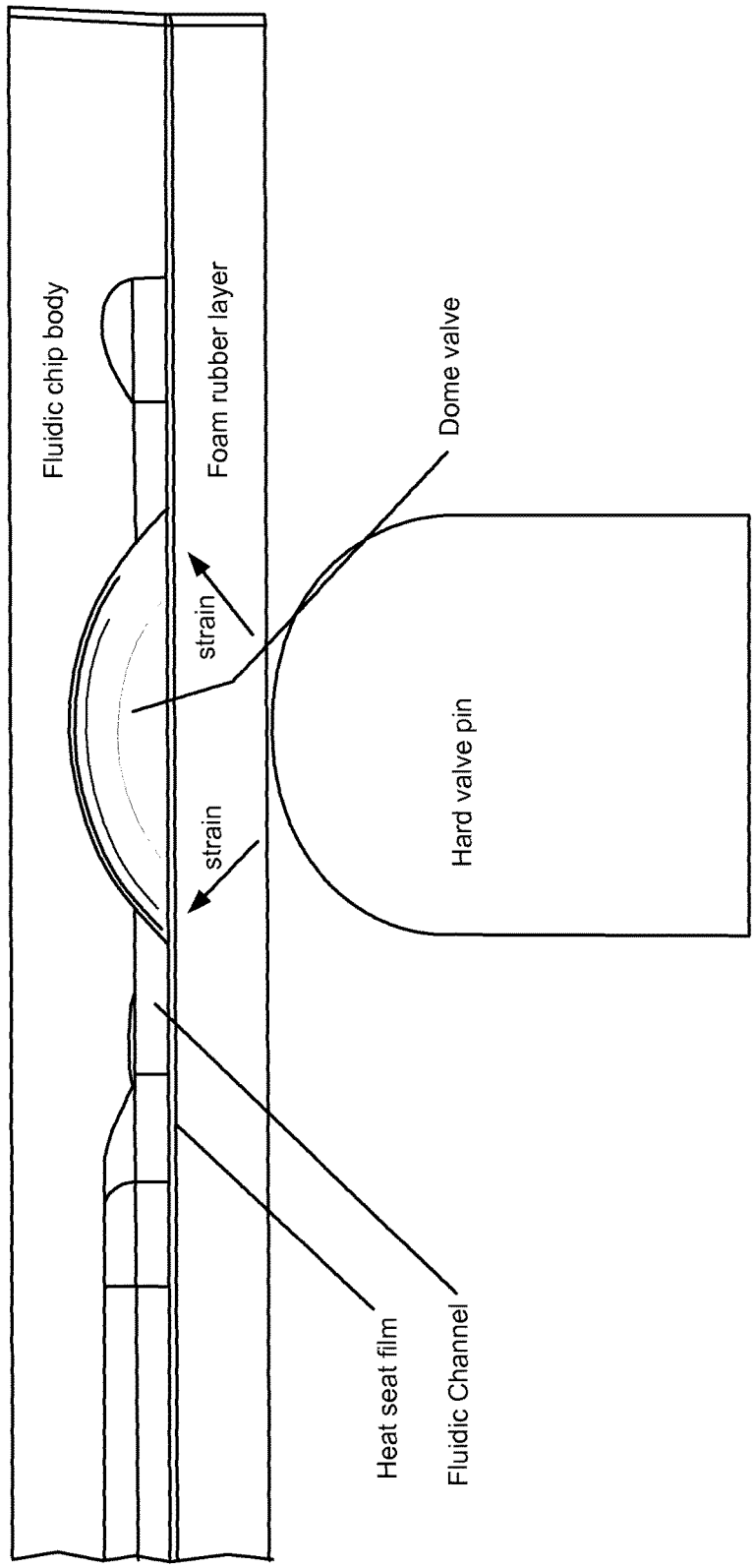
FIG. 32 shows a valve having a valve chamber defined by a recess in a fluidic layer and a diaphragm comprised in a laminate layer.

Referring to FIGS. 29 and 30, a fluid chip body comprises a recess forming a valve seat ("dome valve"). The recess defines a space that functions as a valve chamber. The fluidic chip body also includes fluidic channels (which can be microfluidic channels) in fluid communication with the valve through inlets and outlets. A surface of a fluidic chip body into which the recesses impose is overlaid with a deformable membrane ("elastic film"). A ram actuates the valve by applying pressure to deformable membrane. The ram can include a fork or slotted end that provides compliance to the flexure posts tines of the fork. An end of the ram has a form that complies with the shape of the valve seat. Referring to FIG. 31, when pressed against the deformable membrane, the ram deforms the deformable membrane against the valve seat. By contacting the valve seat around the valve inlet and valve outlet, the diaphragm closes the valve, preventing fluid flow through the valve. Relieving pressure on the diaphragm by withdrawing the ram allows the deformable membrane to assume its neutral position, opening the valve to fluid flow. The ram can be actuated, for example, by a solenoid.

XII. Reaction Chamber

In one embodiment a fluidic device of this disclosure comprises a reaction chamber that comprises a solid substrate, e.g., solid phase extraction material, for retaining analyte from the sample. The solid substrate can comprise a material that binds the analyte, such as a nucleic acid such as DNA. The amount of solid substrate in a chamber and the selected to retain the predefined amount of analyte. For example, the material can be a Whatman FTA paper or a carboxylated material. Alternatively, the solid substrate can be an absorbent or sponge-like material that absorbs a predetermined volume of fluid. The material can be in the form of a monolith. The material can be, for example, PVDF (polyvinyldiene fluoride) membranes, filter paper, glass particles, silica, or other solid phase extraction material. In operation, lysate is pumped through the chamber and a predetermined amount of analyte is retained on a solid substrate. Then, retained material is contacted with reagents, e.g., reagents for PCR. The resulting material can be incubated to form a reaction product. For example, the chamber can be put into thermal contact with a thermal-control device, such as a Peltier, and the reaction mixture can be thermal cycled. In another embodiment, the chamber can include a pocket or container designed to retain the defined volume of liquid.

XIII. Contaminant Deactivation

In one embodiment the fluidic layer includes a waste chamber. A waste chamber can contain material that degrades nucleic acids, polypeptides, or other analytes. For example a material can comprise a chlorinated material, such as calcium hypochlorite. Alternatively, the waste chamber can include in absorbent material that absorbs waste containing liquid In another embodiment the nucleic acid degrading material is contained in a water-soluble capsules in yet another embodiment the nucleic acid degrading material is combined with an absorbent material such as cellulose or polypropylene fibers.

In another embodiment, the waste chamber contains enzymes that degrade the nucleic acids (e.g., nucleases), polypeptides (e.g., proteases), or other analytes such as phosphorylated sites (e.g. phosphatases).

XIV. Cartridge and Method

Figure 21:
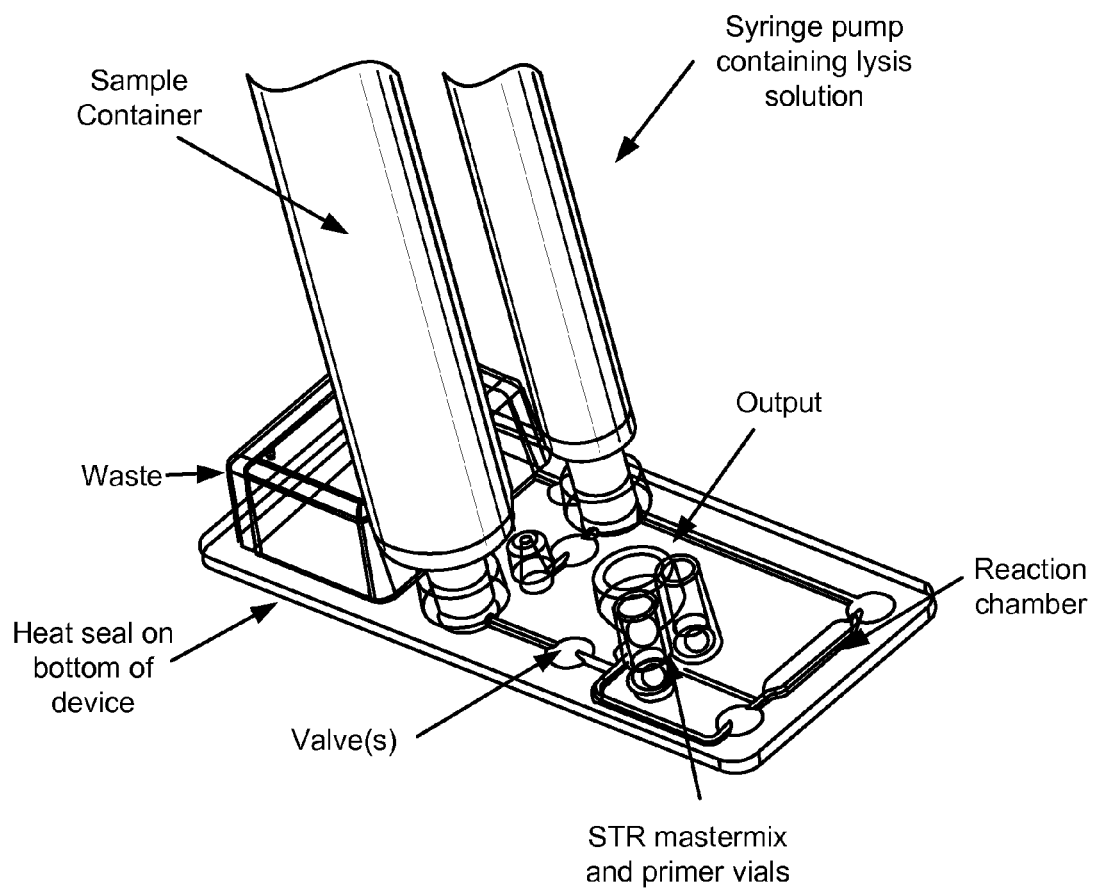
FIG. 21 shows a schematic of a cartridge of this disclosure.
Figure 22:
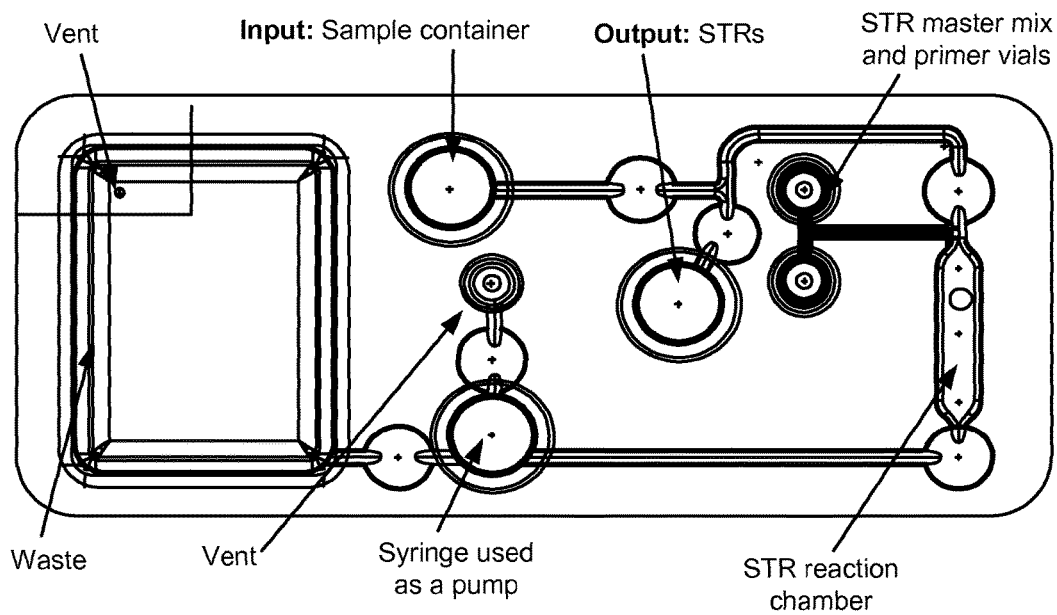
FIG. 22 shows a bottom view of a cartridge circuit.

FIGS. 21 and 22 shows a fluidic cartridge configured for extracting nucleic acid from a sample, performing amplification on the sample, and outputting the amplification product. The cartridge includes a port configured to accept a sample container adapted to receive a sample, such as a swab; a port configured to accept a syringe pump containing or connected to reagents, such a lysis solution; a port configured to accept receptacles separately carrying PCR master mix and PCR primers; a reaction chamber, e.g., for thermal cycling; a waste chamber; a vent; an output port; fluidic channels (which can be microfluidic or macrofluidic channels) in communication with these elements; valves for regulating flow of fluids in the fluidics circuit all of the cartridge. The valves can be, for example, diaphragm valves.

Figure 23:
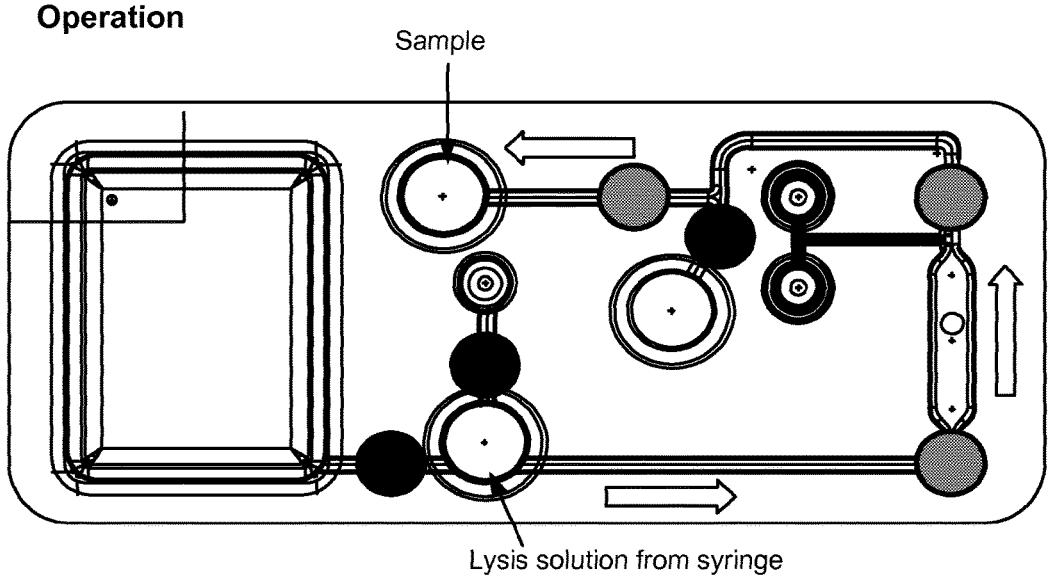
FIG. 23 shows the valve states and flow for a cell lysis operation.
Figure 24:
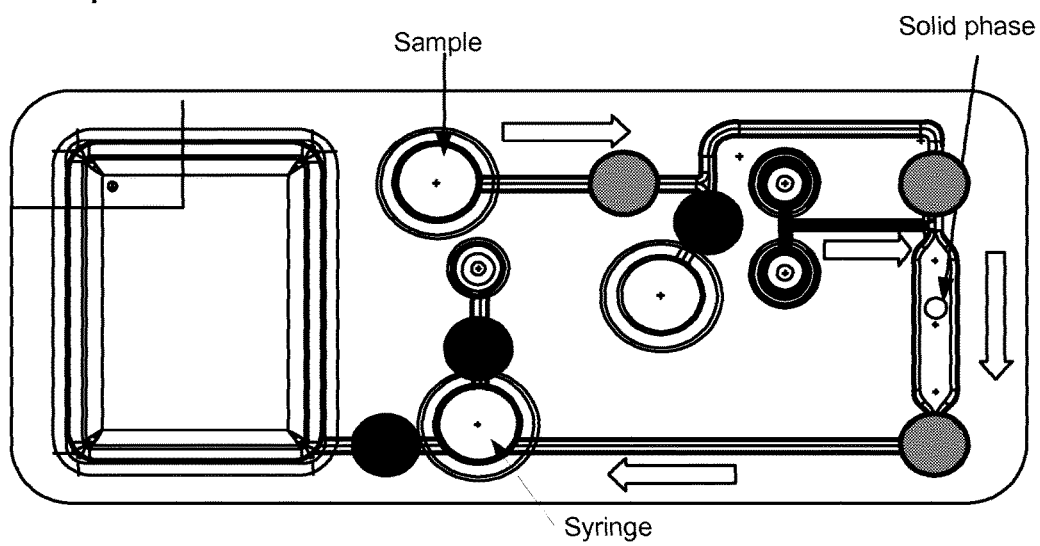
FIG. 24 shows the valve states and flow for nucleic acid capture.
Figure 25:
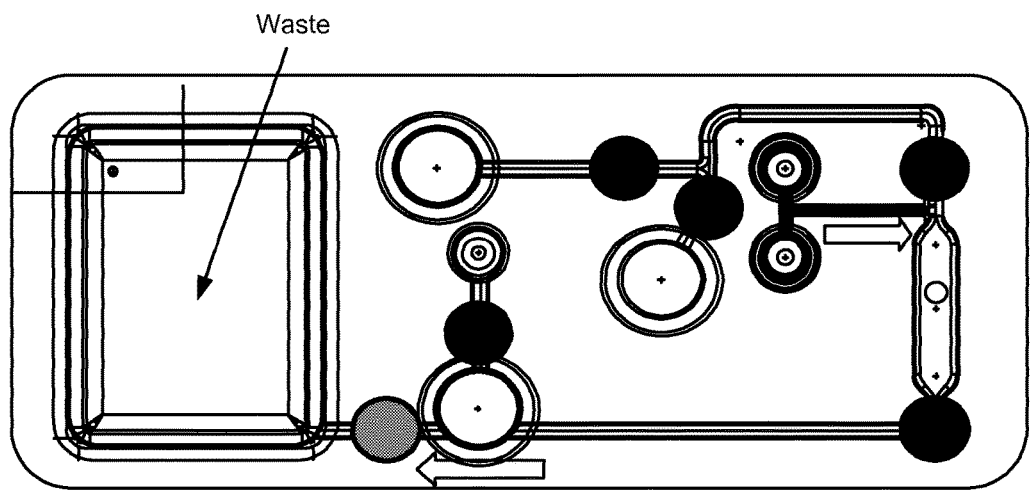
FIG. 25 shows the valve states and flow for movement of liquid into a waste chamber.
Figure 26:
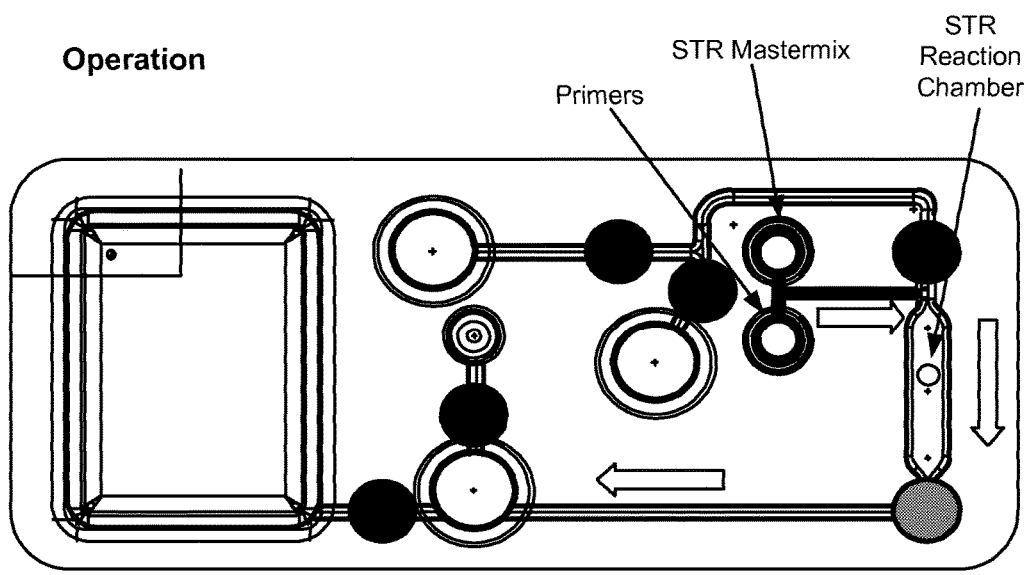
FIG. 26 shows the valve states and flow for creation of a reaction mixture.
Figure 27:
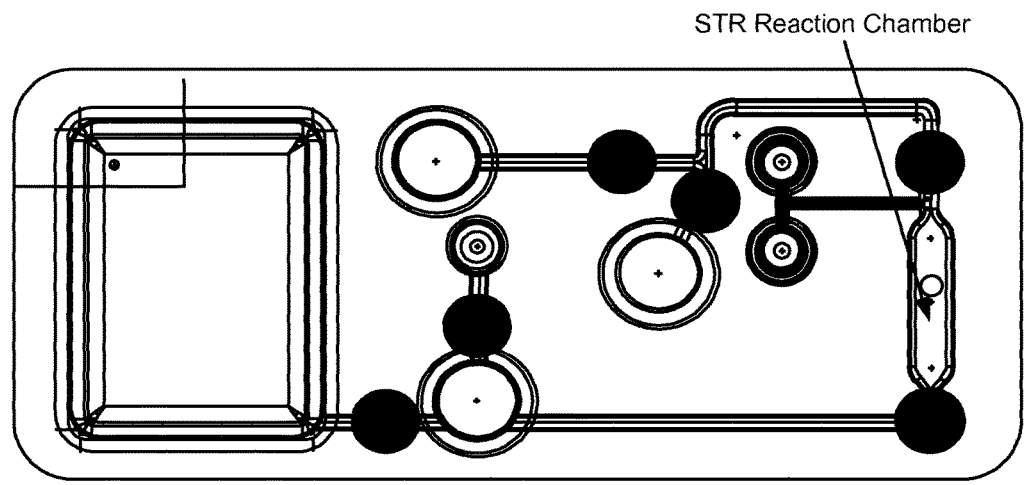
FIG. 27 shows the valve states for thermal cycling.
Figure 28:
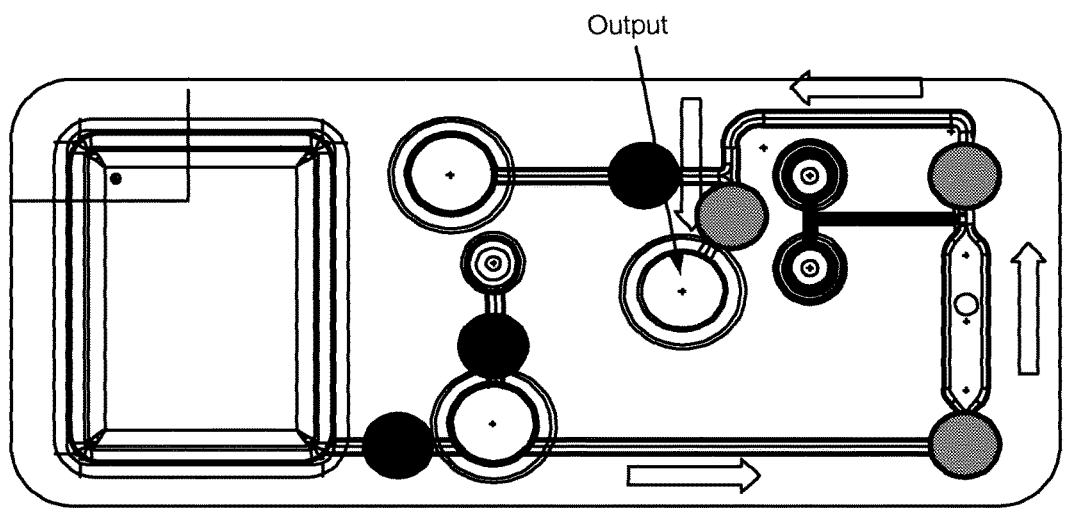
FIG. 28 shows the valve states and flow for movement of the amplification product to output ports.

FIG. 23 shows the operation of a cartridge. Closed valves are indicated in darker shade, open valves are indicated in lighter shade. Arrows indicate the flow of liquids which are moved by the syringe. Lysis solution from the syringe is moved through a fluidic channel into the container containing a sample. The sample can be heated or sonicated to facilitate cell lysis. In FIG. 24 lysate is pulled back into the syringe and nucleic acid is captured on a solid phase in the reaction chamber. In FIG. 25 lysis solution is transported into the waste chamber. In FIG. 26 PCR master mix and primers, which can be contained in separate containers, are moved into the reaction chamber, for example pushing the liquid from one side as the syringe provides vacuum from another side. In FIG. 27, the reaction chamber is subjected to thermal cycling to amplify target sequences, for example, STR sequences, while all the valves are closed. In FIG. 28 the amplification product is moved to an output port where it can be transferred for further analysis.

XV. Integrated System

The cartridges of this disclosure are useful in integrated and automated sample-to-answer systems that, starting from a sample comprising biological material, generate an analysis of the sample. In certain embodiments, the biological material is DNA and the genetic profile involves determining one or a plurality of alleles at one or a plurality of loci (e.g., genetic loci) of a subject, for example, a STR (short tandem repeat) profile, for example as used in the CODIS system. The system can perform several operations, including (a) extraction and isolation of nucleic acid; (b) amplification of nucleotide sequences at selected loci (e.g., genetic loci); and (c) detection and analysis of amplification product. These operations can be carried out in a system that comprises several integrated modules, including an analyte preparation module; a detection and analysis module and a control module.

Systems provided herein may be fully integrated. Sample processing can be accomplished in a single system without having to remove a sample and transfer it to another system. Systems provided herein can be fully automated, enabling a user to process a sample without substantial input from the user.

A sample preparation module includes a cartridge module assembly configured to engage and operate one or more than one sample cartridge. A sample cartridge is configured to receive one or more samples and to perform nucleic acid extraction and isolation, and DNA amplification when the cartridge is engaged with a cartridge module assembly in the system. It can also include controls and standards for assisting in analysis. In other embodiments, a sample cartridge is configured to receive one or more samples and to perform cell lysis, and enzymatic assays when the cartridge is engaged with a cartridge module assembly in the system.

The sample preparation module can include a receptacle for receiving one or more cartridges, an engagement assembly to engage the cartridge; a fluidic manifold configured to engage ports in a cartridge and to deliver pressure and/or fluids to the cartridge through the ports; a delivery assembly configured to deliver reagents, such as amplification premix, from a compartment in the sample cartridge to an amplification compartment; a pneumatic manifold configured to engage ports in a cartridge and to deliver positive or negative pressure to the cartridge through the ports for moving fluids and operating valves, pumps and routers in the cartridge; a pump configured to deliver pressure to the fluidic and pneumatic manifold. Consumable reagents can be carried in a module, e.g., a buffer module, that is, removably engageable with the cartridge module.

PCR can be carried out using a thermal cycler assembly. This assembly can include thermal controller, such as a Peltier device, infrared radiation source, resistive heating element, circulating water or other fluids, circulating air, movement of constant temperature blocks, or other material, which can be configured to heat and cool for thermal cycling and can be comprised in the cartridge module which can be configured to move the thermal controller into thermal contact with the thermal cycling chambers, for example, through a heat spreader (or thermoconductor that can spread/distribute heat and cooling) disposed over each of the reaction chambers. In some embodiments, the cartridge comprises a temperature regulator assembly having one or more (e.g., 2, 3, 4, 5, 6, 7, 8, 9, 10, 16, 24, 32, 40, 48 or more) thermocycling chambers and the sample cartridge can be in fluid communication with a fluidic channel.

An analysis and detection module is configured to receive analyte from the sample preparation module and perform capillary electrophoresis on the analyte to detect analytes separated by electrophoresis and to analyze the detected analytes. It can include a capillary electrophoresis assembly, a detection assembly, and an analysis assembly.

The capillary electrophoresis assembly can include an injection assembly, that can include a denature heater assembly, a positioning assembly for positioning an analyte for capillary injection; a cathode assembly; a capillary assembly; an anode assembly; a capillary filling assembly for filling a capillary with separation medium and a power source for applying a voltage between the anode and the cathode.

A detection assembly can comprise a laser configured to illuminate the capillaries and a detector. The laser can be configured to excite fluorescent dyes in the analyte. In alternative embodiments, the laser can be replaced by an alternate light source such as an LED. The detector can include a CCD array, photomultiplier, diode array, or other detector, for detecting light produced by excited dyes and for producing an output signal.

An analysis assembly can include a computer comprising memory and a processor for executing code (e.g., code on a tangible medium) for analyzing the output signal and producing a computer file containing an analysis of the signal. Such an analysis can include, for example, identification of alleles from various STR loci. The computer file can be in a format that is compatible with public databases. For example, the file can be in CODIS format which is compatible with the National DNA Index System (NDIS) operated by the FBI.

The system can be operated by a control module. The control module can include a user interface configured to receive instructions from and deliver information to a user. It can include software programmed to execute routines for performing the operations mentioned, above, and transmit and receive information, such as computer files, from remote locations, for example, over the internet.

XVI. Method of Use

The cartridges of this disclosure can be used in an integrated system for preparing a sample, for example, DNA isolation and amplification. For example, in one embodiment, a sample contained on for example a swab or a card punch, can be introduced into sample chamber 207. The chamber can be snapped shut by the lid 211. The cartridge can be engaged with cartridge interface 103. Cell lysis buffer contained in an on-system reservoir can be feed through line 405 through interface assembly 401 into the fluidic channel in the cartridge and into the sample chamber 207. After lysis, lysate can be moved through a fluidic channel on the chip, for example, which pumps the fluid into a reaction chamber 301. In one embodiment, the DNA reaction chamber can include magnetically attractable particles that bind DNA and that can be immobilized in the reaction chamber by applying a magnetic force generated in the interface. This can eliminate the need for an intermediate DNA isolation chamber. Waste fluid can be moved through the cartridge and out through a vent. Reagents for performing PCR or other reactions can introduced into the reaction chamber through one of the fluid lines 405 connected to the interface. A thermal control mechanism in the system can apply heat to perform thermal cycling in a thermal cycling chamber 301 of the cartridge. In some embodiments the heat is applied to a heat transmission element, for example, a foil or metalized film, that improves thermal contact and transmission.

The cartridges of this disclosure can be used in an integrated system for analyzing a sample, for example, DNA isolation and amplification with real time or end point detection. For real time measurement, the samples can be interrogated by an optical detection system while amplifying in reaction chamber 301. The readout can be the change in fluorescence or by melting point. The probes can be human specific for human identification, forensics, or molecular diagnostic applications, or specific for pathogens for molecular diagnostic applications, or for bioagents for biodefense applications or nonspecific intercalators for determining amount of DNA present. Amplification methods include, for example, thermal or isothermal amplification reactions, for example, PCR, rolling circle amplification, whole genome amplification, nucleic acid sequence-based amplification, and single strand displacement amplification, single primer isothermal linear amplification (SPIA), loop-mediated isothermal amplification, ligation-mediated rolling circle amplification and the like The cartridges of this disclosure can be used in an integrated system for analyzing a sample. The assay can detect a polypeptide (e.g., immunoassay) or a nucleic acid (e.g., PCR). The assay can be multiplex or single analyte. They can involve any assay to measure presence, amount, activity, or other characteristics of the sample. These include assays that involve detection by fluorescence, luminescence, chemiluminescence, Raman, absorbance, reflectance, transmittance, birefringence, refractive index, colorimetric and combinations thereof. In this instant disclosure, the enzyme master mix and the substrate might be individually added to the reaction and the progress or endpoint of the assay monitored optically.

For STR applications, after thermal cycling, other reagents such as molecular weight markers (size standards) can be combined with the PCR product. Movement through the cartridge can be controlled when diaphragm valve 303 is actuated by pneumatic or mechanical actuators wherein forces transmitted through line 407. Products of the PCR can be moved off chip for analysis through an output line.

While preferred claims of the present invention have been shown and described herein, it will be obvious to those skilled in the art that such claims are provided by way of example only. Numerous variations, changes, and substitutions will now occur to those skilled in the art without departing from the invention. It should be understood that various alternatives to the claims of the invention described herein may be employed in practicing the invention. It is intended that the following claims define the scope of the invention and that methods and structures within the scope of these claims and their equivalents be covered thereby.

What is claimed is:

1. A fluidic device comprising:
   a fluidics layer comprising one or more fluidic channels in a thermoplastic material;
   a deformable membrane covering the one or more fluidic channels and comprising a heat seal material capable of plastic deformation, the heat seal material being thermally bonded to the fluidics layer;
   one or more diaphragm valves, each diaphragm valve configured to regulate fluid flow in an associated fluidic channel, wherein each diaphragm valve comprises:
   a) a diaphragm comprised in the deformable membrane;
   b) a valve seat in the associated fluidic channel and recessed from a surface of the fluidics layer that contacts the deformable membrane; and
   c) a valve inlet and a valve outlet comprised in the fluidics layer; wherein the one or more diaphragm valves are each configured for activation by a ram such that mechanical pressure by the ram on the deformable membrane presses the membrane against the valve seat, thereby closing the valve.

2. The device of claim 1 wherein the deformable membrane does not comprise an elastomer.

3. The device of claim 1 wherein the deformable membrane comprises a laminate.

4. The device of claim 1 wherein the deformable material has a durometer value of between 10 to 80 Shore D.

5. The device of claim 1, comprising a plurality of diaphragm valves.

6. The device of claim 1, wherein the deformable membrane comprises a permanent deformation.

7. The device of claim 1, wherein the thermoplastic material comprises polypropylene.

8. The device of claim 1, wherein the valve seat has the shape of a sphere, an inverted dimple, a dome, or a saddle.

9. The device of claim 1, comprising one or more fluidic circuits.

10. The device of claim 1, wherein the fluidics layer further comprises a fluidic compartment in fluid communication with a fluidic channel.

11. The device of claim 1, wherein the fluidics layer further comprises an exit port in fluidic communication with a fluidic channel.

12. The device of claim 1, further comprising a ram configured to actuate the diaphragm.

13. The device of claim 1, which does not comprise an actuation layer.

14. The device of claim 1, wherein the deformable membrane comprises a material selected from polypropylene, polyethylene, polystyrene, cycloolefin co-polymer (COC) and polyacetate.

15. The device of claim 1, wherein valve can be opened by releasing pressure of the ram against the deformable membrane.

* * * * *